(12) United States Patent
Brenner et al.

(10) Patent No.: US 12,178,845 B2
(45) Date of Patent: Dec. 31, 2024

(54) METHODS AND COMPOSITIONS RELATING TO THE TREATMENT OF TUMORS

(71) Applicant: THE GENERAL HOSPITAL CORPORATION, Boston, MA (US)

(72) Inventors: Gary J. Brenner, Winchester, MA (US); Giulia Fulci, Cambridge, MA (US); Sherif Ahmed, Somerville, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 1033 days.

(21) Appl. No.: 16/466,336

(22) PCT Filed: Dec. 6, 2017

(86) PCT No.: PCT/US2017/064809
§ 371 (c)(1),
(2) Date: Jun. 4, 2019

(87) PCT Pub. No.: WO2018/106753
PCT Pub. Date: Jun. 14, 2018

(65) Prior Publication Data
US 2019/0336577 A1  Nov. 7, 2019

Related U.S. Application Data

(60) Provisional application No. 62/431,037, filed on Dec. 7, 2016.

(51) Int. Cl.
| | | |
|---|---|---|
| *A61K 38/17* | (2006.01) | |
| *A61K 48/00* | (2006.01) | |
| *A61P 35/00* | (2006.01) | |
| *C07K 14/47* | (2006.01) | |
| *C12N 7/00* | (2006.01) | |
| *C12N 15/86* | (2006.01) | |

(52) U.S. Cl.
CPC ...... *A61K 38/1761* (2013.01); *A61K 48/0058* (2013.01); *A61P 35/00* (2018.01); *C07K 14/4747* (2013.01); *C12N 7/00* (2013.01); *C12N 15/86* (2013.01); *A61K 48/00* (2013.01); *C12N 2750/14143* (2013.01); *C12N 2750/14171* (2013.01); *C12N 2840/007* (2013.01)

(58) Field of Classification Search
CPC ............ A61K 38/1761; A61K 48/0058; C07K 14/4747; C12N 15/86
See application file for complete search history.

(56) References Cited

U.S. PATENT DOCUMENTS

| | | | |
|---|---|---|---|
| 5,139,941 A | 8/1992 | Muzyczka et al. | |
| 5,173,414 A | 12/1992 | Lebkowski et al. | |
| 5,399,346 A | 3/1995 | Anderson et al. | |
| 6,911,306 B1 * | 6/2005 | Vertino | C07H 21/04 435/6 |
| 9,644,215 B2 * | 5/2017 | Brenner et al. | C12N 15/86 |
| 2010/0129359 A1 | 5/2010 | Garcia-Martinez et al. | |
| 2011/0033419 A1 | 2/2011 | Aurellan et al. | |
| 2014/0309288 A1 * | 10/2014 | Brenner et al. | C12N 15/86 514/44 R |

FOREIGN PATENT DOCUMENTS

| | | |
|---|---|---|
| WO | 1992001070 A1 | 1/1992 |
| WO | 1993003769 A1 | 3/1993 |
| WO | 2007124573 A1 | 11/2007 |
| WO | 2013138463 A1 | 9/2013 |

OTHER PUBLICATIONS

Fernandes-Alnemri et al. (2007) "The pyroptosome: a supramolecular assembly of ASC dimers mediating inflammatory cell death via caspase-1 activation" Cell Death and Differentiation, 14, 1590-1604. (Year: 2007).*
Sordillo et al. (1981) "Malignant schwannoma—clinical characteristics, survival, and response to therapy" Cancer, 47(10), 2503-2509. (Year: 1981).*
Agarwal et al. "Cannabinoids mediate analgesia largely via peripheral type 1 cannabinoid receptors in nociceptors." Nat. Neurosci. 10(7): 870-879 (2007).
Antinheimo et al. "Population-based analysis of sporadic and type 2 neurofibromatosis-associated meningiomas and schwannomas." Neurology 54(1): 71-76 (2000).
Balaj et al. "Tumor microvesicles contain retrotransposon elements and amplified oncogene sequences."Nat Commun 2(180): 1-19 (2011).
Baser et al. "Increasing the specificity of diagnostic criteria for schwannomatosis." Neurology 66: 730-732 (2006).
Bowers et al. "Genetic therapy for the nervous system." Human Molecular Genetics 20(1): R28-R41 (2011).
Broekman et al. "Adeno-associated virus vectors serotyped with AAV8 capsid are more efficient than AAV-1 or -2 serotypes for widespread gene delivery to the neonatal mouse brain." Neuroscience 138(2): 501-510 (2006).
Brown et al. "Multiple regulatory elements control transcription of the peripheral myelin protein zero gene." J. Biol. Chem. 272(46): 28939-28947 (1997).
Carter. "Adeno-associated virus vectors." Current Opinion in Biotechnology 3(5): 533-539 (1992).

(Continued)

*Primary Examiner* — Teresa E Knight
*Assistant Examiner* — James Joseph Graber
(74) *Attorney, Agent, or Firm* — Nixon Peabody LLP; David S. Resnick; Nicole D. Kling

(57) ABSTRACT

Described herein are methods and compositions relating to the treatment of a tumor (e.g., schwannoma) by increasing expression of Apoptosis-associated Speck-like protein containing a CARD (ASC) and/or gasdermin D. In some embodiment, the increased expression is provided by means of a vector or construct comprising a nucleic acid encoding Apoptosis-associated Speck-like protein containing a CARD (ASC) and/or gasdermin D operably linked to a Schwann-lineage cell-specific promoter. In some embodiments, the vector is a viral vector.

21 Claims, 27 Drawing Sheets

Specification includes a Sequence Listing.

(56) References Cited

OTHER PUBLICATIONS

Chen et al. "Loss of modifier of cell adhesion reveals a pathway leading to axonal degeneration." J. Neurosci. 29(1): 118-130 (2009).

Chiorini et al. "Cloning of adeno-associated virus type 4 (AAV4) and generation of recombinant AAV4 particles." J. Virol. 71(9): 6823-6833 (1997).

Colunga et al. "The HSV-2 mutant PK induces melanoma oncolysis vis non-redundant death programs and associated with autophagy and pyroptosis protein." Gene Ther. 17(3): 315-327 (2010).

Di Stasi et al. "Inducible apoptosis as a safety switch for adoptive cell therapy." N. Engl. J. Med. 365(18): 1673-1683 (2011).

Eberling et al. "Results from a phase I safety trial of hAADC gene therapy for Parkinson disease." Neurology 70: 1980-1983 (2008).

Friedlander. "Role of caspase 1 in neurologic disease." Arch. Neurol. 57(9): 1273-1276 (2000).

Furlan et al. "Caspase-1 regulates the inflammatory process leading to autoimmune de-myelination." J. Immunol. 163(5): 2403-2409 (1999).

Gao et al. "Clades of Adeno-associated viruses are widely disseminated in human tissues." J. Virol. 78(12): 6381-6388 (2004).

Gao et al. "Novel adeno-associated viruses from rhesus monkeys as vectors for human gene therapy." Proc. Natl. Acad. Sci. USA 99(18): 11854-11859 (2002).

Gray et al., "Optimizing promoters for recombinant adeno-associated virus-mediated gene expression in the peripheral and central nervous system using self-complementary vectors." Hum. Gene Ther. 22(9): 1143-1153 (2011).

Hadfield et al. "Molecular characterisation of SMARCB1 and NF2 in familial and sporadic schwannomatosis." J. Med. Genet. 45(6): 332-339 (2008).

Hauck et al. "Characterization of tissue tropism determinants of adeno-associated virus type 1."Journal of Virology 77(4): 2768-2774 (2003).

Homs et al. "Schwann cell targeting via intrasciatic injection of AAV8 as gene therapy strategy for peripheral nerve regeneration." Gene Therapy 18(6): 622-630 (2011).

Huang et al. "Management of patients with schwannomatosis: Report of six cases and review of the literature." Surg. Neurol. 62(4): 353-361 (2004).

Hulsebos et al. "Germline mutation of INI1/SMARCB1 in familial schwannomatosis." Am. J. Hum. Genet. 80(4): 805-810 (2007).

Hung et al. "Establishment and characterization of a schwannoma cell line from a patient with neurofibromatosis 2." Int. J. Oncol. 20(3): 475-482 (2002).

Jacoby et al. "Molecular analysis of the NF2 tumor-suppressor gene in schwannomatosis." Am. J. Hum. Genet. 61(6): 1293-1302 (1997).

Jessen et al. "The origin and development of glial cells in peripheral nerves." Nat. Rev. Neurosci. 6(9): 671-682 (2005).

Juan et al. "Molecular characterization of mouse and rat CPP32 beta gene encoding a cysteine protease resembling interleukin-1 beta converting enzyme and CED-3." Oncogene 13(4): 749-755 (1996).

Kaplitt et al. "Safety and tolerability of gene therapy with an adeno-associated virus (AAV) borne GAD gene for Parkinson's disease: an open label, phase I trial." Lancet 369: 2097-2105 (2007).

Kirschbaum et al. "Rotarod impairment: Catalepsy-like screening test for antipsychotic side effects." Int. J. Neurosci. 119(10): 1509-1522 (2009).

Kotin. "Prospects for the use of adeno-associated virus as a vector for human gene therapy." Human Gene Therapy 5(7): 793-801 (1994).

Lamkanfi et al. "Inflammasomes: guardians of cytosolic sanctity." Immunological Reviews 227: 95-105 (2009).

Lebkowski et al. "Adeno-associated virus: a vector system for efficient introduction and integration of DNA into a variety of mammalian cell types." Molec. Cell. Biol. 8(10): 3988-3996 (1988).

Lee et al. "P0 is constitutively expressed in the rat neural crest and embryonic nerves and is negatively and positively regulated by axons to generate non-myelin-forming and myelin-forming Schwann cells." Mol. Cell. Neurosci. 8(5): 336-350 (1997).

Lentz et al. "Viral vectors for gene delivery to the central nervous system." Neurobiol. Dis. 48(2): 179-188 (2012).

Li et al. "Adeno-Associated Virus Vectors: Potential Applications for Cancer Gene Therapy." Cancer Gene Ther. 12(12): 913-925 (2005).

Lu-Emerson et al. "The neurofibromatosis. Part 2: NF2 and schwannomatosis." Rev. Neurol. Dis. 6(3): E81-E86 (2009).

Maitituoheti et al. "Adeno-associated virus-mediated local delivery of Light suppresses tumorigenesis in a murine cervical cancer model." J. Immunother. 34(8): 581-587 (2011).

McCarty et al. "Adeno-associated virus terminal repeat (TR) mutant generates self-complimentary vectors to overcome the rate-limiting step to transduction in vivo." Gene Ther. 10(26): 2112-2118 (2003).

McCarty. "Self-complimentary AAV vectors; advances and applications." Molecular Therapy 16(10): 1648-1656 (2008).

McClatchey et al. "Membrane organization and tumorigenesis—the NF2 tumor suppressor, Merlin." Genes & Development 19(19): 2265-2277 (2005).

McCown. "Adeno-associated virus (AAV) vectors in the CNS." Curr. Gene Ther. 11(3): 181-188 (2011).

McPhee et al. "Immune responses to AAV in a phase I study for Canavan disease." The Journal of Gene Medicine 8: 577-588 (2006).

Meijer et al. "Controlling brain tumor growth by intraventricular administration of an AAV vector encoding IFN-f3." Cancer Gene Ther. 16(8): 664-671 (2009).

Miao et al. "Caspase-1-induced pyroptotic cell death." Immunol. Rev. 243(1): 206-214 (2011).

Murmatsu et al. "Nucleotide sequencing and generation of an infectious clone of adeno-associated virus 3." Virology 221(1): 208-217 (1996).

Murphy et al. "Classification and nomenclature of viruses: sixth report of the International Committee on Taxonomy of Viruses." Arch. Virol. 1995: 169-175 (1995).

Muzyczka. "Use of adeno-associated virus as a general transduction vector for mammalian cells." Curr Top Microbiol Immunol 158: 97-129 (1992).

Parks et al. "Seroepidemiological and ecological studies of ther adenovirus-associated satellite viruses." J. Virol. 2 (6): 716-722 (1970).

Prabhakar et al. "Imaging and therapy of experimental schwannomas using HSV amplicon vector-encoding apoptotic protein under Schwann cell promoter." Cancer Gene Ther. 17(4): 266-274 (2010).

Prabhakar et al. "Regression of Schwannoman Induced by Adeno-Associated Virus-Mediated delivery of Caspase-1" Human Gene Therapy 24(2): 1-11 (2013).

Conway et al., "TMS1, a novel proapoptotic caspase recruitment domain protein, is a target of methylation-induced gene silencing in human breast cancers." Cancer research 60(22): 6236-6242 (2000).

Das et al., "Methylation mediated silencing of TMS1/ASC gene in prostate cancer." Molecular Cancer 5(28): 1-10 (2006).

Dhillon et al., "The contribution of genetic and epigenetic changes in granulosa cell tumors of ovarian origin." Clinical Cancer Research 10(16): 5537-5545 (2004).

Fernandes-Alnemri et al., "The pyroptosome: a supramolecular assembly of ASC dimers mediating inflammatory cell death via caspase-1 activation." Cell Death and Differentiation 14(9): 1590-1604 (2007).

Guan et al., "ASC/TMS1, a caspase-1 activating adaptor, is downregulated by aberrant metylation in human melanoma." International Journal of Cancer 107(2) :202-208 (2003).

Levine et al., "Effects of methylation on expression of TMS1/ASC in human breast cancer cells." Oncogene 22(22): 3475-3488 (2003).

Masumoto et al., "ASC is an activating adaptor for NF-κB and caspase-8-dependent apoptosis." Biochemical and Biophysical Research Communications 303(1): 69-73 (2003).

McConnell et al. "Activation of a caspase-9-mediated apoptotic pathway by subcellular redistribution of the novel caspase recruitment domain protein TMS1." Cancer Research 60(22): 6243-6247 (2000).

McConnell et al., "TMS1/ASC: the cancer connection." Apoptosis 9(1): 5-18 (2004).

(56) References Cited

OTHER PUBLICATIONS

Ramachandran et al., "Methylation-mediated silencing of TMS1 in pancreatic cancer and its potential contribution to chemosensitivity." Anticancer Research 30(10): 3919-3925 (2010).
Stone et al., "Aberrant methylation and down-regulation of TMS1/ASC in human glioblastoma." The American Journal of Pathology 165(4): 1151-1161 (2004).
Tamandani et al., "CpG island methylation of TMS1/ASC and CASP8 genes in cervical cancer." European Journal of Medical Research 14(2): 71-75 (2009).
Terasawa et al., "Epigenetic inactivation of TMS1/ASC in ovarian cancer." Clinical Cancer Research 10(6): 2000-2006 (2004).
Zhang et al., "Transcriptional silencing of the TMS1/ASC tumour suppressor gene by an epigenetic mechanism in hepatocellular carcinoma cells." The Journal of Pathology 212(2): 134-142 (2007).
Prabhakar et al. "Treatment of implantable NF2 schwannoma tumor models with oncolytic herpes simplex virus G47D." Cancer Gene Therapy 14(5): 460-467 (2007).
Rouleau et al. "Alteration in a new gene encoding a putative membrane-organizing protein causes neuro-fibromatosis type 2." Nature 363(6429): 515-521 (1993).
Rutledge et al. "Infectious clones and vectors derived from adeno-associated virus (AAV) serotypes other than AAV type 2." J. Virol. 72(1): 309-219 (1998).
Samulski. "Adeno-associated virus: integration at a specific chromosomal locus." Curr. Opin. Genet. Dev. 3(1): 74-80 (1993).
Samulski et al. "Cloning of adeno-associated virus into pBR322: Rescue of intact virus from the recombinant plasmid in human cells." Proc. Natl. Acad. Sci. USA 79(6): 2077-2081 (1982).
Saydam et al. "A novel imaging-compatible sciatic nerve schwannoma model." J. Neurosci. Methods 195(1): 75-77 (2011).
Shen et al. "Age-related changes in myelin morphology, electrophysiological property and myelin-associated protein expression of mouse sciatic nerves." Neurosci. Lett. 502(3): 162-167 (2011).
Tamai et al. "AAV-8 vector expressing IL-24 efficiently suppresses tumor growth mediated by specific mechanisms in MLL/AF4-positive ALL model mice." Blood 119(1): 64-71 (2012).
Tanaka et al. "Therapeutic Potential of HSP90 Inhibition for Neurofibromatosis Type 2." Clinical Cancer Research 19 (14): 3856-3870 (2013).
Taylor et al. "MicroRNA signatures of tumor-derived exosomes as diagnostic biomarkers of ovarian cancer." Gynecologic Oncology 110: 13-21 (2008).
Teschendorf et al. "Efficacy of recombinant adeno-associated viral vectors serotypes 1, 2, and 5 for the transduction of pancreatic and colon carcinmoa cells." Anticancer Research 30(6): 1931-1936 (2010).
Vincent et al. "Replication and packaging of HIV envelope genes in a novel adeno-associated virus vector system." Vaccine 90: 353-359 (1990).
Worgall et al. "Treatment of Late Infantile Neuronal Ceroid Lipofuscinosis by CNS Administration of a Serotype 2 Adeno-Associated Virus Expressing CLN2 cDNA." Human Gene Therapy 19: 463-474 (2008).
Sarkar et al. "Monocyte Derived Microvesicles Deliver a Cell Death Message via Encapsulated Capase-1." PLos One 4(9): e7140 1-9 (2009).

* cited by examiner

Human TMS1 genome

Fp →

GATATGGGTTTGTAGGAGATGGTCGGGTAGTTGTAGGCGGTTACGTATTAGGGTGAGTCGTTTTCGT
TTTTTTTTATTTCGTTTTTTTTTTTTATTTATATTAGCGTTTATTTCGCGGGTTTTTTCGTTTTTTGTTTTT
TTTATTTTAAATAAAGTTGTTTTATCGGAAAGGAGGTTTTTTACGTTTGGTTTATCGATTAACGGGAT
TTCGGTTTTACGGCGGGAAGGGAAGGGAAGGGGATTATTT

← Rp

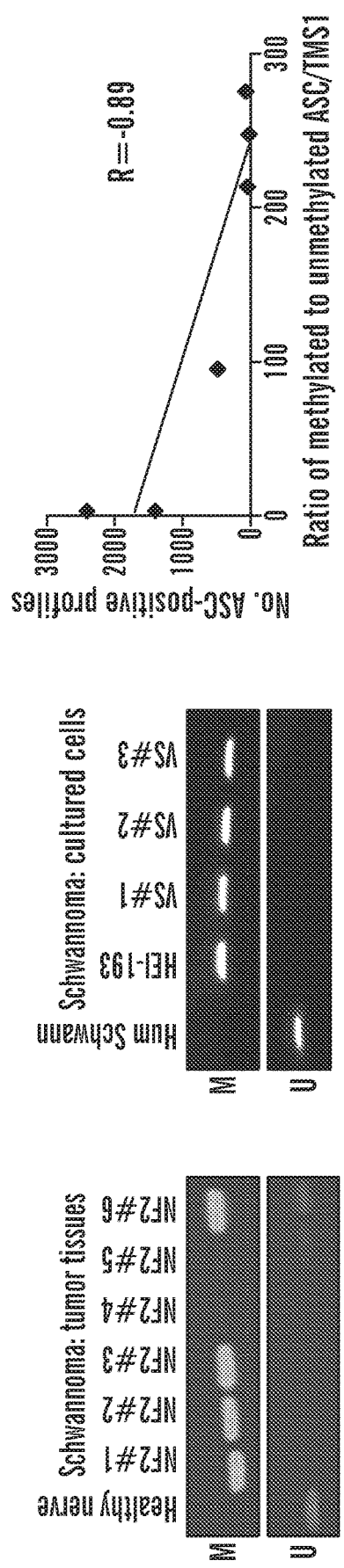
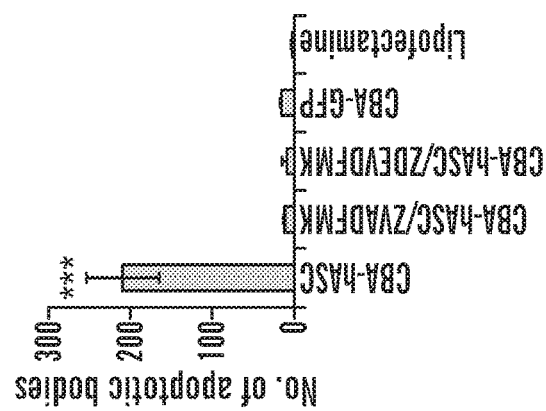
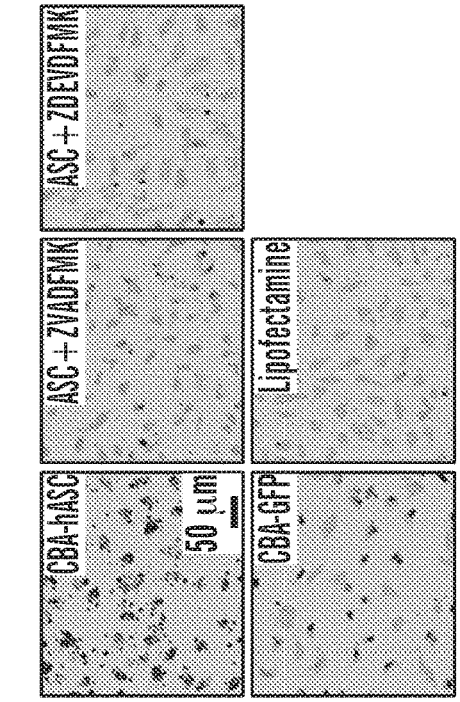

(H&E)

PBS

1E+8

1E+9

METHODS AND COMPOSITIONS RELATING TO THE TREATMENT OF TUMORS

CROSS-REFERENCE TO RELATED APPLICATIONS

This application claims benefit under 35 U.S.C. § 119(e) of U.S. Provisional Application No. 62/431,037 filed Dec. 7, 2016, the contents of which are incorporated herein by reference in their entirety.

GOVERNMENT SUPPORT

This application is a 35 U.S.C. § 371 National Phase Entry Application of International Application No. PCT/US2017/064809 filed Dec. 6, 2017, which designates the U.S. and claims benefit under 35 U.S.C. § 119(e) of U.S. Provisional Application No. 62/431,037 filed Dec. 7, 2016, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 1, 2017, is named 030258-088541-PCT SL.txt and is 25,654 bytes in size.

TECHNICAL FIELD

The technology described herein relates to methods and compositions for the treatment of tumors, e.g, schwannomas.

BACKGROUND

Schwannomas are tumors of Schwann cells lineage which cause pain, sensory/motor dysfunction, and death through compression of peripheral nerves, the spinal cord, and/or the brain stem. Neurofibromatosis 2 (NF2) and schwannomatosis originate in children or young adults and develop in multiple locations throughout life. Currently there is no efficient treatment for these tumors surgical resection is the main treatment approach but it is limited in scope and efficacy and has significant associated morbidity.

A complex multiprotein structure called the inflammasome is responsible for inducing apoptotic cell death and inflammatory responses. The inflammasome activates a subset of caspases known as the inflammatory caspases, such as caspase-1. When stimulated, inflammasomes assemble to represent the first line of host defense through proteolytic activation of caspase-1 which in turn maturates cytokines interleukin-1B and interleukin 18 and initiates an inflammatory cell death referred to as pyroptosis.

SUMMARY

It is demonstrated herein that ectopic expression of ASC and/or gasdermin D, components of the inflammasome, can induce inflammasome activation and/or apoptotic cell death in tumor cells. The inflammasome is a multiprotein structure responsible for: 1) inducing canonical caspase3/7 apoptosis, 2) inducing inflammatory cell death through pyroptosis, and 3) releasing immuno-stimulatory cytokines to the extracellular milieu. Thus, this pathway can not only induce death of cancer cells, but also establish a local "zone of resistance" or a systemic immune response that prevents formation of new tumors locally or distally. Successful activation of the inflammasome can therefore both treat existing tumors and prevent the formation of new tumors or tumor re-emergence after surgical resection.

Furthermore, as demonstrated herein, the ectopic expression of ASC and/or gasdermin D is notably more efficacious than direct expression of caspases themselves.

In one aspect of any of the embodiments, described herein is a method of treating a schwannoma in a subject in need thereof, the method comprising administering a viral vector comprising a nucleic acid encoding Apoptosis-associated Speck-like protein containing a CARD (ASC) and/or gasdermin D operably linked to a Schwann cell-specific promoter.

In one aspect of any of the embodiments, described herein is a method of inducing cell death of a target cell, the method comprising contacting the target cell with a nucleic acid encoding Apoptosis-associated Speck-like protein containing a CARD (ASC) and/or gasdermin D. In some embodiments of any of the aspects, the contacting step further comprises contacting the target cell with a viral vector comprising the nucleic acid encoding ASC and/or gasdermin D. In some embodiments of any of the aspects, the target cell is a neoplasm, cancer and/or tumor cell. In some embodiments of any of the aspects, the nucleic acid encoding ASC and/or gasdermin D is operably linked to a cell-type specific promoter or neoplasm, cancer and/or tumor cell-specific promoter. In some embodiments of any of the aspects, the contacting step comprises administering the nucleic acid to a subject comprising the target cell.

In one aspect of any of the embodiments, described herein is a method of treating a neoplasm or tumor in a subject in need thereof, the method comprising administering a viral vector comprising a nucleic acid encoding Apoptosis-associated Speck-like protein containing a CARD (ASC) and/or gasdermin D operably linked to a cell-type specific promoter or a neoplasm and/or tumor cell-specific promoter.

In some embodiments of any of the aspects, the subject in need of treatment for a schwannoma is a subject having or diagnosed as having a condition selected from the group consisting of: neurofibromatosis 1 (NF1); neurofibromatosis 2 (NF2); schwannomatosis; meningioma; nerve sheath tumor; schwannoma; vestibular schwannoma; sporadic schwannoma; neurofibrosarcoma; neurofibroma; neurofibromatosis (NF); malignant peripheral nerve sheath tumor; and a combination thereof.

In one aspect of any of the embodiments, described herein is a viral vector comprising a nucleic acid encoding Apoptosis-associated Speck-like protein containing a CARD (ASC) and/or gasdermin D gene and a Schwann cell-specific promoter. In some embodiments of any of the aspects, the Schwann cell specific promoter is upstream of the nucleic acid encoding ASC and/or gasdermin D.

In some embodiments of any of the aspects, the ASC and/or gasdermin D is a human, mouse, or rat ASC and/or gasdermin D. In some embodiments of any of the aspects, the Schwann cell-specific promoter is a P0, a peripheral myelin protein 22 (PMP22), or a MBP promoter. In some embodiments of any of the aspects, the promoter is a human or murine promoter. In some embodiments of any of the aspects, the viral vector is a recombinant adeno-associated virus (rAAV). In some embodiments of any of the aspects, the rAAV is of serotype AAV1 or AAV9. In some embodiments of any of the aspects, the rAAV is of serotype AAV1. In some embodiments of any of the aspects, the vector is a virus particle. In some embodiments of any of the aspects, the vector of any of claims 19-22, further comprising a polyadenylation signal. In some embodiments of any of the aspects, the polyadenylation signal is downstream of the nucleic acid encoding ASC and/or gasdermin D. In some embodiments of any of the aspects, the polyadenylation signal comprises a bovine growth hormone polyadenylation signal (BGHpA), a SV40 polyadenylation signal or a rabbit beta-globin polyadenylation signal. In some embodiments of any of the aspects, the vector further comprises a first AAV inverted terminal repeat (ITR) located upstream of the Schwann cell specific promoter and a second AAV ITR located downstream of the polyadenylation signal. In some embodiments of any of the aspects, the first or second AAV inverted terminal repeat comprises a deletion of the terminal resolution site. In some embodiments of any of the aspects, the vector is a polynucleotide. In some embodiments of any of the aspects, the vector is a single-stranded or double-stranded AAV. In some embodiments of any of the aspects, the vector is a self-complementary AAV (scAAV). In some embodiments of any of the aspects, the vector does not comprise a caspase gene.

In some embodiments of any of the aspects, the vector is administered directly to the neoplasm and/or tumor. In some embodiments of any of the aspects, the vector is administered by intratumoral injection. In some embodiments of any of the aspects, the vector is administered directly to a nerve affected by a schwannoma. In some embodiments of any of the aspects, administration is intranervously, intracranially, intratumorally, intramuscularly, intravenously, intradermally, or subcutaneously, or a combination thereof. In some embodiments of any of the aspects, the subject is also treated by surgical removal of the schwannoma and/or by gamma-knife radiosurgery. In some embodiments of any of the aspects, the subject is also treated with a pharmacological agent, e.g., a drug, biologic, or small molecule other than the vectors described herein. In some embodiments of any of the aspects, the subject is not administered a viral vector comprising a caspase gene.

In one aspect of any of the embodiments, described herein is a pharmaceutical composition comprising the viral vector as described herein and a pharmaceutically acceptable carrier. In one aspect of any of the embodiments, described herein is a kit comprising a composition comprising the viral vector as described herein, contained within packaging materials.

BRIEF DESCRIPTION OF THE DRAWINGS

FIG. 2A discloses SEQ ID NO: 22. The amplification product was sub-cloned and sequenced. Each row represents an individual sub-clone (FIG. 2B). Open circles, unmethylated CpG sites; closed circles, methylated CpGs.

FIGS. 15A-15G demonstrate that ASC expression is decreased in schwannomas and this correlates to promoter methylation. FIG. 15A depicts representative immunohistochemical staining of human schwannoma specimens and healthy peripheral nerve. There is strong staining for ASC in the healthy nerve (upper panels), while in schwannomas ASC immunoreactivity is either absent (NF2 #1, 2, 3) or substantially less than that in healthy nerve (NF2 #4, 5, 6). FIG. 15B depicts a graph of quantification of ASC immunostaining demonstrates greater numbers of ASC-positive cellular profiles in the normal nerve compared with schwannoma samples. FIG. 15C depicts a graph of quantitative RT-PCR analysis of ASC expression profile in human schwannomas shows that ASC expression is downregulated in schwannomas with methylated ASC. FIG. 15D depicts a graph of quantitative RT-PCR analysis demonstrates that ASC expression in human Schwann cells, human HEI-193 schwannoma cell line, and human primary schwannoma cells is downregulated in cells with methylated ASC. FIG. 15E demonstrates ASC methylation as determined by methylation specific PCR analysis of bisulfite-modified gDNA which showing complete ASC methylation in the samples with absent ASC staining (NF2 #1, 2, 3), and partial unmethylated pattern in schwannomas with depressed but present ASC protein expression (NF2 #4, 5, 6). Healthy human nerve shows completely unmethylated ASC. FIG. 15F depicts a methylation assay of ASC in cell lines (HEI-193 and three primary schwannomas lines) which demonstrates that ASC is fully methylated in cultured schwannoma cells but completely unmethylated human Schwann cells. FIG. 15G depicts a correlation chart showing that the downregulated schwannoma ASC protein expression levels are directly related to degree of methylation. (Quantitative PCR data are normalized to 18S gene and presented as fold increase, M: primers for methylated ASC, U; primers for unmethylated ASC.)

FIGS. 16A-16E demonstrate that ASC overexpression increases cell death in schwannoma cells. FIGS. 16A and 16B depict in vitro apoptotic body staining of HEI-193 (FIG. 16A) and 08031-9 (FIG. 16B) cells after transfection with pAAV-CBA-hASC plasmid shows obvious, brown-stained apoptotic bodies (arrows). Apoptosis was abolished in presence of a pan-caspase inhibitor or caspase-3 inhibitor compared with cells transfected with pAAV-CBA-GFP or exposed only to lipofectamine. Counting of apoptotic bodies revealed a significant increase in apoptosis after overexpression of ASC in transfected cells. FIG. 16C depicts Western blotting of HEI-193 cell lysates 24 h after transfection with pAAV-CBA-hASC plasmid, pAAV-CBA-GFP plasmid, or lipofectamine only treated cells showed that ASC overexpression was associated with cleavage of caspase-9, caspase-3 and increased BID (black arrows point to bands corresponding to the cleaved, active forms of caspases 9 and 3). FIG. 16D demonstrates that quantification of Western blot results demonstrated significant increases in cleaved (active) caspases-9 and -3, and in BID in ASC overexpressing cells compared with control-treated cells. FIG. 16E depicts a colorimetric assay which demonstrated significantly increased caspase-3/7 and caspase-9 activity in ASC over-expressing HEI-193 human schwannoma cells compared with controls. Data are presented as means±SEM (n=3). *p<0.05 (t-test). FIGS. 16A and 16B disclose SEQ ID NO: 13 as "DEVD".

FIG. 17A depicts immunohistochemical staining for the proliferation marker Ki67 was lower in tumors injected with AAV1-rP0-hASC (i) when compared to the expression level in the tumors injected with AAV-rP0-null (ii). Tumors injected with AAV1-rP0-hASC showed an increased rate of intra-tumoral apoptosis (brown stained, iii) while few scant apoptotic bodies were observed in AAV-rP0-null injected tumors (iv). AAV1-rP0-hASC injected tumors showed elevated expression of caspase-3 (v) and caspase-9 (vii) in comparison to AAV1-rP0-null injected tumors (vi, viii). FIG. 17B depicts quantification of Ki67-positive cells and apoptotic bodies and Ki67-positive cells, demonstrating less proliferation and greater apoptosis in the tumors injected with AAV1-rP0-hASC in comparison to tumors injected with AAV1-rP0-null. FIG. 17C depicts western blotting which revealed ASC expression in sciatic nerves of mice injected with AAV1-rP0-hASC (proteins extracted one week post virus injection). Data are presented as means±SEM (n=3). *p<0.05 (t-test).

FIG. 21A depicts transfection of mouse plexiform neurofibroma cell line with AAV plasmids encoding GFP driven by CBA promoter. Transfection was performed by lipofection and pictures were captured 24 hours post transfection. These results indicate moderate to low transduction. In FIG. 21B, LDH release was measured 24 hours after transfection with different AAV plasmids encoding mASC, mGASD-d-N, mICE (caspase-1), and GFP, as well as lipofectamine treated cells. "m" refers to mouse, the species from which the transgene was derived.

FIG. 22A depicts transfection of the cells with AAV plasmids encoding GFP driven by CBA promoter. Transfection was performed by lipofection and pictures were captured 24 hours post transfection. These results indicate moderate to low transduction. In FIG. 22B, LDH release was measured 24 hours after transfection with different AAV plasmids encoding mASC, mGASD-d-N, mICE (caspase-1), and GFP, as well as lipofectamine treated cells. "m" refers to mouse, the species from which the transgene was derived.

FIG. 23A depicts transfection of the cells with AAV plasmids encoding GFP driven by CBA promoter. Transfection was performed by lipofection and pictures were captured 24 hours post transfection. These results indicate moderate to low transduction. In FIG. 23B, LDH release was measured 24 hours after transfection with different AAV plasmids encoding mASC, mGASD-d-N, mICE (caspase-1), and GFP, as well as lipofectamine treated cells. "m" refers to mouse, the species from which the transgene was derived.

FIG. 24A demonstrates that ASC promoter is completely methylated in S462. TY cells (Human MPNST, NF1 deficient) and that ASC promoter is completely unmethylated in STS-26T cells (Human sporadic MPNST, NF1 proficient). Positive control for ASC promoter methylation ("HEI-193" cell line). Positive control for unmethylated ASC promoter (human schwann cells—"Sch"). FIG. 24B demonstrates that ASC mRNA is suppressed in cells with methylated ASC-promoter (HEI-193 and S462. TY).

DETAILED DESCRIPTION

Figures 9, 10:
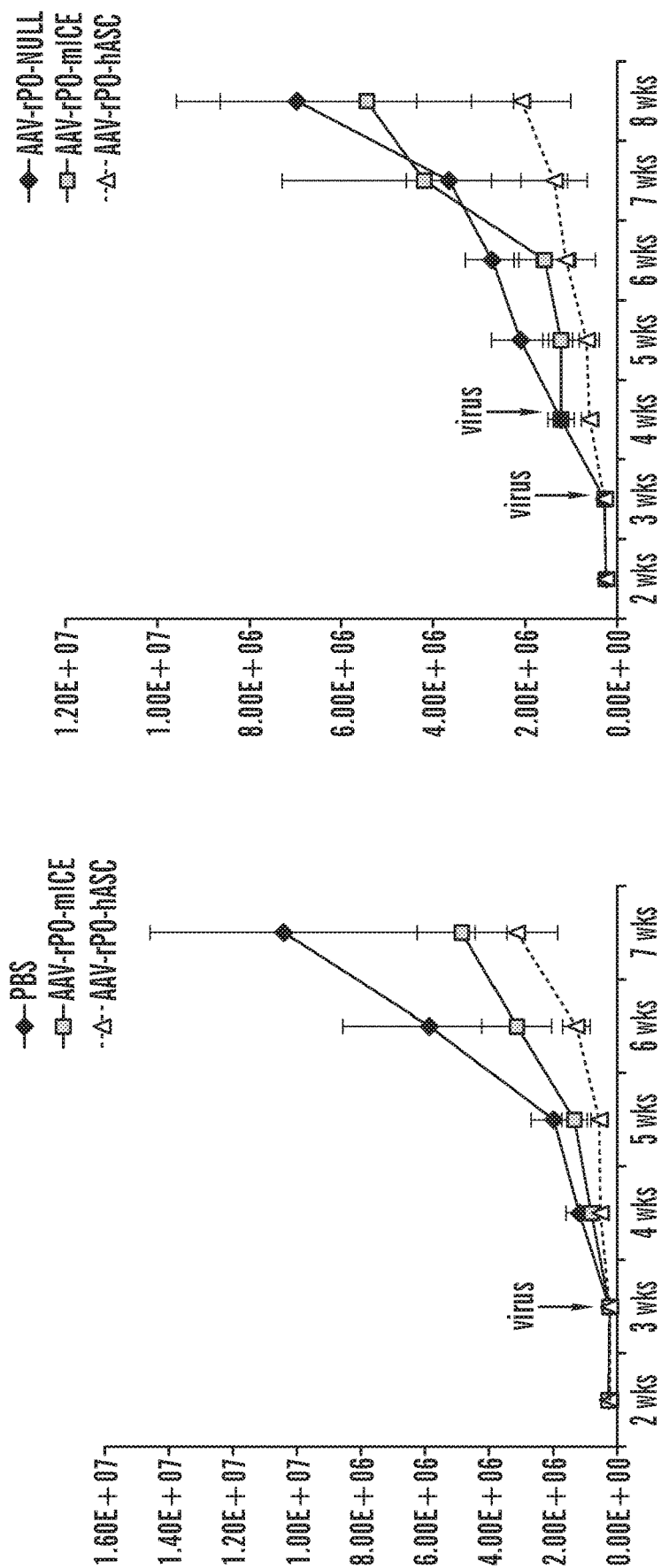
FIG. 9 depicts a graph demonstrating that ANOVA indicated a significant effect of AAV-P0-ASC compared to PBS without an interaction by time (following virus/PBS injection). There was no significant effect of AAV-P0-ICE compared with PBS. Abscissa—time following tumor implantation. Ordinate—bioluminescence signal (measure of tumor burden).
FIG. 10 depicts a graph demonstrating that ANOVA indicated a significant effect of AAV-P0-ASC compared to AAV-P0-null without an interaction by time (following virus injection). There was no significant effect of AAV-P0-ICE compared with AAV-P0-null. Abscissa—time following tumor implantation. Ordinate—bioluminescence signal (measure of tumor burden).

As described herein, the inventors have discovered that ectopic expression of Apoptosis-associated Speck-like protein containing a CARD (ASC) and/or gasdermin D in tumor cells (e.g., schwannomas) induces cell death of the tumor cells, but not of healthy cells. Moreover, the effectiveness of this approach is surprisingly superior to prior art methods such as, e.g., ectopic expression of caspases (see, e.g., FIG. 10). Without wishing to be bound by theory, it is contemplated herein that the superior results obtained with ASC and gasdermin D may be due to 1) as demonstrated herein, ASC has a broader function in cells as it activates multiple caspases, including those that do not belong to the inflammasome, such as caspases-3, and 2) as demonstrated herein, both ASC and Gasdermin D have a role as tumor suppressors, which is not reported for caspase-1.

Accordingly, in one aspect of any of the embodiments, provided herein is a method of inducing cell death of a target cell, the method comprising contacting the target cell with a nucleic acid encoding Apoptosis-associated Speck-like protein containing a CARD (ASC) and/or gasdermin D. In one aspect of any of the embodiments, provided herein is a method of treating a neoplasm and/or tumor in a subject in need thereof, the method comprising administering a vector comprising a nucleic acid encoding Apoptosis-associated Speck-like protein containing a CARD (ASC) and/or gasdermin D operably linked to a cell-type specific promoter or a neoplasm/tumor cell-specific promoter. In one aspect of any of the embodiments, provided herein is a method of treating a neoplasm and/or tumor in a subject in need thereof, the method comprising administering a viral vector comprising a nucleic acid encoding Apoptosis-associated Speck-like protein containing a CARD (ASC) and/or gasdermin D operably linked to a cell-type specific promoter or a neoplasm/tumor cell-specific promoter.

As used herein, "Apoptosis-associated Speck-like protein containing a CARD" or "ASC" or "PYCARD" refers to a protein comprising a N-terminal PYD domain and a C-terminal CARD domain which are both protein-protein interaction domains. ASC mediates the formation of the inflammasome and is an activator of pro-apoptotic pathways. Sequences for ASC are known for a number of species, e.g., human ASC (NCBI Gene ID No: 29108) mRNA (SEQ ID NO: 1; NCBI Ref Seq: NM_013258.4 and SEQ ID NO: 2; NCBI Ref Seq: NM_145182.2) and polypeptide (SEQ ID NO: 3; NCBI Ref Seq: NP_037390.2 and SEQ ID NO: 4; NCBI Ref Seq: NP_660183.1) as well as mouse ASC (NCBI Gene ID No: 66824) and rat ASC (NCBI Gene ID No: 282817). In some embodiments of any of the aspects, ASC can be human ASC, mouse ASC or rat ASC.

As used herein, "gasdermin D" refers to a polypeptide which is cleaved by activated caspases (e.g., after Asp275 of human gasdermin D and Asp276 of mouse gasdermin D). The resulting amino-terminal fragment then mediates, e.g., pyroptosis and cytokine release. Sequences for gasdermin D are known for a number of species, e.g., human gasdermin D (NCBI Gene ID No: 79792) mRNA (SEQ ID NO: 5; NCBI Ref Seq: NM_001166237.1 and SEQ ID NO: 6; NCBI Ref Seq: NM_024736.6) and polypeptide (SEQ ID NO: 7; NCBI Ref Seq: NP_079012.3) as well as mouse gasdermin D (NCBI Gene ID No: 69146) and rat gasdermin D (NCBI Gene ID No: 315084). In some embodiments of any of the aspects, gasdermin D can be human gasdermin D, mouse gasdermin D or rat gasdermin D.

In some embodiments of any of the aspects, gasdermin D can be the active N-terminal fragment of gasdermin D. For example, in some embodiments of any of the aspects a gasdermin D polypeptide does not comprise the C-terminal domain removed by caspase activity and/or a nucleic acid does not encode the C-terminal gasdermin D domain removed by caspase activity. Accordingly, in some embodiments of any of the aspects, a gasdermin D polypeptide can comprise a sequence corresponding to amino acids 1-275 of SEQ ID NO: 7. In some embodiments of any of the aspects, a gasdermin D polypeptide does not comprise a sequence corresponding to amino acids 276-484 of SEQ ID NO: 7. In some embodiments of any of the aspects, a nucleic acid as described herein encodes a gasdermin D polypeptide comprising a sequence corresponding to amino acids 1-275 of SEQ ID NO: 7. In some embodiments of any of the aspects, a nucleic acid as described herein does not encode a sequence corresponding to amino acids 276-484 of SEQ ID NO: 7.

In some embodiments of any of the aspects, a nucleic acid encoding ASC and/or gasdermin D can be delivered, provided, and/or administered by delivering, providing, and/or administering a viral vector comprising a nucleic acid encoding ASC and/or gasdermin D. In one aspect of any of the embodiments, provided herein is a vector comprising a nucleic acid encoding ASC and/or gasdermin D. In one aspect of any of the embodiments, provided herein is a viral vector comprising a nucleic acid encoding ASC and/or gasdermin D. In some embodiments of any of the aspects, the nucleic acid encodes both ASC and gasdermin D. In some embodiments of any of the aspects, the nucleic acid encodes ASC. In some embodiments of any of the aspects, the nucleic acid encodes gasdermin D.

In some embodiments of any of the aspects, the vector does not comprise a nucleic acid encoding a caspase.

In some embodiments of any of the aspects, the nucleic acid encoding ASC and/or gasdermin D is operably linked to a constitutive promoter. In some embodiments of any of the aspects, the nucleic acid encoding ASC and/or gasdermin D is operably linked to a cell-type specific promoter. In some embodiments of any of the aspects, the nucleic acid encoding ASC and/or gasdermin D is operably linked to a Schwann cell-specific promoter.

A nucleic acid molecule, such as DNA, is said to be capable of expressing a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides in recoverable amounts. The precise nature of the regulatory regions needed for gene expression may vary from organism to organism, as is well known in the analogous art.

In some embodiments of any of the aspects, the promoter can be upstream of the nucleic acid encoding ASC and/or gasdermin D.

A neoplasm, cancer and/or tumor cell-specific promoter is a promoter which is at least 1.5× more transcriptionally active in a neoplasm, cancer and/or tumor cell as compared to a healthy cell of the same type. In some embodiments of any of the aspects, a neoplasm, cancer and/or tumor cell-specific promoter is a promoter which is at least 1.5× e.g., 2×, 5×, 10× or more transcriptionally active in a neoplasm, cancer and/or tumor cell as compared to a healthy cell of the same type. Neoplasm, cancer and/or tumor cell-specific promoters are known for various types of cancers and tumors and one suitable for use in a given type of neoplasm, cancer or tumor is readily identified by one of skill in the art.

A cell type-specific promoter is a promoter which is at least 1.5× more transcriptionally active in a first cell type (either healthy or cancerous) as compared to other cell types. In some embodiments of any of the aspects, a cell type-specific promoter is a promoter which is at least 1.5× e.g., 2×, 5×, 10× or more transcriptionally active in a first cell type (either healthy or cancerous) as compared to other cell types. Cell type-specific promoters are known for various types of cells and one suitable for use in a given type of neoplasm, cancer or tumor is readily identified by one of skill in the art. In some embodiments of any of the aspects, the cell types-specific promoter is specific to Schwann cells and/or Schwann-lineage cells.

In some embodiments of any of the aspects, the vector can be a polynucleotide.

In some embodiments of any of the aspects, the viral vector can be a recombinant adeno-associated virus (rAAV). In some embodiments of any of the aspects, the rAAV can be of serotype AAV1 or AAV9. In some embodiments of any of the aspects, the vector can be a single-stranded or double-stranded AAV. In some embodiments of any of the aspects, the vector can be is a self-complementary AAV (scAAV). In some embodiments of any of the aspects, the vector can be a virus particle.

In some embodiments of any of the aspects, a vector can further comprise a polyadenylation signal. In some embodiments of any of the aspects, the polyadenylation signal can be downstream of the nucleic acid encoding ASC and/or gasdermin D. In some embodiments of any of the aspects, the polyadenylation signal comprises a bovine growth hormone polyadenylation signal (BGHpA), a SV40 polyadenylation signal or a rabbit beta-globin polyadenylation signal.

In some embodiments of any of the aspects, the vector can further comprise a first AAV inverted terminal repeat (ITR) located upstream of the promoter and a second AAV ITR located downstream of the polyadenylation signal. In some embodiments of any of the aspects, the first or second AAV inverted terminal repeat comprises a deletion of the terminal resolution site.

In some embodiments of any of the aspects, the neoplasm and/or tumor to be treated is a schwannoma and the promoter is a schwann-cell specific promoter. Non-limiting examples of schwann-cell specific promoters are known in the art and can include a P0 promoter (e.g., human P0 (NCBI Gene ID: 4359), mouse P0 (NCBI Gene ID: 17528), or rat P0 (NCBI Gene ID: 24564)), a peripheral myelin protein 22 promoter (PMP22) (e.g., human PMP22 (NCBI Gene ID: 5376), mouse PMP22 (NCBI Gene ID: 18858), or rat PMP22 (NCBI Gene ID: 24660)), or a MBP promoter (e.g., human MBP (NCBI Gene ID: 155), mouse MBP (NCBI Gene ID: 17196), or rat MBP (NCBI Gene ID: 24547)) promoter.

In various embodiments, the Schwann cell specific promoter can be a human, mouse, or rat promoter (e.g., human P0 promoter, human PMP22 promoter, human MBP promoter, mouse P0 promoter, mouse PMP22 promoter, mouse MBP promoter, rat P0 promoter, and rat PMP22 promoter, and rat MBP promoter or hybrids thereof). A non-limiting exemplary sequence of a rat P0 promoter is set forth in SEQ ID NO.: 8. A non-limiting exemplary sequence of a mouse P0 promoter is set forth in SEQ ID NO.: 9. A non-limiting exemplary sequence of a human P0 promoter is set forth in SEQ ID NO.: 10.

A non-limiting exemplary sequence of a human PMP22 promoter is set forth in SEQ ID NO.: 11. A non-limiting exemplary sequence of a human MBP promoter is set forth in SEQ ID NO.: 12.

In some embodiments of any of the aspects, the methods described herein relate to delivering, providing, and/or administering a nucleic acid encoding ASC. In some embodiments of any of the aspects, the methods described herein relate to delivering, providing, and/or administering vector comprising a nucleic acid encoding ASC. In some embodiments of any of the aspects, the methods described herein relate to delivering, providing, and/or administering viral vector comprising a nucleic acid encoding ASC. In some embodiments of any of the aspects, the methods described herein relate to delivering, providing, and/or administering a nucleic acid encoding gasdermin D. In some embodiments of any of the aspects, the methods described herein relate to delivering, providing, and/or administering viral vector comprising a nucleic acid encoding gasdermin D.

In some embodiments of any of the aspects, the methods described herein relate to delivering, providing, and/or administering a nucleic acid encoding ASC and gasdermin D. In some embodiments of any of the aspects, the methods described herein relate to delivering, providing, and/or administering viral vector comprising a nucleic acid encoding ASC and gasdermin D. In some embodiments of any of the aspects, the methods described herein relate to delivering, providing, and/or administering a single nucleic acid encoding both ASC and gasdermin D. In some embodiments of any of the aspects, the methods described herein relate to delivering, providing, and/or administering a single viral vector comprising a nucleic acid encoding both ASC and gasdermin D. In some embodiments of any of the aspects, the methods described herein relate to delivering, providing, and/or administering a first nucleic acid encoding ASC and a second nucleic acid encoding gasdermin D. In some embodiments of any of the aspects, the methods described herein relate to delivering, providing, and/or administering a first viral vector comprising a nucleic acid encoding ASC and a second viral vector comprising a nucleic acid encoding gasdermin D.

Various embodiments of the present invention provide a pharmaceutical composition. The pharmaceutical composition can comprise a vector comprising a nucleic acid encoding ASC and/or gasdermin D, or a cell transfected with the vector, or supernatant conditioned with the transfected cell, or an extracellular vesicle isolated from the transfected cell. Any of the foregoing compositions can be administered to a subject in need of treatment as described herein.

In some embodiments of any of the aspects, the target cell can be a neoplasm cell, tumor cell and/or cancer cell. In some embodiments of any of the aspects, the methods of treatment relate to inducing cell death of and/or inhibiting cell growth of a neoplasm, tumor or cancer cell.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

In one aspect of any of the embodiments, described herein is a method of treating a schwannoma in a subject in need thereof, the method comprising administering a viral vector comprising a nucleic acid encoding Apoptosis-associated Speck-like protein containing a CARD (ASC) and/or gasdermin D operably linked to a Schwann cell-specific promoter.

Schwannoma tumors are composed of Schwann-lineage cells and form along peripheral, spinal and cranial nerves. These tumors can cause pain, sensory/motor dysfunction, and death through compression of peripheral nerves, the spinal cord, and/or the brain stem. Multiple schwannomas in peripheral distal and intracranial nerves are the hallmark of neurofibromatosis 1 and 2 (NF1 and NF2), and schwannomatosis, three types of nerve sheath tumors. Schwannomas are benign tumors composed of neoplastic dedifferentiated Schwann cells. Although typically nonmalignant and slow growing, these tumors can have devastating consequences for patients. They can cause extreme pain and compromise sensory/motor functions, including hearing and vision. Schwannomas in NF2 are frequently associated with neurological deficits, such as paresthesias, weakness, or hearing loss, and similar tumors in schwannomatosis often cause excruciating pain. Some schwannomas become very large, causing compression of adjacent organs or structures, and can lead to paralysis or death due to progressive spinal cord or brainstem compression. Schwannomas may arise sporadically, without presenting any genetic features of NF1, NF2 and schwannomatosis. Most vestibular schwannomas are sporadic schwannomas, so their incidence is very significant. Vestibular schwannomas usually occur as single tumors, not as multiple tumors throughout the body. In some embodiments of any of the aspects, a subject in need of treatment for a schwannoma can be a subject having or diagnosed as having a condition selected from the group consisting of: neurofibromatosis 1 (NF1); neurofibromatosis 2 (NF2); schwannomatosis; meningioma; nerve sheath tumor; schwannoma; vestibular schwannoma; sporadic schwannoma; neurofibrosarcoma; neurofibroma; neurofibromatosis (NF); malignant peripheral nerve sheath tumor; and a combination thereof.

The standard of care for patients with NF2 and schwannomatosis is surgical resection or radiosurgery of symptomatic tumors to reduce tumor size. Unlike in the case of sporadic schwannomas, in which typically only a single tumor is present and surgery is generally an efficacious treatment strategy as long as the lesion is accessible for resection, in schwannomatosis and NF2, which present with multiple tumors, resection is confounded by both the inaccessibility of many tumors and by risk of nerve damage, including major motor dysfunction, significant sensory loss (including deafness in the case of NF2 vestibular schwannomas), and neuropathic pain. Thus, for most individuals there is substantial morbidity associated with schwannomas in both NF2 and schwannomatosis, as well as with the current therapies. This suffering and debility, in combination with the paucity of therapeutic options, makes the treatment of schwannomas a major unmet medical need.

In some embodiments, the methods described herein relate to treating a subject having or diagnosed as having a tumor or cancer with a vector and/or nucleic acid encoding ASC and/or gasdermin D. Subjects having cancer can be identified by a physician using current methods of diagnosing cancer. For example, symptoms and/or complications of schwannomas which characterize these conditions and aid in diagnosis are well known in the art and include but are not limited to, pain, swelling, hearing loss, loss of coordination and/or balance, muscle weakness, and numbness. Tests that may aid in a diagnosis of, e.g. schwannoma include, but are not limited to, CTs and MRI. A family history of schwnnoma or exposure to risk factors for schwannomas can also aid in determining if a subject is likely to have a schwannoma or in making a diagnosis of schwannoma.

The compositions and methods described herein can be administered to a subject having or diagnosed as having a neoplasm, tumor and/or cancer. In some embodiments, the methods described herein comprise administering an effective amount of compositions described herein, e.g. a vector encoding ASC and/or gasdermin D to a subject in order to alleviate a symptom of a neoplasm, tumor and/or cancer. As used herein, "alleviating a symptom" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Administration can be local or systemic.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection. In some embodiments of any of the aspects, the nucleic acid and/or vector can be administered directly to the tumor. In some embodiments of any of the aspects, the nucleic acid and/or vector can be administered by intratumoral injection. In some embodiments of any of the aspects, the nucleic acid and/or vector can be administered directly to a nerve affected by a schwannoma. In some embodiments of any of the aspects, the nucleic acid and/or vector can be administered intranervously, intracranially, intratumorally, intramuscularly, intravenously, intradermally, or subcutaneously, or a combination thereof.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular anti-tumor effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor growth and/or size among others. The dosage can be determined by a physician and adjusted, as necessary, to suit observed effects of the treatment.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

In some embodiments of any of the aspects, a method of treatment as described herein can further comprise surgical removal of a neoplasm or tumor, e.g., a schwannoma. In some embodiment of any of the aspects, a nucleic acid and/or vector as described herein can be administered before, concurrently with, or after surgical removal of a neoplasm or tumor, e.g., a schwannoma. Various treatment method of the present invention may further comprise treating the subject with surgery, radiation therapy, or chemotherapy, or a combination thereof.

In some embodiments of any of the aspects, a subject treated according to the methods described herein is not administered a viral vector comprising a caspase gene or a nucleic acid encoding a caspase. In some embodiments of any of the aspects, a subject treated according to the methods described herein is not administered a viral vector comprising a caspase gene or a nucleic acid encoding a caspase concurrently with the treatment as described herein. In some embodiments of any of the aspects, a subject treated according to the methods described herein has not been administered a viral vector comprising a caspase gene or a nucleic acid encoding a caspase. In some embodiments of any of the aspects, a nucleic acid and/or vector as described herein does not comprise a caspase gene.

In one aspect of any of the embodiments, provided herein is a pharmaceutical composition comprising 1) a nucleic acid encoding ASC and/or gasdermin D or a viral vector comprising a nucleic acid encoding ASC and/or gasdermin D and 2) a pharmaceutically acceptable carrier.

In some embodiments, the technology described herein relates to a pharmaceutical composition comprising a nucleic acid and/or vector as described herein, and optionally a pharmaceutically acceptable carrier. In some embodiments, the active ingredients of the pharmaceutical composition comprise a vector and/or nucleic acid encoding ASC and/or gasdermin D as described herein. In some embodiments, the active ingredients of the pharmaceutical composition consist essentially of a vector and/or nucleic acid encoding ASC and/or gasdermin D as described herein. In some embodiments, the active ingredients of the pharmaceutical composition consist of a vector and/or nucleic acid encoding ASC and/or gasdermin D as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a vector and/or nucleic acid encoding ASC and/or gasdermin D as described herein.

In some embodiments, the pharmaceutical composition comprising a vector and/or nucleic acid encoding ASC and/or gasdermin D as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a vector and/or nucleic acid encoding ASC and/or gasdermin D as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the vector and/or nucleic acid encoding ASC and/or gasdermin D can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In some embodiments of any of the aspect, the concentration of the vector is about $1\times10^7$-$1\times10^{12}$, $1\times10^7$-$1\times10^{10}$, $1\times10^{10}$-$1\times10^{12}$, $1\times10^{12}$-$1\times10^{15}$, or $1\times10^{15}$-$1\times10^{18}$ copies per µl of the pharmaceutical composition. In some embodiments of any of the aspect, the concentration of the rAAV vector is about $1\times10^7$-$1\times10^{12}$, $1\times10^7$-$1\times10^{10}$, $1\times10^{10}$-$1\times10^{12}$, $1\times10^{12}$-$1\times10^{15}$, or $1\times10^{15}$-$1\times10^{18}$ genome copies (gc) per µl of the pharmaceutical composition.

In certain embodiments, an effective dose of a composition comprising a vector and/or nucleic acid encoding ASC and/or gasdermin D as described herein can be administered to a patient once. In certain embodiments, an effective dose of a composition comprising a vector and/or nucleic acid encoding ASC and/or gasdermin D can be administered to a patient repeatedly. For systemic administration, subjects can be administered a therapeutic amount of a composition comprising a vector and/or nucleic acid encoding ASC and/or gasdermin D, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. neoplasm and/or tumor size and/or rate of growth by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition described herein can be administered over a period of time, such as over a 5 minute, 10 minute, 15 minute, 20 minute, or 25 minute period.

In some embodiments of any of the aspects, the dose of viral vectors as described herein, e.g., AAV1 vector comprising a human P0 promoter and human ASC gene, are provided at a dose of more than $1\times10^{\wedge}9$ gc (genome copies)/kg. In some embodiments of any of the aspects, the dose of viral vectors as described herein, e.g., AAV1 vector comprising a human P0 promoter and human ASC gene, are provided at a dose of from about $1.5\times10^{\wedge}9$ gc/kg to about $1.5\times10^{\wedge}11$ gc/kg. In some embodiments of any of the aspects, the dose of viral vectors as described herein, e.g., AAV1 vector comprising a human P0 promoter and human ASC gene, are provided at a dose of from $1.5\times10^{\wedge}9$ gc/kg to $1.5\times10^{\wedge}11$ gc/kg.

In some embodiments of any of the aspects, the dose of viral vectors as described herein, e.g., AAV1 vector comprising a human P0 promoter and human ASC gene, are provided at a dose of from about $1.5\times10^{\wedge}9$ gc/kg to about $1.5\times10^{\wedge}15$ gc/kg. In some embodiments of any of the aspects, the dose of viral vectors as described herein, e.g., AAV1 vector comprising a human P0 promoter and human ASC gene, are provided at a dose of from $1.5\times10^{\wedge}9$ gc/kg to $1.5\times10^{\wedge}15$ gc/kg. In some embodiments of any of the aspects, the dose of viral vectors as described herein, e.g., AAV1 vector comprising a human P0 promoter and human ASC gene, are provided at a dose of from about $1.5 \times 10^9$ gc/kg to about $1.5 \times 10^{19}$ gc/kg. In some embodiments of any of the aspects, the dose of viral vectors as described herein, e.g., AAV1 vector comprising a human P0 promoter and human ASC gene, are provided at a dose of from $1.5 \times 10^9$ gc/kg to $1.5 \times 10^{19}$ gc/kg.

In some embodiments of any of the aspects, the dose of viral vectors as described herein, e.g., AAV1 vector comprising a human P0 promoter and human ASC gene, are provided at a dose of from about $1.0 \times 10^{11}$ gc/kg to about $1.0 \times 10^{15}$ gc/kg. In some embodiments of any of the aspects, the dose of viral vectors as described herein, e.g., AAV1 vector comprising a human P0 promoter and human ASC gene, are provided at a dose of from $1.0 \times 10^{11}$ gc/kg to $1.0 \times 10^{15}$ gc/kg. In some embodiments of any of the aspects, the dose of viral vectors as described herein, e.g., AAV1 vector comprising a human P0 promoter and human ASC gene, are provided at a dose of from about $1.0 \times 10^{11}$ gc/kg to about $1.0 \times 10^{17}$ gc/kg. In some embodiments of any of the aspects, the dose of viral vectors as described herein, e.g., AAV1 vector comprising a human P0 promoter and human ASC gene, are provided at a dose of from $1.0 \times 10^{11}$ gc/kg to $1.0 \times 10^{17}$ gc/kg. In some embodiments of any of the aspects, the dose of viral vectors as described herein, e.g., AAV1 vector comprising a human P0 promoter and human ASC gene, are provided at a dose of from about $1.0 \times 10^{11}$ gc/kg to about $1.0 \times 10^{19}$ gc/kg. In some embodiments of any of the aspects, the dose of viral vectors as described herein, e.g., AAV1 vector comprising a human P0 promoter and human ASC gene, are provided at a dose of from $1.0 \times 10^{11}$ gc/kg to $1.0 \times 10^{19}$ gc/kg.

In some embodiments of any of the aspects, the dose of viral vectors as described herein, e.g., AAV1 vector comprising a human P0 promoter and human ASC gene, are provided at a dose of about $2.0 \times 10^{12}$ gc/kg. In some embodiments of any of the aspects, the dose of viral vectors as described herein, e.g., AAV1 vector comprising a human P0 promoter and human ASC gene, are provided at a dose of about $3.3 \times 10^{14}$ gc/kg.

In some embodiments of any of the aspects, the dose of viral vectors as described herein, e.g., AAV1 vector comprising a human P0 promoter and human ASC gene, are provided directly to a tumor or neoplasm in a volume of from about 5% to about 50% of the total tumor or neoplasm volume.

The dosage ranges for the administration of the compositions described herein, according to the methods described herein depend upon, for example, the form of the active ingredient, its potency, and the extent to which symptoms, markers, or indicators of a condition described herein are desired to be reduced, for example the percentage reduction desired for tumor size and/or rate of growth or the extent to which, for example, immunity is desired to be induced. The dosage should not be so large as to cause adverse side effects, such as auto-immune conditions. Generally, the dosage will vary with the age, condition, and sex of the patient and can be determined by one of skill in the art. The dosage can also be adjusted by the individual physician in the event of any complication.

The efficacy of a vector and/or nucleic acid encoding ASC and/or gasdermin D in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size and/or rate of growth. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of mouse models of cancer. When using an experimental animal model, efficacy of treatment is evidenced when a statistically significant change in a marker is observed, e.g. tumor size and/or rate of growth, or induction of inflammasome activity and/or tumor-cell apoptosis.

In vitro and animal model assays are provided herein which allow the assessment of a given dose of a vector and/or nucleic acid encoding ASC and/or gasdermin D. By way of non-limiting example, the effects of a dose of a vector and/or nucleic acid encoding ASC and/or gasdermin D can be assessed by administering the dose to a mouse in which HEI-193FC cells have been implanted in the sciatic nerve. Tumor growth can be assessed at by immunohistological staining and/or measuring pain responses, e.g., as described in the Examples herein.

In some embodiments of any of the aspects, the present invention provides provides a supernatant obtained from a culture of a cell transfected with a vector comprising a nucleic acid encoding ASC and/or gasdermin D. In some embodiments of any of the aspects, the cell is a schwannoma cell or a Schwann cell. In various embodiments, the transfected cell is cultured for about 12-24, 24-48, or 48-73 hours.

In some embodiments of any of the aspects, the present invention provides an extracellular vesicle isolated from a cell transfected with a vector comprising a nucleic acid encoding ASC and/or gasdermin D. In some embodiments of any of the aspects, the cell is a schwannoma cell or a Schwann cell. In various embodiments, the transfected cell is cultured for about 12-24, 24-48, or 48-73 hours.

In one aspect of any of the embodiments, provided herein is a composition comprising a nucleic acid encoding ASC and/or gasdermin D or a viral vector comprising a nucleic acid encoding ASC and/or gasdermin D, contained within packaging materials. The kit is an assemblage of materials or components, including at least one of the inventive vectors and/or compositions. The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals Instructions for use may be included in the kit. "Instructions for use" typically include a tangible expression describing the technique to be employed in using the components of the kit to affect a desired outcome, such as to treat, reduce the severity of, inhibit or prevent schwannoma in a subject. Still in accordance with the present invention, "instructions for use" may include a tangible expression describing the preparation of virions and/or at least one method parameter, such as the relative amounts of rAAV vector genome, dosage requirements and administration instructions, and the like, typically for an intended purpose. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition containing a volume of a vector described herein. The packaging material generally has an external label which indicates the contents and/or purpose of the kit and/or its components.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of neoplasms, cancer and/or tumors. A subject can be male or female.

A subject can be one who has been previously diagnosed with or identified as suffering from or having a condition in need of treatment (e.g. schwannoma) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. ability to reduce schwannoma growth and/or activate the inflammasome and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments, a nucleic acid encoding a polypeptide as described herein (e.g. ASC and/or gasdermin D) is comprised by a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene," that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

"rAAV vector" refers to any vector derived from any adeno-associated virus serotype, including, without limitation, AAV-1, AAV-2, AAV-3, AAV-4, AAV-5, AAV-7 AAV-8, AAV9, AAV10, AAV11, or AAV12, or a hybrid serotype thereof and the like. rAAV vectors can have one or more of the AAV wild-type genes deleted in whole or in part, preferably the Rep and/or Cap genes, but retain functional flanking ITR sequences. Functional ITR sequences are generally necessary for the rescue, replication, packaging and potential chromosomal integration of the AAV genome. Thus, a rAAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging.

"Recombinant virus" refers to a virus that has been genetically altered (e.g., by the addition or insertion of a heterologous nucleic acid construct into the particle).

"AAV virion" refers to a complete virus particle, such as a wild-type ("wt") AAV virus particle (i.e., including a linear, single-stranded AAV nucleic acid genome associated with an AAV capsid protein coat). In this regard, single-stranded AAV nucleic acid molecules of either complementary sense (i.e., "sense" or "antisense" strands) can be packaged into any one AAV virion; both strands are equally infectious. In addition, the AAV capsid protein coat can be from any of the various AAV serotypes depending on the target of the AAV virion.

A "recombinant AAV virion" or "rAAV virion" is defined herein as an infectious, replication-defective virus composed of an AAV protein shell, encapsidating a heterologous DNA molecule of interest (e.g., genes encoding caspase-1) which is flanked on both sides by AAV ITRs. A rAAV virion may be produced in a suitable host cell which has had an rAAV vector, AAV Rep and Cap functions and helper virus functions introduced therein. In this manner, the host cell is rendered capable of producing AAV replication and capsid proteins that are required for replicating and packaging the rAAV vector (i.e., containing a recombinant nucleotide sequence of interest) into recombinant virion particles for subsequent gene delivery. The complete transgene may consist of a promoter, the coding sequences, usually a cDNA and a polyadenylation signal. A transgene may also include regulatory sequences and intron regions. Promoters that would regulate transgene expression may include constitutive, inducible and tissue-specific promoters.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via any method of gene delivery, including replication-defective viral vectors, such as via a rAAV. For example, transduction could mean uptake of a virus, part of which is DNA.

Extracellular vesicles (EVs, including but are not limited to exosomes, microvesicles, microparticles, circulating microvesicles, shedding microvesicles, nanovesicles, nanoparticles, apoptotic bodies, and membrane vesicles) are fragments of plasma membrane ranging from for example, 20 nm to 10 µm, shed from almost all cell types. Microvesicles play a role in intercellular communication and can transport mRNA, miRNA, and proteins between cells. As will be apparent to a person of skill in the art, there are various EV isolation and purification protocols based on filtration, differential centrifugation, ultracentrifugation, flotation of vesicles in gradients (sucrose, OptiPrep™), and immunoaffinity capture utilizing antibodies against membrane proteins. Exemplary information for isolating extracelluar vesicles may be found in Simpson R J, Mathivanan S (2012) Extracellular Microvesicles: The Need for Internationally Recognised Nomenclature and Stringent Purification Criteria. J Proteomics Bioinform 5: ii-ii; van der Pol et al., Classification, functions, and clinical relevance of extracellular vesicles, Pharmacol Rev. 2012 July; 64(3):676-705; Raposo and Stoorvogel, Extracellular vesicles: exosomes, microvesicles, and friends, J Cell Biol. 2013 Feb. 18; 200(4):373-83; and Witwer et al., Standardization of sample collection, isolation and analysis methods in extracellular vesicle research, J Extracell Vesicles. 2013 May 27; 2, which are incorporated herein by reference in their entirety. Also, see Sarkar et al., 2009, Taylor and Gercel-Taylor, 2008, and Balaj et al., 2011, which are incorporated herein by reference in their entirety.

As a non-limiting example, a filtration-based method may be used and the type and size of filters and columns will be apparent to a person of skill in the art. For example, centrifugal ultracentrifugation devices covering sample volumes from 500 µl to 2 ml with any type of low-protein retentions and wide pH-range (e.g. 2-12 pH) filter membranes, such as polyethersulfone (PES) can be used. The nominal size of the pores can range between any one or more of 0.1 µm to 1 µm, 0.2 µm to 1 µm, 0.3 µm to 1 µm, 0.4 µm to 1 µm, 0.5 µm to 1 µm, 0.6 µm to 0.7 µm to 0.8 µm to 1 µm or 0.9 µm. In comparison with an ultra-centrifugation based protocol, in which extracellular vesicles (EV) are recovered from the supernatant after centrifugation at 10,000 g/30 min or 100,000 g/60 min, a filtration protocol can filter supernatant at 8,000 g/30 sec using Vivaspin ultrafiltration spin columns.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. a neoplasm, tumor or schwannoma. The term "treating" includes reducing or alleviating at least one adverse effect or symptom of a condition, disease or disorder associated with, e.g., a tumor. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art.

The term "statistically significant" or "significantly" refers to statistical significance and generally means a two standard deviation (2SD) or greater difference. In some embodiments, a statistically significant or significant difference refers to a p-value of less than 0.05.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating a schwannoma in a subject in need thereof, the method comprising administering a viral vector comprising a nucleic acid encoding Apoptosis-associated Speck-like protein containing a CARD (ASC) and/or gasdermin D operably linked to a Schwann cell-specific promoter.
2. A method of inducing cell death of a target cell, the method comprising contacting the target cell with a nucleic acid encoding Apoptosis-associated Speck-like protein containing a CARD (ASC) and/or gasdermin D.
3. The method of paragraph 2, wherein contacting step further comprises contacting the target cell with a viral vector comprising the nucleic acid encoding ASC and/or gasdermin D.
4. The method of any of paragraphs 2-3, wherein the target cell is a cancer and/or tumor cell.
5. The method of paragraph 4, wherein the nucleic acid encoding ASC and/or gasdermin D is operably linked to a cancer and/or tumor cell-specific promoter.
6. The method of any of paragraphs 2-5, wherein the contacting step comprises administering the nucleic acid to a subject comprising the target cell.
7. A method of treating a tumor in a subject in need thereof, the method comprising administering a viral vector comprising a nucleic acid encoding Apoptosis-associated Speck-like protein containing a CARD (ASC) and/or gasdermin D operably linked to a tumor cell-specific promoter.
8. The method of any of paragraphs 1-7, wherein the ASC and/or gasdermin D is a human, mouse, or rat ASC and/or gasdermin D.
9. The method of any of paragraphs 1-8, wherein the Schwann cell-specific promoter is a P0, a peripheral myelin protein 22 (PMP22), or a MBP promoter.
10. The method of any of paragraphs 1-9, wherein the subject in need of treatment for a schwannoma is a subject having or diagnosed as having a condition selected from the group consisting of: neurofibromatosis 1 (NF1); neurofibromatosis 2 (NF2); schwannomatosis; meningioma; nerve sheath tumor; schwannoma; vestibular schwannoma; sporadic schwannoma; neurofibrosarcoma; neurofibroma; neurofibromatosis (NF); malignant peripheral nerve sheath tumor; and a combination thereof.
11. The method of any of paragraphs 1-10, wherein the viral vector is a recombinant adeno-associated virus (rAAV).
12. The method of paragraph 11, wherein the rAAV is of serotype AAV1 or AAV9.
13. The method of any of paragraphs 1-12, wherein the Schwann cell specific promoter is upstream of the nucleic acid encoding ASC and/or gasdermin D.
14. The method of any of paragraphs 1-13, wherein the vector further comprises a polyadenylation signal.
15. The method of paragraph 14, wherein the polyadenylation signal is downstream of the nucleic acid encoding ASC and/or gasdermin D.
16. The method of paragraph 14 or 15, wherein the polyadenylation signal comprises a bovine growth hormone polyadenylation signal (BGHpA), a SV40 polyadenylation signal or a rabbit beta-globin polyadenylation signal.
17. The method of any of paragraphs 1-16, wherein the vector further comprises a first AAV inverted terminal repeat (ITR) located upstream of the Schwann cell specific promoter and a second AAV ITR located downstream of the polyadenylation signal.
18. The method of paragraph 17, wherein the first or second AAV inverted terminal repeat comprises a deletion of the terminal resolution site.
19. The method of any of paragraphs 1-18, wherein the vector is a polynucleotide.
20. The method of any of paragraphs 1-19, wherein the vector is a single-stranded or double-stranded AAV.
21. The method of any of paragraphs 1-20, wherein the vector is a self-complementary AAV (scAAV).
22. The method of any of paragraphs 1-21, wherein the vector is a virus particle.
23. The method of any of paragraphs 1-22, wherein the vector is administered directly to the tumor.
24. The method of any of paragraphs 1-23, wherein the vector is administered by intratumoral injection.
25. The method of any of paragraphs 1-24, wherein the vector is administered directly to a nerve affected by a schwannoma.
26. The method of any of paragraphs 1-25, wherein administering is intranervously, intracranially, intratumorally, intramuscularly, intravenously, intradermally, or subcutaneously, or a combination thereof.
27. The method of any of paragraphs 1-26, wherein the subject is also treated by surgical removal of the schwannoma.
28. The method of any of paragraphs 1-27, wherein the subject is not administered a viral vector comprising a caspase gene.
29. A viral vector comprising a nucleic acid encoding Apoptosis-associated Speck-like protein containing a CARD (ASC) and/or gasdermin D gene and a Schwann cell-specific promoter.
30. The vector of paragraph 29, wherein the viral vector is a recombinant adeno-associated virus (rAAV).
31. The vector of any of paragraphs 29-30, wherein the rAAV is of serotype AAV1 or AAV9.
32. The vector of any of paragraphs 29-31, wherein the Schwann cell specific promoter is upstream of the nucleic acid encoding ASC and/or gasdermin D.
33. The vector of any of paragraphs 29-32, further comprising a polyadenylation signal.
34. The vector of paragraph 29-33, wherein the polyadenylation signal is downstream of the nucleic acid encoding ASC and/or gasdermin D.
35. The vector of paragraph 29-34, wherein the polyadenylation signal comprises a bovine growth hormone polyadenylation signal (BGHpA), a SV40 polyadenylation signal or a rabbit beta-globin polyadenylation signal.
36. The vector of any of paragraphs 29-35, further comprising a first AAV inverted terminal repeat (ITR) located upstream of the Schwann cell specific promoter and a second AAV ITR located downstream of the polyadenylation signal.
37. The vector of paragraph 36, wherein the first or second AAV inverted terminal repeat comprises a deletion of the terminal resolution site.
38. The vector of any of paragraphs 29-37, wherein the vector is a polynucleotide.

39. The vector of any of paragraphs 29-38, wherein the vector is a single-stranded or double-stranded AAV.
40. The vector of any of paragraphs 29-39, wherein the vector is a self-complementary AAV (scAAV).
41. The vector of any of paragraphs 29-40, wherein the vector is a virus particle.
42. The vector of any of paragraphs 29-41, wherein the vector does not comprise a caspase gene.
43. A pharmaceutical composition comprising the viral vector of any of paragraphs 29-42 and a pharmaceutically acceptable carrier.
44. A kit comprising a composition comprising the viral vector of any of paragraphs 29-42 contained within packaging materials.

Some embodiments of the technology described herein can be defined according to any of the following numbered paragraphs:

1. A method of treating a schwannoma in a subject in need thereof, the method comprising administering a viral vector comprising a nucleic acid encoding Apoptosis-associated Speck-like protein containing a CARD (ASC) and/or gasdermin D operably linked to a Schwann cell-specific promoter.
2. A method of inducing cell death of a target cell, the method comprising contacting the target cell with a nucleic acid encoding Apoptosis-associated Speck-like protein containing a CARD (ASC) and/or gasdermin D.
3. The method of paragraph 2, wherein contacting step further comprises contacting the target cell with a viral vector comprising the nucleic acid encoding ASC and/or gasdermin D.
4. The method of any of paragraphs 2-3, wherein the target cell is a cancer and/or tumor cell.
5. The method of paragraph 4, wherein the nucleic acid encoding ASC and/or gasdermin D is operably linked to a cell-type specific promoter or a cancer and/or tumor cell-specific promoter.
6. The method of any of paragraphs 2-5, wherein the contacting step comprises administering the nucleic acid to a subject comprising the target cell.
7. A method of treating a tumor or neoplasm in a subject in need thereof, the method comprising administering a viral vector comprising a nucleic acid encoding Apoptosis-associated Speck-like protein containing a CARD (ASC) and/or gasdermin D operably linked to a cell-type specific promoter or a tumor cell-specific promoter.
8. The method of any of paragraphs 1-7, wherein the ASC and/or gasdermin D is a human, mouse, or rat ASC and/or gasdermin D.
9. The method of any of paragraphs 1-8, wherein the Schwann cell-specific promoter is a P0, a peripheral myelin protein 22 (PMP22), or a MBP promoter.
10. The method of any of paragraphs 1-9, wherein the promoter is a human or murine promoter.
11. The method of any of paragraphs 1-10, wherein the subject in need of treatment for a schwannoma, tumor, or neoplasm is a subject having or diagnosed as having a condition selected from the group consisting of: neurofibromatosis 1 (NF1); neurofibromatosis 2 (NF2); schwannomatosis; meningioma; nerve sheath tumor; schwannoma; vestibular schwannoma; sporadic schwannoma; neurofibrosarcoma; neurofibroma; neurofibromatosis (NF); malignant peripheral nerve sheath tumor; and a combination thereof.
12. The method of any of paragraphs 1-11, wherein the viral vector is a recombinant adeno-associated virus (rAAV).
13. The method of paragraph 12, wherein the rAAV is of serotype AAV1 or AAV9.
14. The method of any of paragraphs 1-13, wherein the Schwann cell specific promoter is upstream of the nucleic acid encoding ASC and/or gasdermin D.
15. The method of any of paragraphs 1-14, wherein the vector further comprises a polyadenylation signal.
16. The method of paragraph 15, wherein the polyadenylation signal is downstream of the nucleic acid encoding ASC and/or gasdermin D.
17. The method of paragraph 15 or 16, wherein the polyadenylation signal comprises a bovine growth hormone polyadenylation signal (BGHpA), a SV40 polyadenylation signal or a rabbit beta-globin polyadenylation signal.
18. The method of any of paragraphs 1-17, wherein the vector further comprises a first AAV inverted terminal repeat (ITR) located upstream of the Schwann cell specific promoter and a second AAV ITR located downstream of the polyadenylation signal.
19. The method of paragraph 18, wherein the first or second AAV inverted terminal repeat comprises a deletion of the terminal resolution site.
20. The method of any of paragraphs 1-19, wherein the vector is a polynucleotide.
21. The method of any of paragraphs 1-20, wherein the vector is a single-stranded or double-stranded AAV.
22. The method of any of paragraphs 1-21, wherein the vector is a self-complementary AAV (scAAV).
23. The method of any of paragraphs 1-22, wherein the vector is a virus particle.
24. The method of any of paragraphs 1-23, wherein the vector is administered directly to the tumor.
25. The method of any of paragraphs 1-24, wherein the vector is administered by intratumoral injection.
26. The method of any of paragraphs 1-25, wherein the vector is administered directly to a nerve affected by a schwannoma, tumor, or neoplasm.
27. The method of any of paragraphs 1-26, wherein administering is intranervously, intracranially, intratumorally, intramuscularly, intravenously, intradermally, or subcutaneously, or a combination thereof.
28. The method of any of paragraphs 1-27, wherein the subject is also treated by surgical removal or reduction of the schwannoma, tumor, or neoplasm.
29. The method of any of paragraphs 1-28, wherein the subject is not administered a viral vector comprising a caspase gene.
30. A viral vector comprising a nucleic acid encoding Apoptosis-associated Speck-like protein containing a CARD (ASC) and/or gasdermin D gene and a Schwann cell-specific promoter.
31. The vector of paragraph 30, wherein the viral vector is a recombinant adeno-associated virus (rAAV).
32. The vector of any of paragraphs 30-31, wherein the rAAV is of serotype AAV1 or AAV9.
33. The vector of any of paragraphs 30-32, wherein the Schwann cell specific promoter is upstream of the nucleic acid encoding ASC and/or gasdermin D.
34. The vector of any of paragraphs 30-33, wherein the promoter is a human or murine promoter.
35. The vector of any of paragraphs 30-34, further comprising a polyadenylation signal.

36. The vector of paragraph 30-35, wherein the polyadenylation signal is downstream of the nucleic acid encoding ASC and/or gasdermin D.
37. The vector of paragraph 30-36, wherein the polyadenylation signal comprises a bovine growth hormone polyadenylation signal (BGHpA), a SV40 polyadenylation signal or a rabbit beta-globin polyadenylation signal.
38. The vector of any of paragraphs 30-37, further comprising a first AAV inverted terminal repeat (ITR) located upstream of the Schwann cell specific promoter and a second AAV ITR located downstream of the polyadenylation signal.
39. The vector of paragraph 38, wherein the first or second AAV inverted terminal repeat comprises a deletion of the terminal resolution site.
40. The vector of any of paragraphs 30-39, wherein the vector is a polynucleotide.
41. The vector of any of paragraphs 30-40, wherein the vector is a single-stranded or double-stranded AAV.
42. The vector of any of paragraphs 30-41, wherein the vector is a self-complementary AAV (scAAV).
43. The vector of any of paragraphs 30-42, wherein the vector is a virus particle.
44. The vector of any of paragraphs 30-43, wherein the vector does not comprise a caspase gene.
45. A pharmaceutical composition comprising the viral vector of any of paragraphs 30-44 and a pharmaceutically acceptable carrier.
46. A kit comprising a composition comprising the viral vector of any of paragraphs 30-44 contained within packaging materials.

EXAMPLES

Example 1

Described herein are methods and compositions relating to the activation of the inflammasome and/or induction of apoptosis for the treatment of non-malignant tumors of the central and peripheral nervous system, such as meningioma, type 1 and 2 neurofibromatosis, and schwannomatosis. The inflammasome is a multiprotein structure responsible for: 1) inducing canonical caspase3/7 apoptosis, 2) inducing inflammatory cell death through pyroptosis, 3) releasing immuno-stimulatory cytokines to the extracellular milieu. Thus, this pathway can not only induce death of cancer cells, but also establishing a local "zone of resistance" or a systemic immune response that prevents formation of new tumors locally or distally.

As described herein, delivering activated genes downstream of the inflammasome pathway under the control of tumor-specific promoters (such as the P0 promoter of schwannoma cells) induces a death signal very specific to tumor cells without causing any toxicity in the surrounding normal tissue (such as neuronal toxicity when treating schwannomas established in peripheral nerves).

This treatment is particularly beneficial for non-malignant, non-neuronal, tumors of the central and peripheral nervous system as they develop in environments that frequently can not be operated upon without causing major damage, they are difficult to reach with pharmacotherapy, and permits selective targeted through specific genetic regulation. In addition, these tumors have the characteristic of developing in multiple sites over the patient's life span and therefore require the exploitation of the host's local and systemic immune response to be fully treated.

Also described herein are adeno-associated viruses, AAV1 and AAV9, activating the inflammasome-induced pyroptosis and apoptosis through the delivery of either Gasdermin D or ASC, respectively, under the control of P0 promoter.

ASC and Gasdermin D are downstream factors of different inflammasome pathways and they were found to be silenced and/or deleted in human cancers (Saeki N, 2009, PMID: 19051310). It is demonstrated herein that ASC is silenced in human schwannomas through methylation. These data indicate a crucial role for this signaling in controlling cancer progression and initiation. However, no publications have reported the use of these, or other inflammasome genes, for tumor treatment.

Described herein is the activation of the inflammasome for the treatment of tumors. Further described herein is the use of gene therapy for the above purpose, and the development of new AAV vectors (AAV1 and AAV9) carrying a downstream component of the inflammasome that was shown to be deleted/silenced in human tumors, specifically ASC or Gasdermin D, under the control of the schwannoma-specific promoter P0.

The methods and compositions described herein can relate to the treatment of schwannomas. Schwannomas are benign tumors associated with three different devastating neurological diseases with the following incidence:
NF1—1:3000
NF2—1:35,000
Schwannomatosis—1:100,000
Meningiomas—7:100,000

Even though these tumors are sometimes successfully removed surgically, in many other cases the surgery may cause debilitating neurological dysfunction or the tumors simply cannot be removed due to location. In addition, when the tumors are removed successfully they usually keep returning through the patient's life and each time they carrying a significant threat of severe neurological consequences. Unlike malignant cancers that are the result of multiple mutations and thus affect primarily the older population, these tumors are due to a single genetic mutation and usually occur in young adults and frequently also in children. Thus, the methods and compositions described herein can also be combined with surgical tumor removal to vaccinate the patients against the potential formation of other tumors. It is important to note that currently there are no pharmacologic means to treat these tumors.

Example 2: Adeno Associated Viral Vectors Delivery of Apoptosis-Associated Speck-Like Protein Containing a CARD Suppresses Schwannoma Tumor Growth in Mouse Models Schwannomas are tumors of Schwann cells lineage which cause pain, sensory/motor dysfunction, and death through compression of peripheral nerves, the spinal cord, and/or the brain stem. Neurofibromatosis 2 (NF2) and schwannomatosis originate in children or young adults and develop in multiple locations throughout life. Currently there is no efficient treatment for these tumors, surgical resection is the main treatment approach but it is limited in scope and efficacy and has significant associated morbidity.

Described herein is the investigation of the epigenetic alteration and biological function of the pro-apoptotic gene ASC/TMS1 in human Schwannoma cell lines. In comparison to cultured human Schwann cells, ASC/TMS1 was down regulated in human Schwannoma cell line HEI-193 and human primary schwannoma cells from three different patients. The down-regulation of ASC/TMS1 was correlated with promoter hypermethylation. Ectopic over expression of ASC in NF2 cells resulted in a significant cell death which is likely due to activation of apoptotic caspase 9 and 3 in addition to direct interaction with pro-apoptotic proteins such as BID. Intra-tumoral injection of an adeno-associated virus (AAV) serotype 1 vector encoding (ASC) under the Schwann-cell specific promoter, P0, lead to significant reduction of the tumor growth in schwannoma mouse model in which immortalized human NF2 schwannoma cells expressing luciferase are implanted in the sciatic nerve of nude mice. The tumor growth reduction is concomitant with resolution of tumor-associated pain, no vector-mediated neuropathology, and no changes in sensory or motor function.

Schwannomas are slow growing tumors of Schwann cells origin (1, 2). In 60% of the cases these lesions arise in children and young adults and new tumors continue to develop in multiple locations throughout the patient's life (3). Schwannomas lack expression of a functional neurofibromatosis type 2 (NF2) protein, merlin/schwannomin (4, 5). Merlin is a unique member of the ezrin-radixin-moesin gene family with tumor-suppressing activities (6). Its overexpression was shown to reduce cell growth which is associated with cell-cycle arrest and apoptosis (7, 8). Current treatment is limited to resection, which is not always possible because of the risk of nerve or brain stem damage and consequently possible sensory loss (including deafness and pain) and motor dysfunction. Clinical trials testing cancer chemotherapeutics, such as anti-angiogenic compounds and small molecules, are ongoing, but long-lasting significant therapeutic effect has not been proven yet.

Schwannomas are appropriate targets for gene therapy, as they grow slowly and can be readily localized using magnetic resonance imaging (MRI). The advantage of gene-therapy over surgical resection is that the former utilizes a minimally invasive procedure (image guided needle injection).

A complex multiprotein structure called the inflammasome is responsible for inducing apoptotic cell death and inflammatory responses. The inflammasome activates a subset of caspases known as the inflammatory caspases, such as caspase-1 (13). When stimulated, inflammasomes assemble to represent the first line of host defense through proteolytic activation of caspase-1 which in turn maturates cytokines interleukin-1B and interleukin 18 and initiate an inflammatory cell death named as pyroptosis (14, 15, 16). The work described herein utilizes the only broadly accepted NF2 cell line model HEI-193.

Apoptosis-associated speck-like protein containing a CARD (caspase recruitment domain) (ASC or Pycard) is the main and most critical required adaptor that recruits caspase-1 to inflammasome complex (17). ASC is an intracellular signaling molecule consisting of an N-terminal pyrin domain (PYD) and a C-terminal CARD. PYD and CARD domains are death domains that mediate the assembly of large signaling complexes in apoptotic and inflammatory signaling pathways (18). ASC is also referred to as target of methylation-induced silencing (TMS1).

Matched primary schwannoma and schwann cell lines were screened for the expression of the inflammasome components which have the key role in mediating caspase1 biological effect. In the present study, the data indicate that ASC is epigenetically silenced by methylation in human NF2 cancer cell line (HEI-193) and primary human Schwannoma samples. In vitro over-expression of ASC gene in different NF2 cells resulted in a significant cell death. The data also demonstrated that the effect is likely due to activation of apoptotic caspase 9 and 3 in addition to direct interaction with pro-apoptotic proteins such as BID.

Also described herein is the development of a gene therapy vector using adeno-associated virus (AAV) to deliver ASC under a Schwann specific cell promoter (P0). AAV-P0-ASC direct intra sciatic nerve injection into the tumor of immune-compromised Schwannoma mice model resulted in a significant reduction in tumor growth, as assessed by in vivo bioluminescence imaging and correlative histopathology. In a proximal sciatic nerve implantation model, designed to cause pain like behavior as assessed by plantar von Frey withdrawal threshold (i.e., mechanical sensitization) and Hargreaves withdrawal latency (i.e. thermal sensitization), intratumoral AAV1-P0-ASC injection alleviated pain sensitivity in parallel with tumor growth inhibition.

Figure 1B:
FIG. 1B depicts a methylation assay on ASC performed by methylation specific PCR analysis of bisulfite-modified gDNA. HEI193 and the three primary Schwannomas ASC was fully methylated while the human Schwann cells showed fully unmethylated pattern. (M: Primers for Methylated ASC, U; Primers for Unmethylated ASC).
Figure 1A:
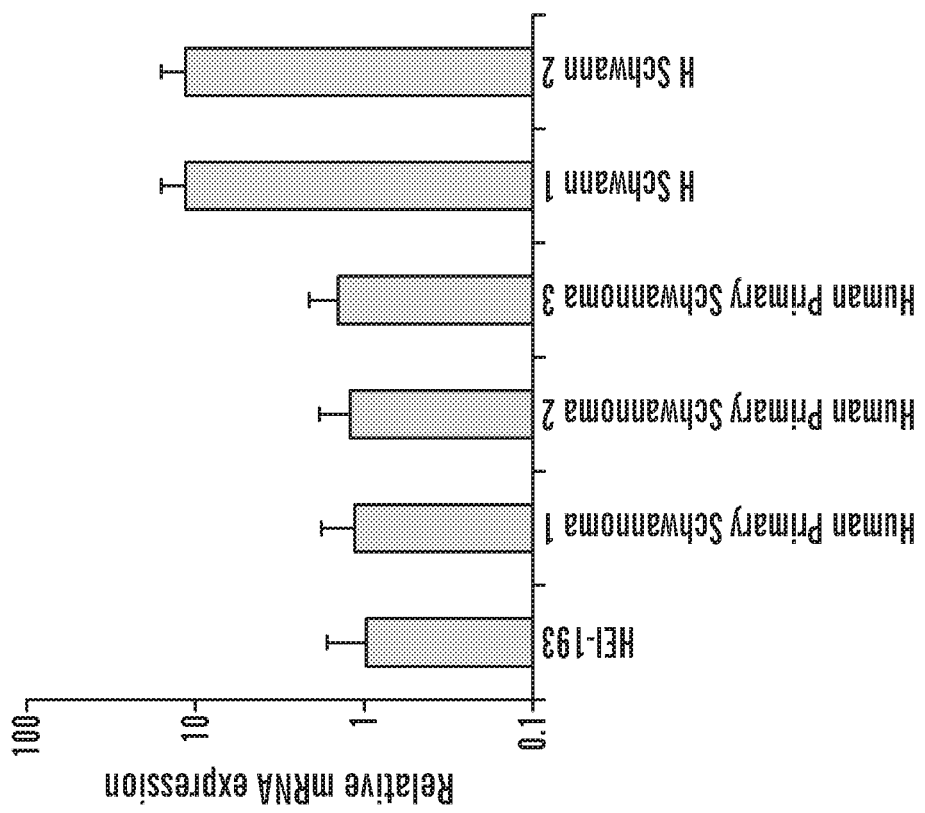
FIG. 1A depicts quantitative RT-PCR analysis demonstrating ASC expression profile in Human HEI-193 schwannoma cell lines, three Schwannoma primary cultures from different patients and two different human Schwann cells cultures. Quantitative PCR data are normalized to 18S gene and presented as the fold increase. More than 10-fold increase was observed in ASC expression in Schwann cells over schwannoma cells.

Results mRNA expression of ASC/Pycard/TMS1 was analyzed by quantitative RT-PCR in cultured Schwann cells, Schwannoma HEI193 cell lines and three human primary schwannoma cultured cells. The results demonstrated that ASC was down-regulated or silenced in the Schwannoma cells. However, cultured Schwann cells showed higher expression of ASC (FIG. 1A). Exploration of the ASC CpG rich promoter hypermethylation by methylation specific PCR (MS-PCR) revealed full methylation of ASC in the schwannoma cells while no methylation was detected in the cultured Schwann cells ASC (FIG. 1B).

Figures 2A, 2B:
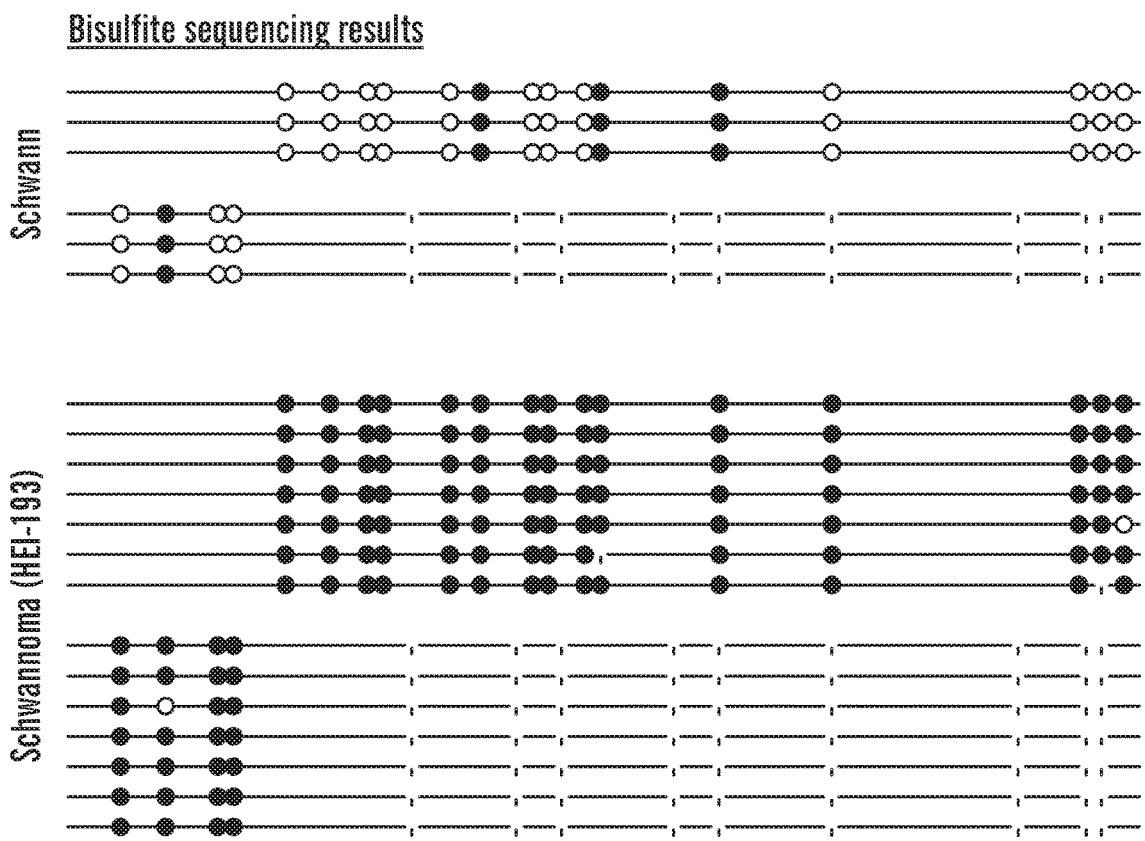
FIGS. 2A-2B depict bisulfite sequencing analysis of 19 CpG sites in TMS1 CpG island. Bisulfite converted DNA extracted from cultured human Schwann cells or HEI-193 schwannoma cell line was amplified with primer set indicated by arrows in the human TMS1 genome (FIG. 2A).

Further characterization and validation of the methylation density within the ASC promoter was performed using bisulfite genome sequencing. The sequencing data were consistent with those of MS-PCR. Massive methylation was found in the tumor cells, not in the normal cultured cells (FIGS. 2A-2B).

Figure 3:
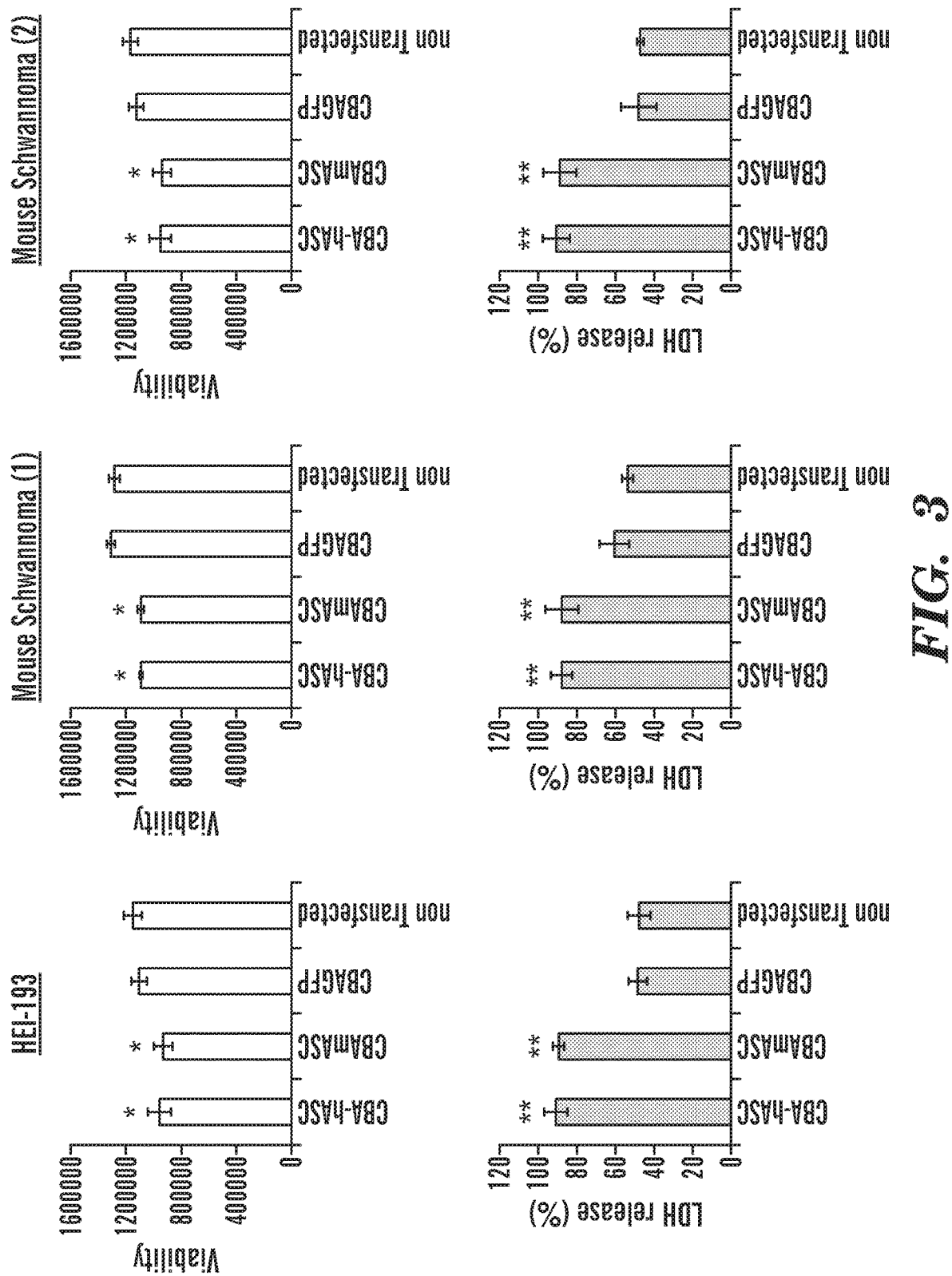
FIG. 3 depicts ATP-based cell viability (upper three graphs) and Lactate dehydrogenase (LDH) release cytotoxicity (lower three graphs) measured at 24 h after transient transfection of human HEI193 schwannoma, mouse Schwannoma 1 (08031-9) and mouse schwannoma 2 (NF2S1) by pAAV-CBA-hASC, pAAV-CBA-mASC, pAAV-CBA-GFP or nontransfected cells. Graphs show the mean±SEM of triplicate wells and are representative of three independent experiments.

In vitro effect of ASC over expression on human and mouse Schwannoma cell lines. Human and mouse ASC were cloned into AAV plasmid backbones down-stream of constitutive CBA promoter. Transfection of human schwannoma cell lines (HEI-193) and two mouse schwannoma cell lines (08031-9 and NF2S1) showed significant reduction in cell viability and significant cell death as indicated by increased LDH release upon over expression of ASC into the Schwannoma cells (FIG. 3).

Figures 4A, 4B:
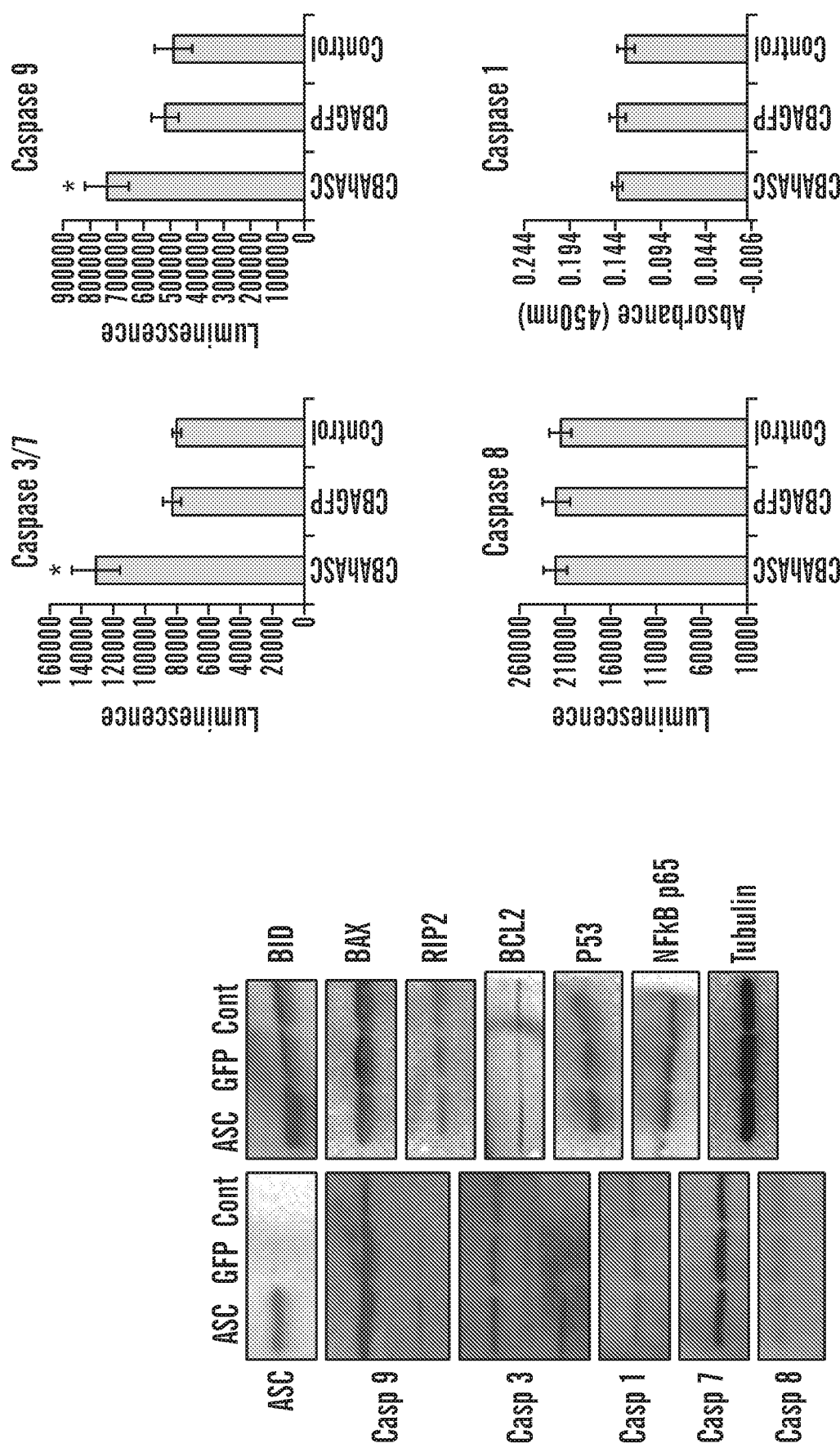
FIG. 4A depicts western blotting of HEI193 cell lysates 24 h after transfection with pAAV-CBA-hASC, pAAV-CBA-GFP or non transfected showed that ASC over-expression was associated with over expression and cleavage of caspase 9, cleavage of caspase 3 and over expression of BID.
FIG. 4B depicts graphs of transfected HEI193 assayed for endogenous caspases, demonstrating an increased activity for caspase 3/7 and caspase 9. Data were presented as means±SEM (n=3). *P<0.05 (t-test).

Further, an increase of caspase 3/7 activity and caspase 9 activity was observed by colorimetric luminescence assays after transfection of HEI-193 with pAAV-CBA-hASC in comparison to the cells transfected with pAAV-CBA-GFP control plasmid and non transfected cells (FIG. 4B). Induction of apoptosis was additionally assessed by immunoblot detection of caspase 1, 3, 7, 8 and 9. As shown in FIG. 4A, over-expression of ASC/TMS1 enhanced the levels of active form of caspase 3 and 9 and expression of pro-apoptotic factor BID.

Figure 5A:
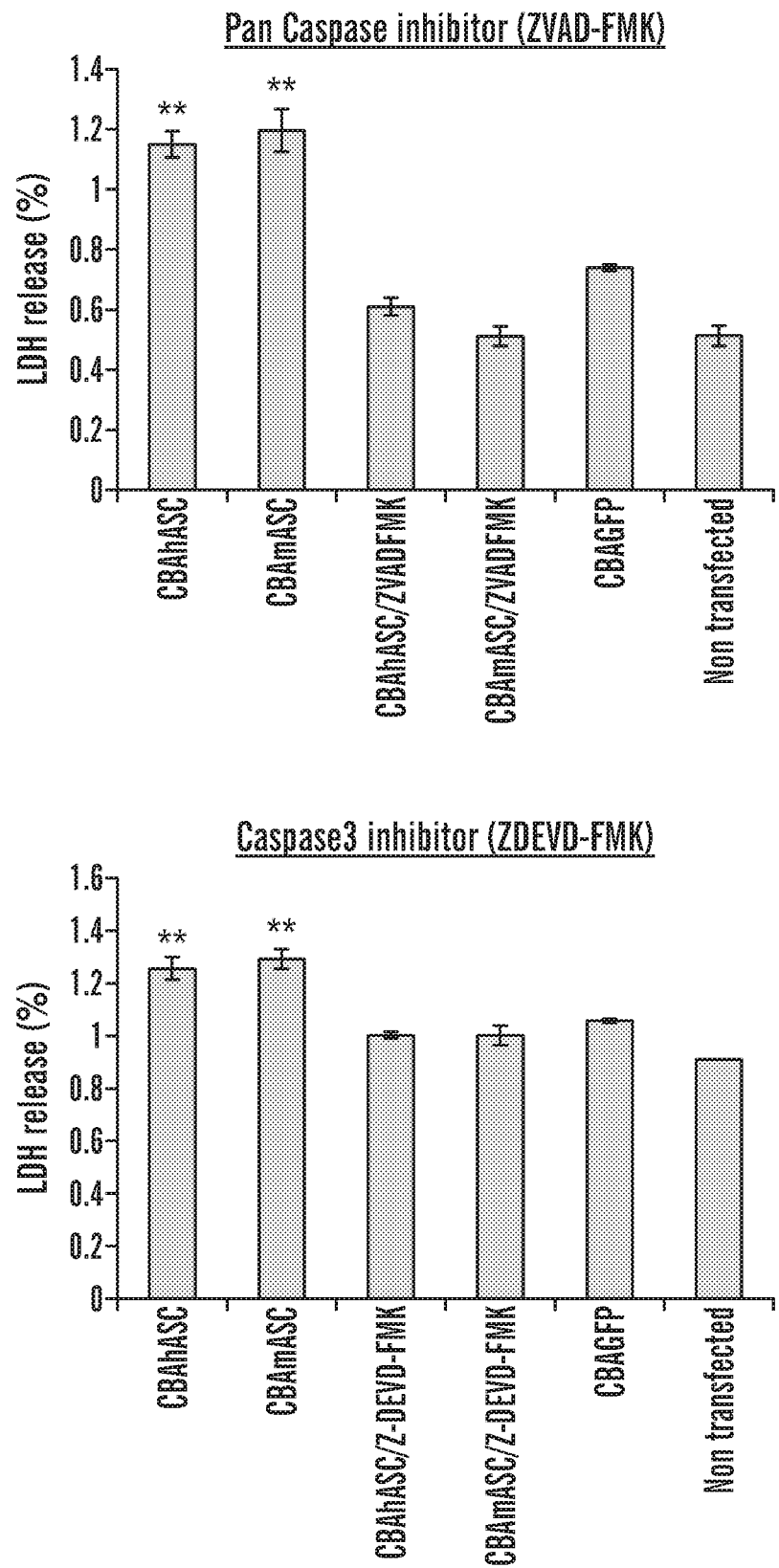
FIG. 5A demonstrates that pan caspase inhibitor (ZVAD-FMK) and caspase 3 inhibitor (ZDEVD-FMK ("DEVD" is disclosed as SEQ ID NO: 13)) inhibited the LDH release cytotoxicity in the HEI193 cells which were transfected with pAAV-CBA-hASC.
Figure 5B:
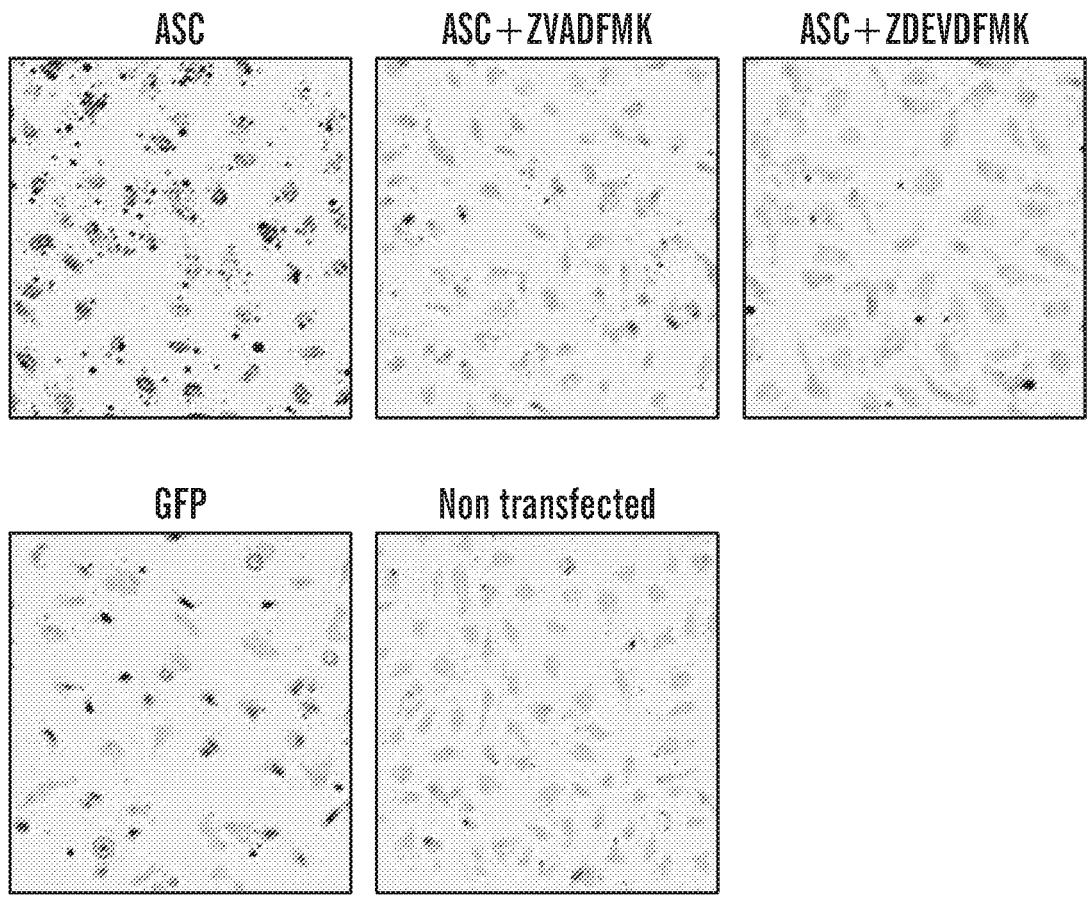
FIG. 5B depicts images of in vitro apoptosis staining of the same cells after transfection with pAAV-CBA-ASC, demonstrating obvious brown stained apoptotic bodies. However, no apoptosis was shown in presence of pan-caspase inhibitor, caspase3 inhibitor, cells transfected with pAAV-CBA-GFP or non transfected cells. Data were presented as means±SEM (n=3). *P<0.05 (t-test).

To determine whether the ASC/TMS1-mediated growth inhibition was the result of caspases induced apoptosis, in vitro apoptosis staining was performed using TACS 2 TdT-DAB In situ Apoptosis Detection kit (Trevigen). Over expression of ASC/TMS1 resulted in a significant increase in apoptotic cells as compared with vector control in HEI-193 cells. Pan caspase inhibitor (ZVADFMK) and Caspase3 inhibitor (ZDEVDFMK ("DEVD" is disclosed as SEQ ID NO: 13)) were shown to inhibit the apoptotic effect of ASC (FIGS. 5A-5B).

Figure 6A:
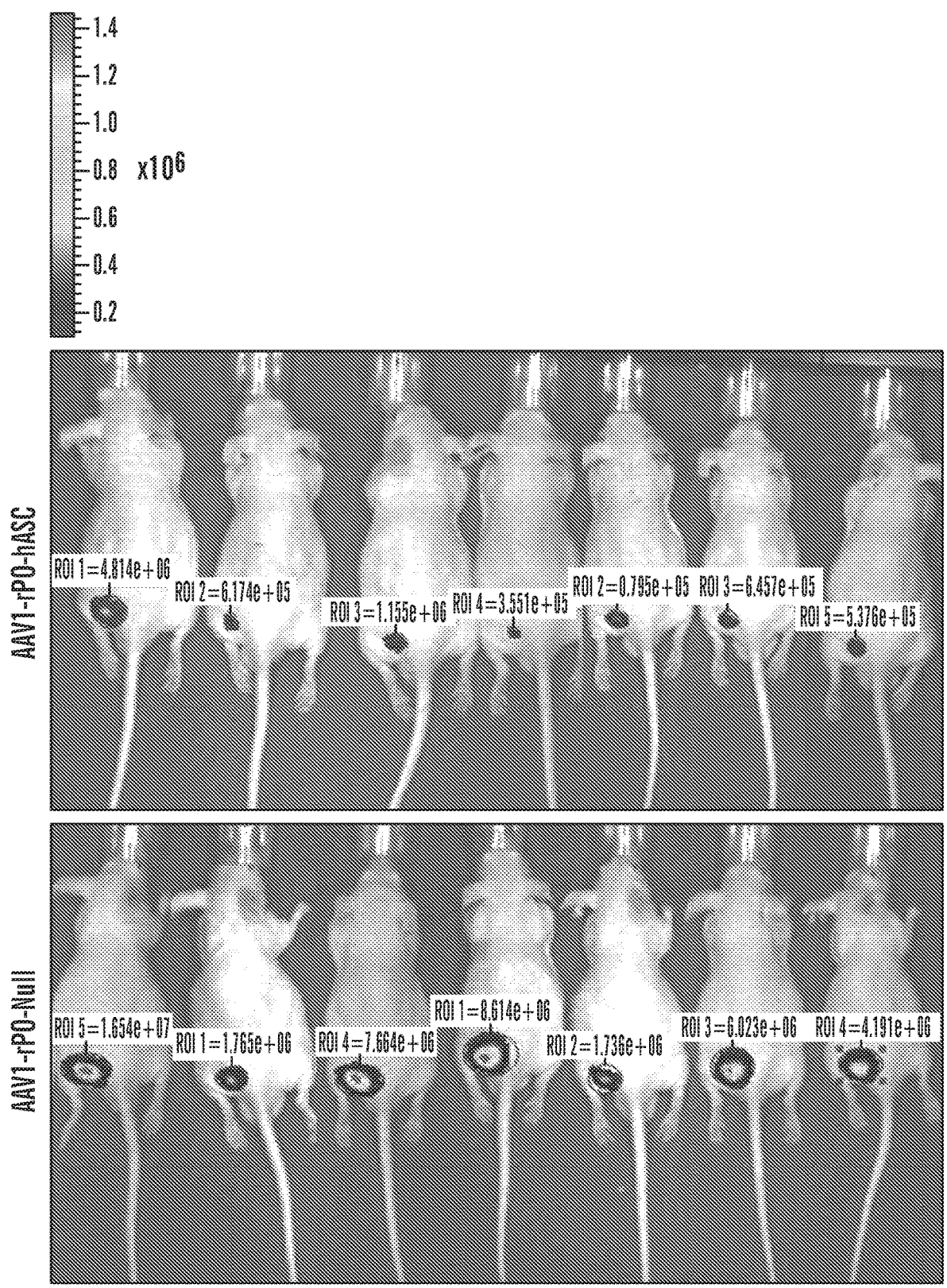
FIG. 6A depicts representative bioluminescence images showing growth of schwannoma in sciatic nerve and growth delay of tumors that have been treated with AAV-P0-ASC. Images were taken at week 8 post implantation.
Figure 6B:
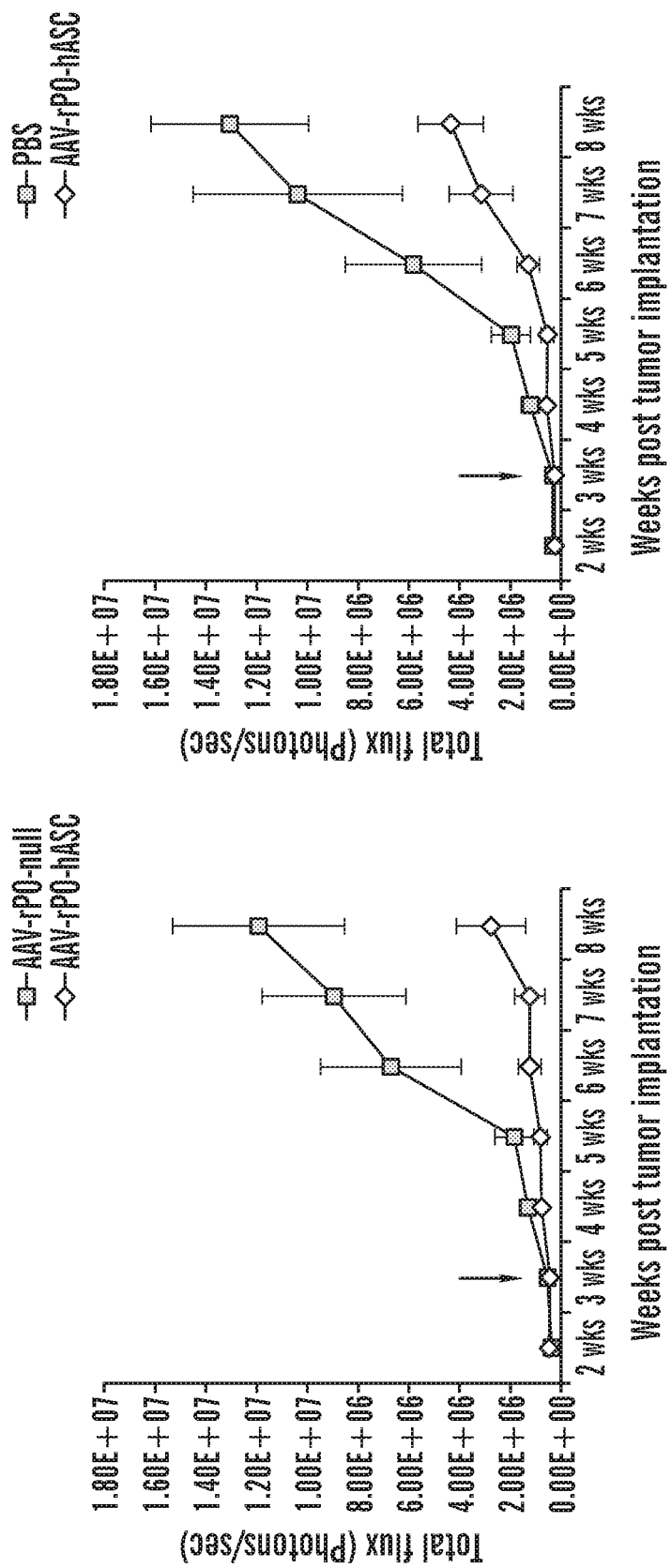
FIG. 6B depicts graphs of monitoring of schwannoma volumes in vivo by bioluminescence imaging. Thirty thousand HEI-193FC cells were implanted into the distal sciatic nerve of nude mice and tumor volume was monitored at weekly intervals by in vivo bioluminescence imaging. At the third week after implantation when tumors were established, they were injected with either AAV1-P0-ASC vs. AAV1-P0-null vector (lower left graph) or AAV1-P0-ASC vs. PBS (lower right graph). Data points are shown as mean values±SEM (n=8 per group for each experiment). Significant difference between AAV-P0-ASC and AAV-P0-null or PBS was observed by ANOVA with repeated measures.

Effects of delivery of AAV1-P0-ASC vectors to schwannomas. The therapeutic efficacy of the AAV1-P0-ASC vector was tested in a mouse model in which schwannomas are generated via implantation of HEI-193FC cells in the sciatic nerve of nude mice. Two independent experiments were done in which control group was injected with either AAV-P0-null or PBS. Intratumoral injection of the AAV1-P0-ASC, AAV1-P0-null or PBS was performed at the site of early HEI-193FC tumor formation prevented further growth as assessed by in vivo bioluminescence imaging over a 6 weeks period after vector injections (FIGS. 6A-6B). Two-way ANOVA with repeated measures revealed a significant effect of AAV1-P0-ASC treatment.

Figure 7B:
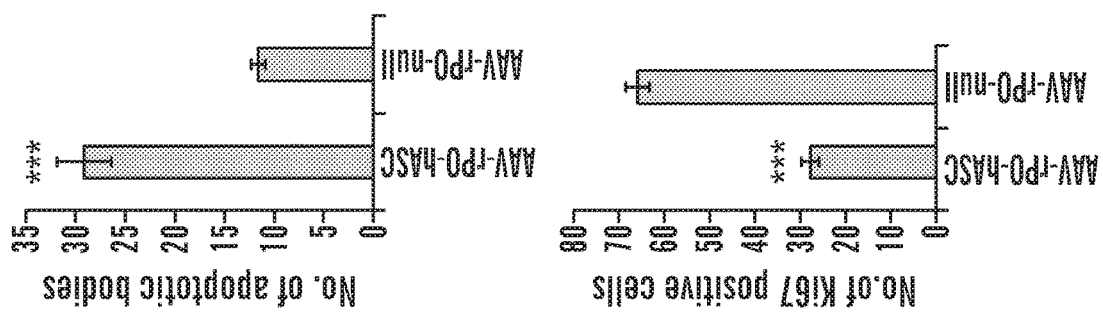
FIG. 7B depicts quantification of apoptotic bodies and Ki67-positive cells showed higher apoptosis rate and less proliferation in the tumors injected with AAV-P0-ASC in comparison to tumors injected with AAV-P0-null. Data were presented as means±SEM (n=3). *P<0.05 (t-test).
Figure 7A:
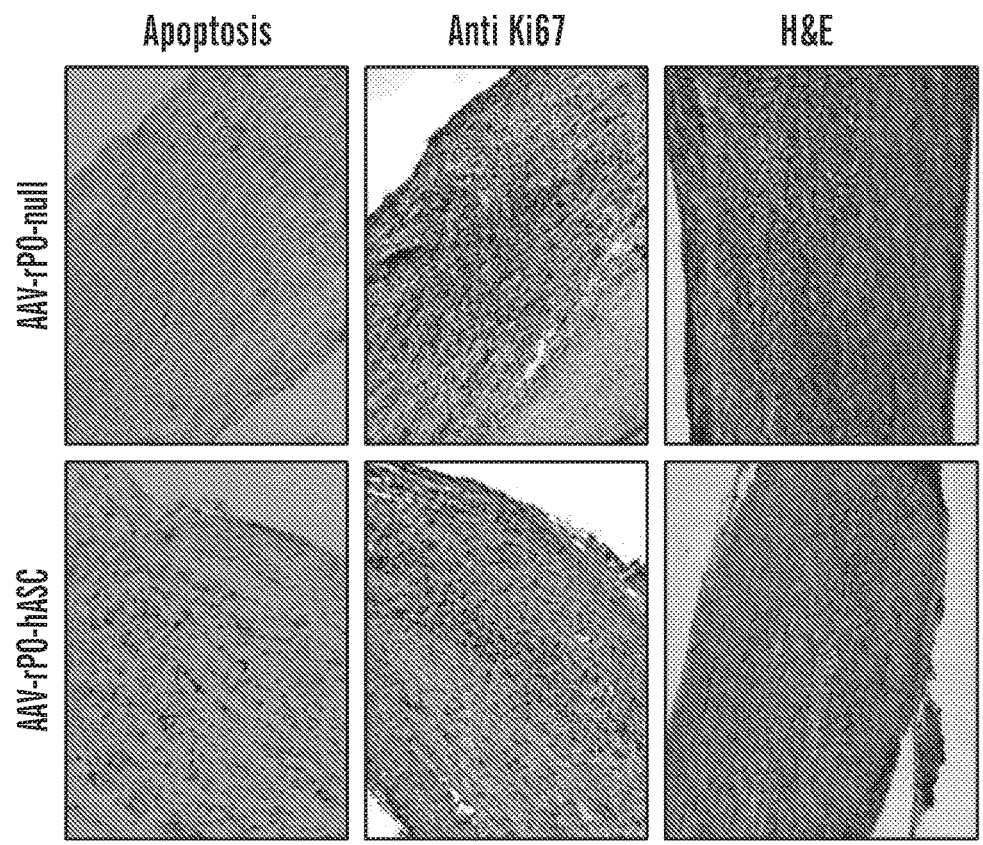
FIG. 7A depicts microscopic evaluation of AAV1-P0-ASC- and AAV1-P0-Null-injected HEI-193FC schwannomas. Tumors injected with AAV-P0-ASC showed increased rate of intra-tumoral apoptosis (brown stained). Imunohistochemical staining for the proliferation marker expression (ki67) was lower in tumor injected with AAV-P0-ASC when compared to the expression level in the tumors injected with AAV-P0-null. Hematoxylin and eosin (H&E) staining showed abundant, mitotically active hematoxylin-positive tumor cells (darkly staining cells) 8 weeks after AAV1-P0-null vector injections into an experimental schwannoma but scant numbers of tumor cells after AAV1-P0-ASC injection.

The difference in tumor growth between the two groups was further confirmed by hematoxylin and eosin staining of nerve sections where a clear difference in tumor size could be observed. Also, staining of the nerves for proliferation or apoptosis marker revealed a clear difference between the two groups, with the ASC injected mice showing less proliferation and more apoptotic bodies than the null injected group (FIGS. 7A-7B).

Figure 8:
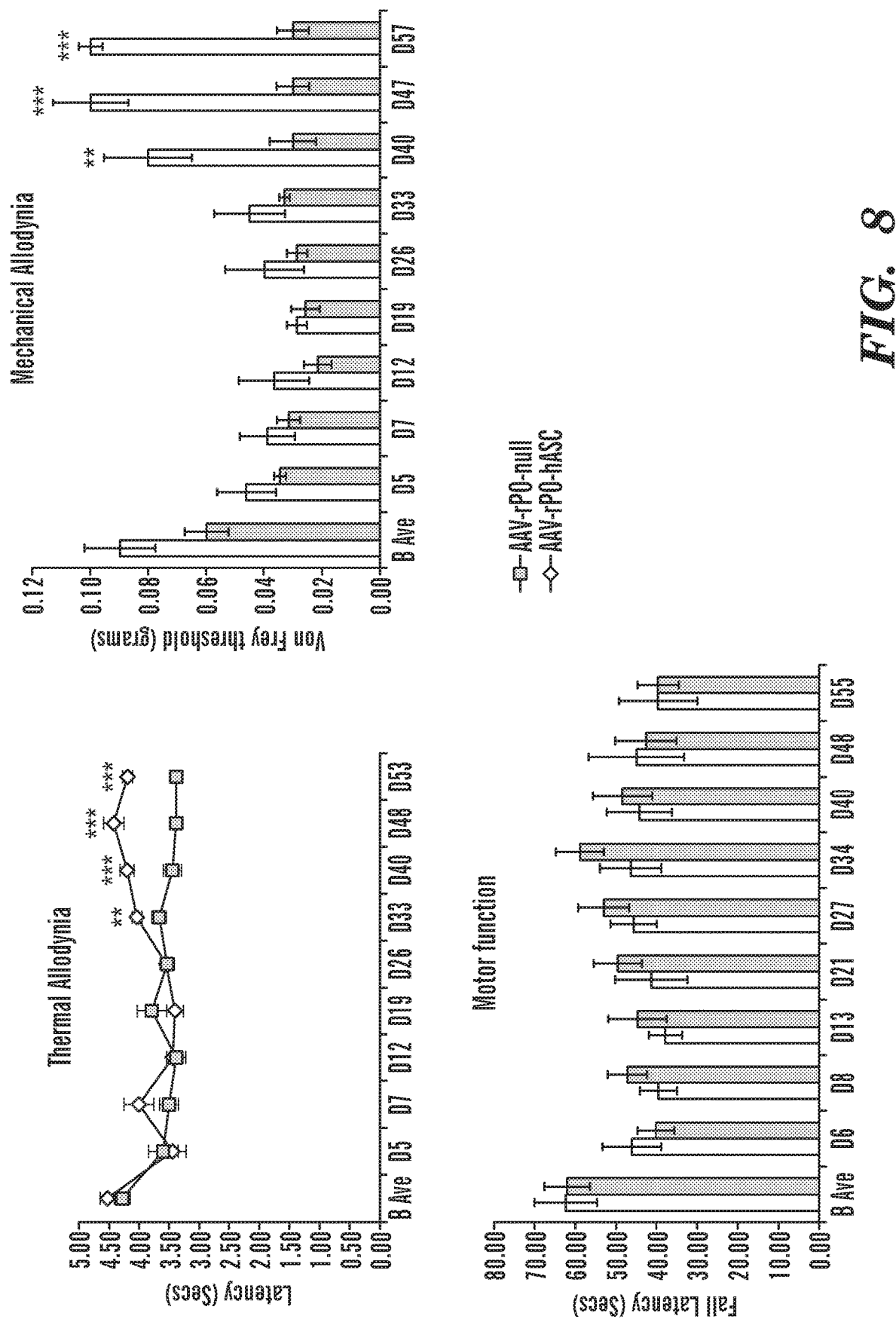
FIG. 8 depicts the effects of AAV1-P0-ASC nerve injection on pain behavior and motor function of implanted sciatic nerve HEI-193FC schwannomas after injection with AAV1-P0-ASC vector or AAV1-P0-null vector at three weeks post implantation. Pain (von Frey method and plantar test) and motor control (rotarod) were evaluated at 3-day intervals for 30 days. AAV1-P0-ASC-mediated tumor growth reduction is correlated with a return of the von Frey threshold and Hargreaves withdrawal latency values to normal baseline. Significant difference between the ASC and null injected groups was observed in reduction of pain behavior as showed by von frey and plantar tests. Results are represented as the mean±SEM of n=8 mice per group (*P<0.05, t test).

AAV1-P0-ASC delivery into Schwannoma tumor reduces the induced pain like behavior. As persistent pain can be a major clinical issue in patients with schwannomatosis and NF2. An experimental Schwannoma model was generated to mimic the clinical schwannoma pain by implanting the HEI193FC more proximal into the sciatic nerve which is limited by Pelvic structure. Consequently, tumor expansion would lead to mechanical sensitization and pain like behavior. The Sensory/pain and motor function was assessed after injection of AAV1-P0-ASC or AAV1-P0-Null nude mice that were implanted with HEI193FC tumor cells in the sciatic nerve. Mechanical ("pain") sensitivity (allodynia) was tested with von Frey filaments to establish withdrawal threshold of the hind paw ipsilateral to the injected sciatic nerve. Thermal (Pain) sensitivity was tested with Plantar Test (Hargreaves' Method) by positioning a movable infra red source underneath the mouse hind paw, pain sensitivity assessed by measuring the withdrawal latency. Gross motor performance was assayed by the accelerating rotarod test. Schwannoma growth was associated with a significant decrease in the von Frey threshold and Hargreaves withdrawal latency in the hind paw ipsilateral to tumor site starting at 4 weeks post-implantation. AAV1-P0-ASC injection led to a statistically significant regression of tumors and an associated return of von Frey threshold and Hargreaves withdrawal latency values to baseline (i.e., normalization of pain sensitivity) as indicated in FIG. 8.

Materials and Methods

Cell culture and transfection. The HEI-193 human schwannoma cell line was established from a schwannoma in a patient with NF2, immortalized with human papillomavirus E6/E7 genes (31) and maintained in Dulbecco's modified Eagle's medium (DMEM) with 2 uM forskolin (Calbiochem, San Diego, CA), recombinant human glial growth factor (14 ng/ml; Sigma-Aldrich, St. Louis, MO), and G418 disulfate salt (50 ug/ml; Sigma-Aldrich). Mouse NF2S-1 schwannoma cells were generated from a spontaneous tumor that formed in nu/nu mice (NCI) and grown as described (32). Mouse 08031-9 cells were grown as described (33). All cells were infected with lentivirus encoding Fluc and mCherry (34). For all cell types, growth media were supplemented with 10% fetal bovine serum (FBS; Sigma-Aldrich) and 1% penicillin-streptomycin (Cellgro, Herndon, VA) and cells were maintained at 37° C. in a humidified atmosphere of 5% $CO_2$ and 95% air. Human Primary Schwannoma cells were maintained in the same medium as HEI-193. Human Primary Schwann cells culture were obtained from (Scien-cells, USA) and maintained in the same medium as for HEI193. For transfections in 24-well format, 100,000 cells were seeded 24 hours prior to transfection. 1 μl of liofectamine 2000 (Invitrogen, USA) was used for every 500 ng of transfected plasmid in FBS free medium (Optimem, Invitrogen, USA). The DNA/Lipofectamine mix was incubated at room temperature for 30 minutes before spread over the cells and left for 5-6 hours then replaced by fresh medium. The amount of plasmid/lipofectamine was scaled up according to the plate format used.

Real-time quantitative PCR analyses. RNA isolation from tissue samples was conducted with TRIzol™ reagent according to the manufacturer's instructions (Qiagen, USA) and transcribed into cDNA using superscript VILO™ cDNA synthesis kit (Invitrogen, USA). Taqman™ real-time PCR was carried out using RealPlex MasterCycler™ (eppendorf, USA). The difference of Ct values between gene of interest (ASC) and reference gene 18S, (DCt) was translated into a relative expression of ASC. Taqman probes were purchased from life technologies, USA.

Methylation-specific PCR. gDNA isolated from cultured cells was subjected to bisulfite conversion using the EZDNA™ Methylation Kit (Zymo Research) according to the manufacturer's directions. Essentially, bisulfite treatment converts non-methylated cytosines into uracil via deamination, which is replicated as thymidine during PCR. In contrast, 5-methyl cytosines are protected and thus identified as cytosines in the resultant PCR product. Briefly, 2 ug of denatured DNA from cell lines was incubated for 4.5 hr in sodium bisulfite and then desalted in DNA-binding columns. Desulphonation by incubation in sodium hydroxide was carried out within the column. The modified DNA was eluted in 20 ul elution buffer, and 50 ng of the recovered DNA was used for MS-PCR analysis. MS-PCRP was performed using primers for the methylated (M) and unmethylated (U) ASC as described (35). Bisulfite modified DNA was amplified by PCR using HotStarTaq™ Master mix kit from Qiagen, USA with the following reaction conditions: 12.5 ul master mix, 2.5 ul of 10 uM primer mix, 50 ng of bisulfite-modified DNA in a final volume of 25 ml. The conditions of the MS-PCR were as follow: 95° C. for 15 min for denaturation, 35 cycles of amplification (94° C., 30 sec; 58° C. 30 sec; 72° C., 45 sec) with a final elongation step of 10 min at 72° C. Reaction products were separated by electrophoresis on a 3% agarose gel, stained with ethidium bromide, and visualized under UV illumination.

Bisulfite genomic sequencing. Genomic DNA was subjected to bisulfite conversion using the EZDNA™ Methylation Kit (Zymo Research) according to the manufacturer's directions. Bisulfite-modified DNA (50 ng) was amplified by nested PCR for bisulfite sequencing under the following reaction conditions: HotStarTaq™ Master mix kit from Qiagen, USA. with the following reaction conditions: 12.5 ul master mix, 2.5 ul of 10 uM primer mix, 50 ng of bisulfite-modified DNA in a final volume of 25 ml. The condition of the PCR reaction was as follows: 95° C. for 15 min for denaturation, 35 cycles of amplification (94° C., 30 sec; 57° C. 30 sec; 72° C., 45 sec) with a final elongation step of 10 min at 72° C. Primers were designed to avoid potential methylation sites (CpGs) so that both methylated and unmethylated DNA would be amplified equally. The first primer set was: 5' GGGGATTTTGGAGTTATGGGG 3' (SEQ ID NO: 14) and 5' AAATAATCCCCTTCCCTTCCC 3' (SEQ ID NO: 15). The second PCR round was done using 1/1000 dilution of the PCR product and the following primer set: 5' AAGAAGTTTAAGTTGAAGTTGTTGT 3' (SEQ ID NO: 16) and 5' ACCATCTCCTACAAACCCATATC 3'

(SEQ ID NO: 17). The resulting amplification pools were sub-cloned into the pCRII-TOPO vector using the TOPO™ TA Cloning kit (Invitrogen). 3-7 individual subclones were isolated per PCR reaction and sequenced by the MGH DNA sequencing core facility. Analysis of the sequencing results was done using BiQAnalyzer™ software.

AAV plasmids and viral vectors production. AAV vector plasmid dsAAV-CBA-ASC was derived from dsAAV-CBA-BGHpA. dsAAV-P0-ASC and dsAAV-P0-Null plasmids were derived from the plasmid dsAAV-P0-ICE. These plasmids carry two AAV inverted terminal repeat (ITR) elements, one wild type and one in which the terminal resolution site was deleted, as described (36), generating a vector that is packaged as a double-stranded molecule. The dsAAV-rP0-null was generated by cutting the ICE transgene off the dsAAV-rP0-ICE using ECORV. The resulted self ligated vector is dsAAV-rP0-null. The dsAAV-P0-ASC plasmid was generated by inserting PCR-amplified hASC (600 bp) into the dsAAV-rP0-null that was linearized with ECORV.

The Primers that were used for ASC amplification contain ECORV restriction site, the sequences are: Forward 5'GTGATATCGCCACCAtGGGGCGCGCGCGCG3' (SEQ ID NO: 18) and reverse 5'AGGATATCCTAGCTCCGCTCCAGGTCCTCC 3' (SEQ ID NO: 19). The dsAAV-CBA-ASC plasmid was produced through inserting PCR-amplified hASC (600 bp) into the dsAAV-CBA-BGHpA that was linearized with HindIII and SpeI.

The Primers that were used for ASC amplification contain HindIII and SpeI restriction site, the sequences are: Forward 5'GTCAAGCTTGCCACCAtgGGGCGCGCGC3' (SEQ ID NO: 20) and reverse 5'CAACTAGTCTAGCTCCGCTCCAGGTCCT3' (SEQ ID NO: 21). All AAV vectors carry the bovine growth hormone polyadenylation signal. The identity of all the cloned transgenes was confirmed by sequencing.

AAV1 serotype vectors were produced by transient co-transfection of 293T cells by calcium phosphate precipitation of vector plasmid (dsAAV-P0-ASC or dsAAV-P0-null), adenoviral helper plasmid pFD6, and a plasmid encoding the AAV1 cap gene (pXR1), as previously described (37). Briefly, AAV vectors were purified by iodixanol gradient centrifugation followed by column chromatography with HiTrap™ Q anion-exchange columns (GE Healthcare, Piscataway, NJ). The virus-containing fractions were concentrated with Centricon 100-kDa molecular weight cutoff (MWCO) centrifugal devices (Millipore, Billerica, MA) and the titer (genome copies [GC]/ml) was determined by real time PCR amplification with primers and probe specific for the bovine growth hormone polyadenylation signal.

Cell viability and toxicity assay. The Cell Titer-Glo™ luminescent cell viability assay (Promega, Madison, WI) was used to determine the number of viable cells in culture on the basis of quantitation of ATP levels, an indicator of metabolically active cells. The kit detects as few as 15 cells per well 10 min after adding reagent and mixing, resulting in cell lysis and the generation of a luminescent signal proportional to the amount of ATP present. Hundred thousand HEI-193, NF2S1 or 08031-9 cells were plated into the wells of 24-well plates and transfected by lipofectamine in triplicate with the AAV-CBA-ASC or AAV1-CBA-GFP. After 24 hr, medium was aspirated off and cells were incubated in 100 ul of fresh medium containing 100 ul of CellTiter-Glo™ reagent for 10 min at room temperature. The luminescence was measured with a luminometer (Dynex Technologies, Chantilly, VA). Cell death was measured by the LDH assay using CytoTox 96 Non-Radioactive Cytotoxicity Assay kit (Promega) according to the manufacturer's instructions.

Western Not analysis. Cells were washed with cold PBS and total protein was extracted with RIPA lysis buffer (Sigma, USA), supplemented with cocktail protease inhibitor. Equal amounts of proteins were separated by 10-12% SDS-PAGE gel and then transferred onto nitrocellulose membranes. After blocking the membranes with 5% fat free milk in TBST for 1 h at room temperature, the membranes were incubated with specific primary antibodies overnight at 4° C. After washing, the membrane was incubated with HRP-conjugated secondary antibodies for 1 h at room temperature and then washed with TBST. The antibody complexes in the immunoblots were detected by chemiluminescence using an ECL (BIORAD, USA), and visualized using a ChemiDoc Gel Documentation System (BIORAD, USA). Antibodies used were rabbit anti caspase 1 (CST, USA), rabbit anti caspase 3 (CST, USA), rabbit anti caspase 7 (CST, USA), mouse anti caspase 9 (CST, USA), mouse anti caspase 8 (CST, USA), rabbit anti BAX (CST, USA), rabbit anti RIP2 (CST, USA), rabbit anti BID (CST, USA), rabbit anti BCL-2 (CST, USA), mouse anti P53 (Sigma, USA) and rabbit anti NFkB p65 (Santa Cruz, USA).

Assay of activated caspases. Caspase 3/7 assays (G8090, Promega) were performed according to the manufacturer's instructions. Briefly, 100,000 cells/well were plated overnight in a 24-well plate. Cells were transfected as described in the cell culture section. To measure caspase 3/7 activity, 100 uL of caspase Glo 3/7 reagent was added to 100 ul cells growing medium to each well for 2 h with constant shaking at room temperature. Caspase8 and 9 assays were done in the same procedure using Caspase 8 Glo assay (G8200, Promega) and caspase 9 Glo assay (G8210, Promega). Luminescence was measured using a Biotek synergy plate reader. Colorimetric caspase-1 activity assay was measured using Caspase-1/ICE Colorimetric Assay Kit (Biovision, USA) according to the manufacturer instructions.

Animals. All animal experimentation was approved by and conducted under the oversight of the Massachusetts General Hospital (Boston, MA) Institutional Animal Care and Use Committee. Animals, nu/nu and C57BL/6 mice, were kept on a 12:12 light-to-dark cycle with ad libitum access to food and water. Animals were checked daily to evaluate health.

Generation of tumors and vector injection. Sciatic nerve schwannomas were generated by direct injection of schwannoma cells into the left sciatic nerve of isoflurane-anesthetized mice, as described (38). Specifically, cells were implanted approximately 4 mm distal to the sciatic notch at a point midway between the sciatic notch and the trifurcation of the sciatic nerve into the common peroneal, tibial, and sural branches. HEI-193FC cells were trypsinized and rinsed with PBS, and 30,000 cells in a volume of 0.5 ul of PBS were injected into the sciatic nerve of athymic nude mice (nu/nu, 5-7 week-old males; National Cancer Institute [NCI]), using a glass micropipette and a gas-powered microinjector (IM-300; Narishige, Tokyo, Japan). Tumor growth was monitored by in vivo bioluminescence imaging at weekly intervals, as described (34). Briefly, mice were injected intraperitoneally with the Fluc substrate d-luciferin, and, 10 min later, signal was acquired with a high efficiency IVIS Spectrum (Caliper Life Sciences, Hopkinton, MA). Tumors were injected with PBS, AAV1-P0-ASC or AAV1-P0-null three weeks post implantation, with 10E10 vector GC in 2 ul PBS, targeting the enlarged part of the nerve where tumor cells were implanted. Volumetric changes in tumors were tracked by in vivo bioluminescence imaging.

Behavioral analysis. The mice were tested by the von Frey method for pain/mechanical sensitivity, Hargreaves plantar test for Pain/Thermal sensitivity and by rotarod for gross motor function according to published methods (39, 40, and 41). Both nu/nu and C57BL were used for the behavioral experiments. Two microlitres of the vector AAV1-P0-ASC, AAV1-P0-null, or PBS were injected into the sciatic nerve (n=8 per group). All animals were allowed to habituate to the behavioral apparatus for 1 week before testing for baseline. Three baseline measurements on three separate days preceded the first injection. Mice were then tested the day after each injection and twice per week for 8 weeks. Mechanical sensitivity of the hind paw was measured by determining withdrawal thresholds assessed with von Frey filaments employed to determine mechanical sensitivity of the plantar surface of the hind paw, as described in (Prabhakar et. al 2013). The 50% threshold for each paw withdrawal was calculated, as previously described (42). Thermal sensitivity of the hind paw was measured by determining withdrawal latency assessed with Hargreaves plantar test, as described (41). A rotating rod apparatus (Columbus Instruments, Columbus, OH) was used to assess motor performance. Mice were placed on the elevated accelerating rod beginning at 1 rpm/min for two trials per day twice per week. Animals fall latency (in seconds) was scored, as described (Prabhakar et. al 2013).

Apoptosis assay. In-vitro DNA fragmentation of apoptotic cells was assessed TACS® 2 TdT-DAB in Situ Apoptosis Detection Kit. In brief, HEI-193 cells on the coated cover glass and transfected with dsAAV-CBA-ASC or dsAAV-CBA-GFP. Fragmented DNA were visualized with diaminobenzidine (DAB) and viewed by light microscope. In-vivo apoptosis study was assessed using the same kit on fresh frozen nerves that were sliced to 15 um thin sections using cryostat and fixed in 3.7% formaldehyde.

Histological and Immunohistochemistry analysis. After treatment with vectors, the animals were anesthetized with isoflurane (3%) followed by decapitation. Sciatic nerves were taken out and snap frozen for hematoxylin and eosin (H&E) and immunohistochemistry staining, as described (43). The sciatic nerves were kept in OCT blocks at –80° C. Sections were stained with H&E in accordance with routine protocols. Proliferation marker staining was performed using antibody against Ki67 (Abcam, USA). Briefly, sections were dried at RT overnight. They were fixed in pre-chilled acetone for 10 minutes before re-drying them at room temperature prior to the staining. Sections were washed in PBS, blocked for endogenous background with protein block serum free (Dako, USA) and quenched for peroxidases in Dual endogenous enzyme block (DAKO, USA). Sections were washed in PBS then incubated with primary antibody against Ki67 for 1 hour at room temperature. They were washed in PBS and incubated with secondary antibody conjugated with horseradish peroxidase for thirty minutes at room temperature. Sections were washed in PBS, incubated with DAB solution (DAKO, USA) for few minutes. Counterstaining was done by dipping the sections in ethanol and xylene before mounting in cytoseal and covered by cover slips for microscopic visualization.

Data analysis. All data are presented as group averages±SEM. The baseline value for all tests before injection used the average of all measurements before injection. Data were analyzed with graphpad prism and Microsoft EXCEL. The significance of differences between two groups was determined using a two-tailed t-test. Repeated-measure analysis of variance (ANOVA) was used when data were collected in multiple trials, as described (44). $p < 0.05$ was accepted as significant.

REFERENCES

1. Lu-Emerson, C. and S. R. Plotkin, The neurofibromatoses. Part 2: NF2 and schwannomatosis. Rev Neurol Dis, 2009. (3): p. E81-6.
2. Evans, D. G., Neurofibromatosis type 2 (NF2): a clinical and molecular review. Orphanet J Rare Dis, 2009: p. 16.
3—Antinheimo, J., Sankila, R., Carpe'n, O., et al. (2000). Population based analysis of sporadic and type 2 neurofibromatosis associated meningiomas and schwannomas. Neurology 54, 71-76
4. Trofatter J A, MacCollin M M, Rutter J L, Murrell J R, Duyao M P, Parry D M, et al. A novel moesin-, ezrin-, radixin-like gene is a candidate for the neurofibromatosis 2 tumor suppressor. Cell 1993; 72:791-800.
5. Rouleau G A, Merel P, Lutchman M, Sanson M, Zucman J, Marineau C, et al. Alteration in a new gene encoding a putative membrane-organizing protein causes neuro-fibromatosis type 2. Nature 1993; 363:515-21.
6. Bretscher A, Edwards K, Fehon R G. ERM proteins and merlin: integrators at the cell cortex. Nat Rev 2002; 3:586-99.
7. Lutchman M, Rouleau G A. The neurofibromatosis type 2 gene product, schwannomin, suppresses growth of NIH 3T3 cells. Cancer Res 1995; 55:2270-4.
8. Schulze K M, Hanemann C O, Muller H W, Hanenberg H. Transduction of wild-type merlin into human schwannoma cells decreases schwannoma cell growth and induces apoptosis. Hum Mol Genet 2002; 11: 69-76.
9—Hung, G., Li, X., Faudoa, R., et al. (2002). Establishment and characterization of a schwannoma cell line from a patient with neurofibromatosis 2. Int. J. Oncol. 20, 475-482
10—Prabhakar, S., Brennan, G. J., Messerli, S. M., et al. (2010). Imaging and therapy of experimental schwannomas using HSV amplicon vector-encoding apoptotic protein under Schwann cell promoter. Cancer Gene Ther. 17, 266-274.
11—Saydam, O., Ozdener, G. B., Senol, O., et al. (2011). A novel imaging-compatible sciatic nerve schwannoma model. J. Neurosci. Methods 195, 75-77
12—Shilpa Prabhakar, Gary J. Brenner, et al. (2013). Regression of Schwannomas Induced by Adeno-Associated Virus-Mediated Delivery of Caspase-1. Hum Gene Ther 24:152-162
13—Schroder K, Tschopp J. 2010. The inflammasomes. Cell 140: 821-832.
14—Strowig T, Henao-Mejia J, Elinav E, Flavell R. 2012. Inflammasomes in health and disease. Nature 481: 278-286.
15—de Zoete M R, Flavell R A. 2013. Interactions between Nodlike receptors and intestinal bacteria. Front Immunol 4:462.
16—Latz E, Xiao T S, Stutz A. 2013. Activation and regulation of the inflammasomes. Nat Rev Immunol 13: 397-411
17—McConnell B B, Vertino P M. TMS1/ASC: the cancer connection. APOPTOSIS. 2004; 9:518.
18—Conway K E, McConnell B B, Bowring C E, Donald C D, Warren S T, Vertino P M (2000) TMS1, a novel proapoptotic caspase recruitment domain protein, is a target of methylation-induced gene silencing in human breast cancers. Cancer Res 60:6236-6242

19—McConnell B B, Vertino P M. Activation of a caspase-9-mediated apoptotic pathway by subcellular redistribution of the novel caspase recruitment domain protein TMS1. CANCER RES. 2000; 60:6243-6247

20—Masumoto J, Dowds T A, Schaner P, Chen F F, Ogura Y, Li M, Zhu L, Katsuyama T, Sagara J, Taniguchi S, Gumucio D L, Nunez G, Inohara N. ASC is an activating adaptor for NF-kappa B and caspase-8-dependent apoptosis. BIOCHEM BIOPHYS RES COMMUN. 2003; 303: 69-73

21—Jeoffrey J Levine 1, Krista M Stimson-Crider 1 and Paula M Vertino. Effects of methylation on expression of TMS1/ASC in human breast cancer cells. Oncogene (2003) 22, 3475-3488

22—Kerry E. Conway, 2 Beth B. McConnell, 2 Claire E. Bowring, Carlton D. Donald, Stephen T. Warren, and Paula M. Vertino 3. TMS1, a Novel Proapoptotic Caspase Recruitment Domain Protein, Is a Target of Methylation-induced Gene Silencing in Human Breast Cancers 1. CANCER RESEARCH 60, 6236-6242, Nov. 15, 2000

23—Partha M Das1, Kavitha Ramachandran 1, Jane VanWert 1, Larry Ferdinand 1, Gopal Gopisetty 1, Isildinha M Reis 1 and Rakesh Singal. Methylation mediated silencing of TMS1/ASC gene in prostate cancer. Molecular Cancer 2006, 5:28ol 24—Guan X, Sagara J, Yokoyama T, Koganehira Y, Oguchi M, Saida T, Taniguchi S: ASC/TMS1, a caspase-1 activating adaptor, is down regulated by aberrant methylation in human melanoma. Int J Cancer 2003, 107:202-208.

25—Stone A R, Bobo W, Brat D J, Devi N S, Van Meir E G, Vertino P M: Aberrant methylation and down-regulation of TMS1/ASC in human glioblastoma. Am J Pathol 2004, 165:1151-1161.

26—D. M. Kordi Tamandani 1,2, R. C. Sobti 1, M. Shekari 1,3, A. Huria 4 CPG ISLAND METHYLATION OF TMS1/ASC AND CASP8 GENES IN CERVICAL CANCER. Eur J Med Res (2009) 14: 71-75

27—KAVITHA RAMACHANDRAN*, HEATHER MILLER*, EDNA GORDIAN, CAIO ROCHA-LIMA and RAKESH SINGAL. Methylation-mediated Silencing of TMS1 in Pancreatic Cancer and its Potential Contribution to Chemosensitivity. ANTICANCER RESEARCH 30: 3919-3926 (2010

28—C Zhang, 1# H Li, 2# G Zhou, 1* Q Zhang, 1 T Zhang, 1 J Li, 1 J Zhang, 1 J Hou, 1 CT Liew 2 and D Yin3. Transcriptional silencing of the TMS1/ASC tumour suppressor gene by an epigenetic mechanism in hepatocellular carcinoma cells. J Pathol 2007; 212: 134-142

29—Dhillon V S, Aslam M, Husain S A: The contribution of genetic and epigenetic changes in granulosa cell tumors of ovarian origin. Clin Cancer Res 2004, 10:5537-5545.

30—Terasawa K, Sagae S, Toyota M, Tsukada K, Ogi K, Satoh A, Mita H, Imai K, Tokino T, Kudo R: Epigenetic inactivation of TMS1/ASC in ovarian cancer. Clin Cancer Res 2004, 10:2000-2006.

31—Hung, G., Li, X., Faudoa, R., et al. (2002). Establishment and characterization of a schwannoma cell line from a patient with neurofibromatosis 2. Int. J. Oncol. 20, 475-482.

32—S Prabhakar 1,2, S M Messerli 1,2,5, A O Stemmer-Rachamimov 3, T-C Liu4, S Rabkin 4, R Martuza 4 and XO Breakefield. Treatment of Implantable NF2 Schwannoma Tumor Models with Oncolytic Herpes Simplex Virus G47D. Cancer Gene Therapy (2007) 14, 460-467.

33—Karo Tanaka 1, Ascia Eskin 3, Fabrice Chareyre 1, Walter J. Jessen 6, Jan Manent 7, Michiko Niwa-Kawakita 8, Ruihong Chen 5, Cory H. White 2, Jeremie Vitte 1, Zahara M. Jaffer 1, Stanley F. Nelson 3, Allan E. Rubenstein 9, and Marco Giovannini 1. Therapeutic Potential of HSP90 Inhibition for Neurofibromatosis Type 2. Clin Cancer Res 2013; 19:3856-3870

34—S Prabhakar 1,2,3, G J Brenner 1,4, B Sung 1,5, SM Messerli 1,2,3,8, J Mao1,5, M Sena-Esteves 1,2,3, A Stemmer-Rachamimov 1,6, B Tannous 1,2,7, and XO Breakefield 1,2,6,7 Imaging and therapy of experimental schwannomas using HSV amplicon vector-encoding apoptotic protein under Schwann cell promoter. Cancer Gene Ther. 2010 April; 17(4): 266-274

35—Xiao-Fang Liu, Shi-Guang Zhu, Hao Zhang, Zheng Xu, Hai-Long Su, Shao-Jun Li and Xian-Ting Zhou. The methylation status of the TMS1/ASC gene in cholangiocarcinoma and its clinical significance. Hepatobiliary Pancreat Dis Int 2006; 5: 449-453

36—McCarty, D. M., Fu, H., Monahan, P. E., et al. (2003). Adenoassociated virus terminal repeat (TR) mutant generates self complementary vectors to overcome the rate-limiting step to transduction in vivo. Gene Ther. 10, 2112-2118

37—Broekman, M. L., Comer, L. A., Hyman, B. T., and Sena-Esteves, M. (2006). Adeno-associated virus vectors serotyped with AAV8 capsid are more efficient than AAV-1 or -2 serotypes for widespread gene delivery to the neonatal mouse brain. Neuroscience 138, 501-510.

38—Saydam, O., Ozdener, G. B., Senol, O., et al. (2011). A novel imaging-compatible sciatic nerve schwannoma model. J. Neurosci. Methods 195, 75-77.

39—Agarwal, N., Pacher, P., Tegeder, I., et al. (2007). Cannabinoids mediate analgesia largely via peripheral type 1 cannabinoid receptors in nociceptors. Nat. Neurosci. 10, 870-879

40—Kirschbaum, K. M., Hiemke, C., and Schmitt, U. (2009). Rotarod impairment: Catalepsy-like screening test for antipsychotic side effects. Int. J. Neurosci. 119, 1509-1522

41—Hargreaves K, Dubner R, Brown F, Flores C, Joris J. A new and sensitive method for measuring thermal nociception in cutaneous hyperalgesia. Pain. 1988; 32:77-88

42—Chen, Q., Peto, C. A., Shelton, G. D., et al. (2009). Loss of modifier of cell adhesion reveals a pathway leading to axonal degeneration. J. Neurosci. 29, 118-130

43—Messerli, S. M., Tang, Y., Giovannini, M., et al. (2002). Detection of spontaneous schwannomas by MRI in a transgenic murine model of neurofibromatosis type 2. Neoplasia 4, 501-509

44—Harris, J. E., Sheean, P. M., Gleason, P. M., et al. (2012). Publishing nutrition research: A review of multivariate techniques. 2. Analysis Example 3

Figure 11:
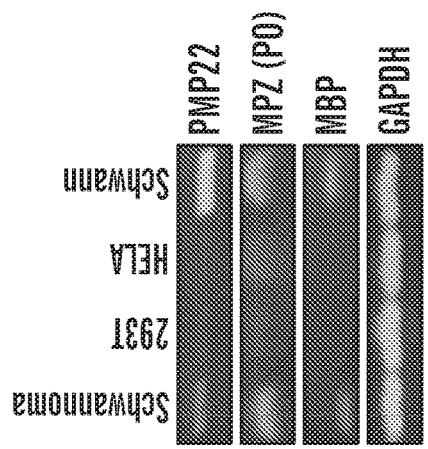
FIG. 11 depicts the level of expression driven by the indicated promoters in a variety of cell types.

FIG. 11 demonstrates the expression driven by different schwannoma promoters in the indicated cell types. The PMP22, P0, and MBP promoters demonstrate schawnn cell-specific expression.

Example 4

Figure 12:
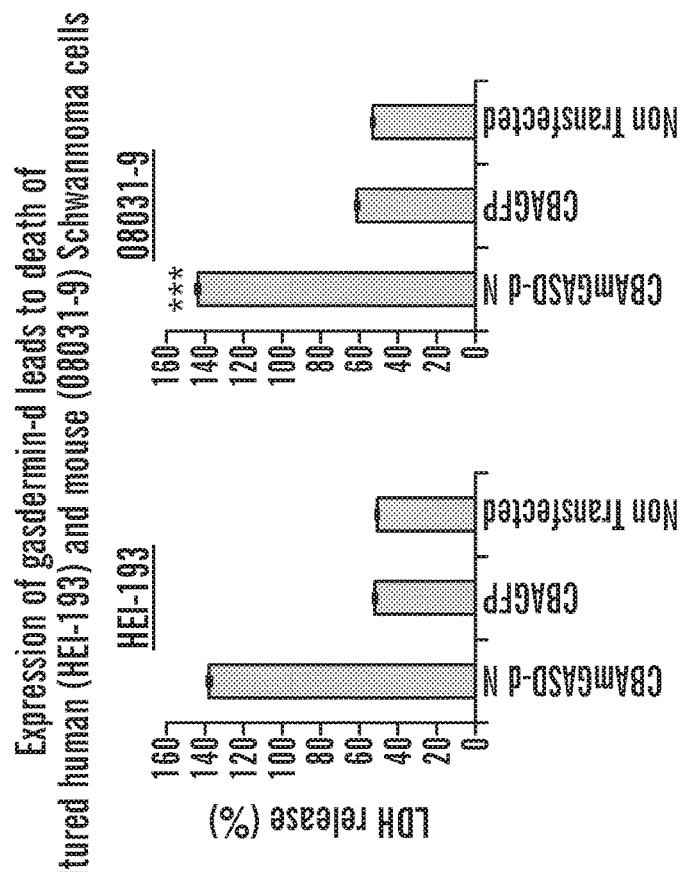
FIG. 12 demonstrates that delivery of gasdmerin D-expressing constructs kills both HEI-193 (human) and 08031-9 (mouse) schwannoma cells.
Figure 12:
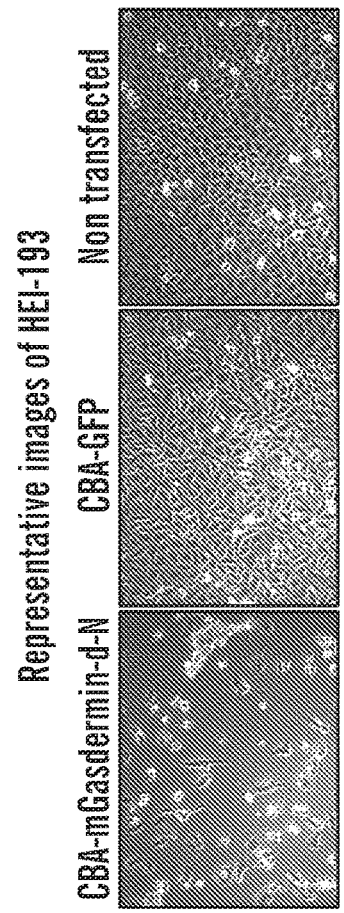

Gasdermin D expression in schwannomas was demonstrated to kill the schwannoma cells (FIG. 12). Gasdermin D was delivered using mouse and/or human gasdermin D under the control of the CBA promoter in an AAV vetor. In the experiments depicted in FIG. 12, the portion of gasdermin D which is N-terminal of the caspase cleavage site (e.g., after Asp275 in human gasdermin D or Asp276 in mouse gasdermin D) was utilized.

Example 5

Figure 13:
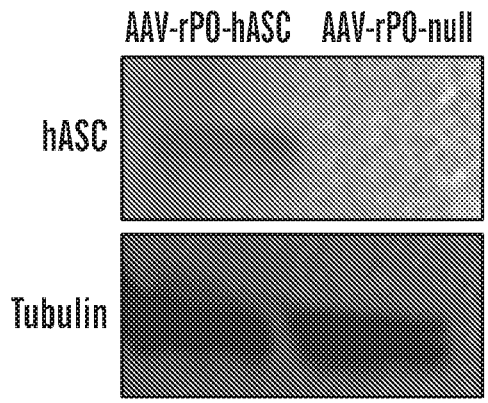
FIG. 13 demonstrates expression Of ASC upon injection of AAV1-rP0-hASC into Schwannoma mouse model.
Figure 14:
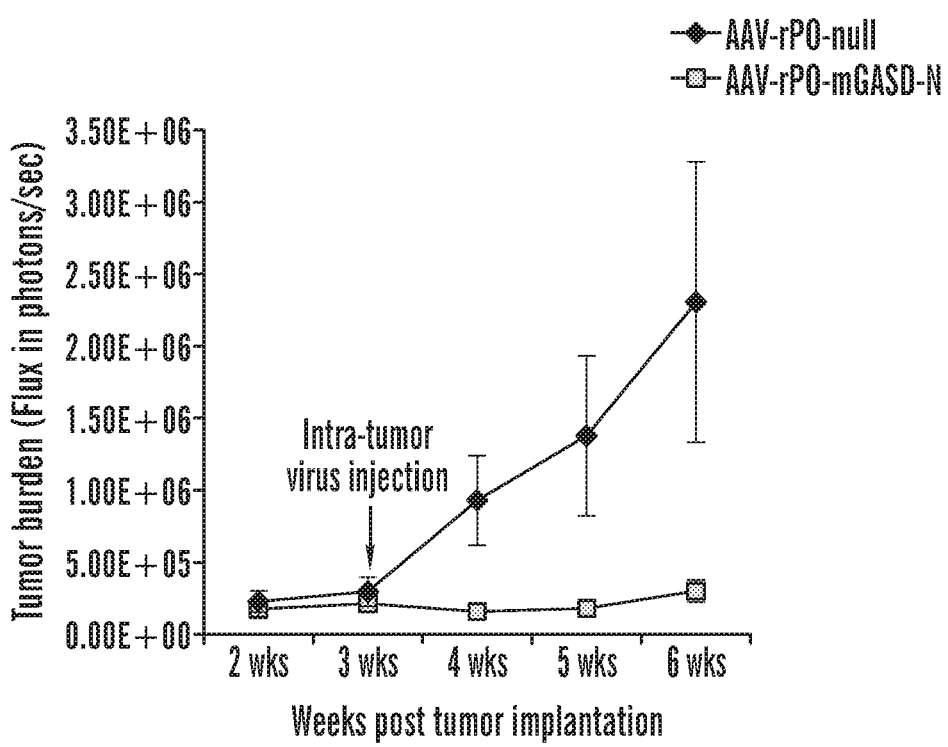
FIG. 14 depicts a graph of the effect of viral gasdermin-d delivery on growth of intra-sciatic human HEI-193 Schwannoma tumors.
Figure 15A:
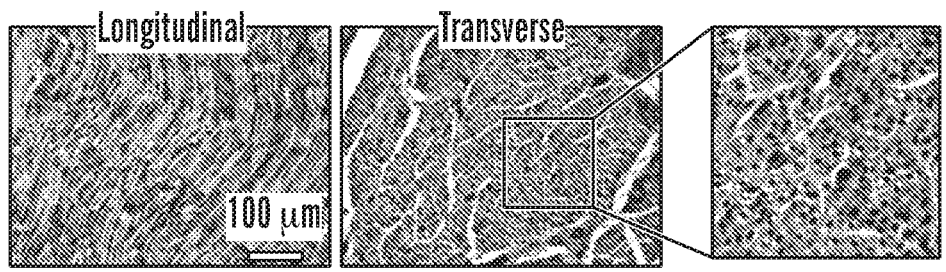
Figure 15A:
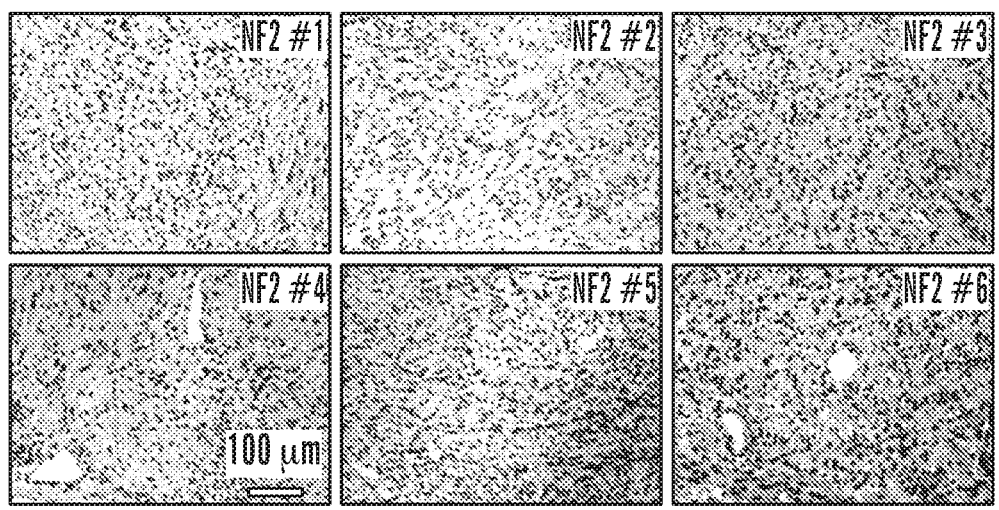
Figure 15D:
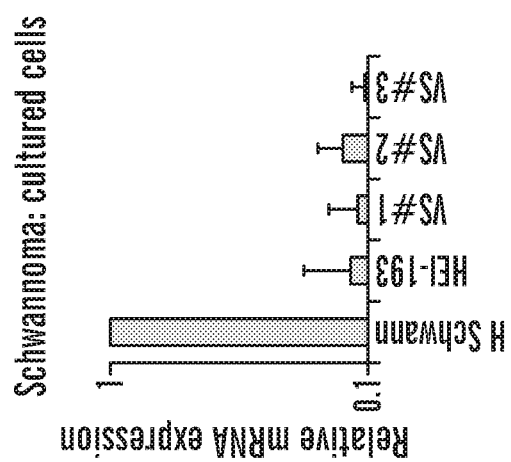
Figure 15C:
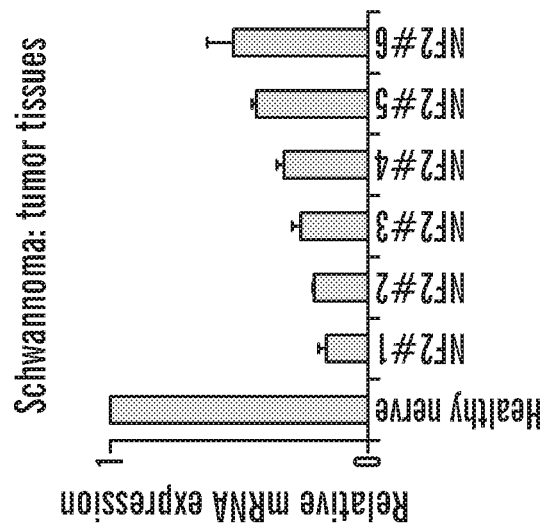
Figure 15B:
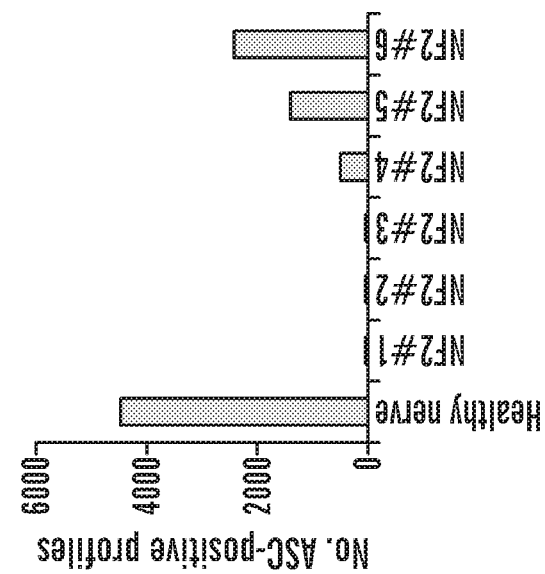
Figure 16B:
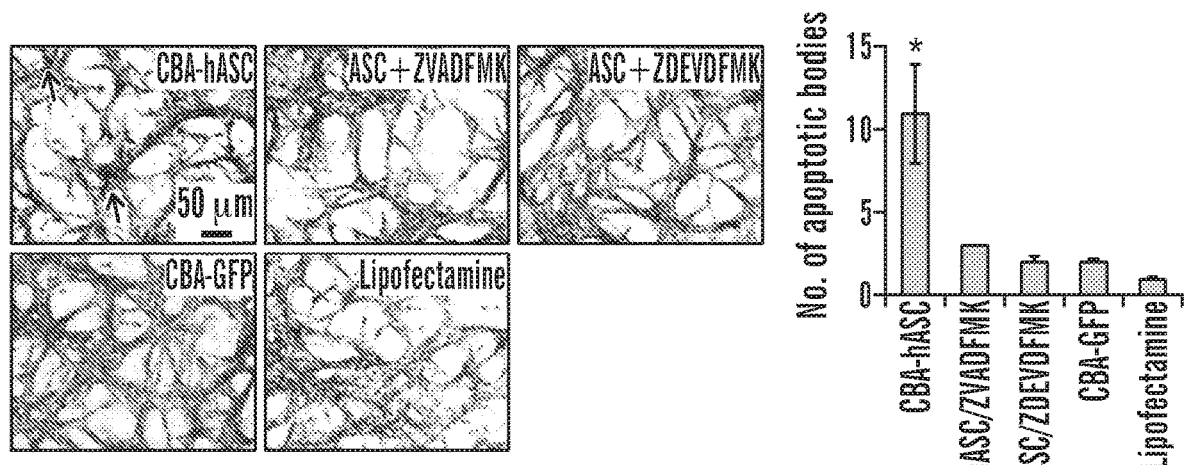
Figure 16C:
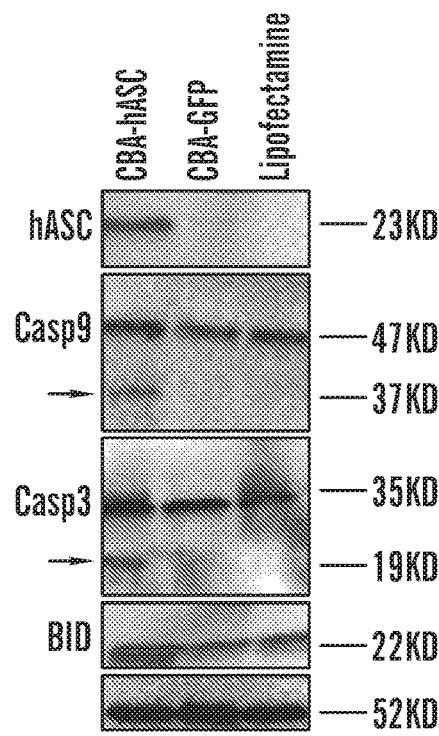
Figure 16D:
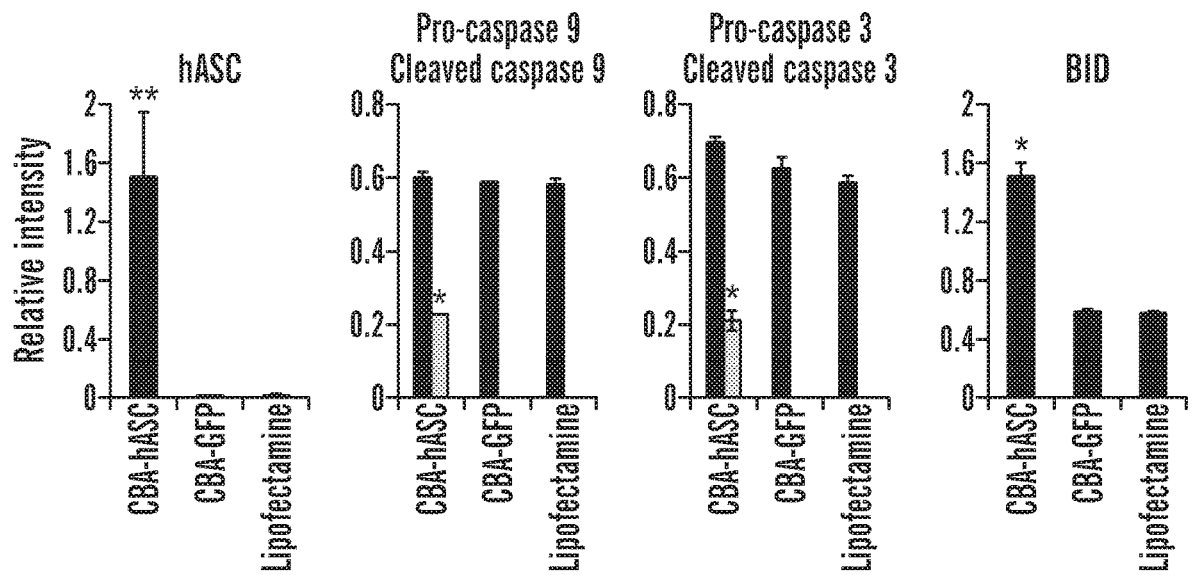
Figure 16E:
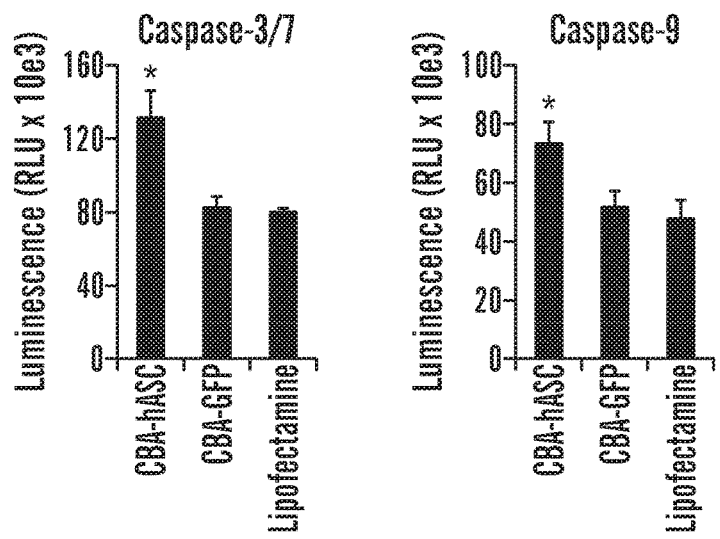

The expression of ASC upon injection of AAV1-rP0-hASC into Schwannoma mouse model is demonstrated in FIG. 13. HEI-193FC cells were implanted into nude mice. AAV1-rP0-hASC or AAV1-rP0-null ws injected at three weeks post implantation. Nerves were harvested for protein extraction 1 week after injection. Protein levels were quantified by western blotting. The results demonstrate increased human ASC protein expression following injection of AAV-P0-ASC into intrasciatic HEI-193 tumors.

Example 6

2×109 pfu's of virus (in a volume of 2 microliters) was delivered via direct injection into HEI-193 tumors growing in the left sciatic nerve of nu/nu mice. Error bars show SEM. N=7-8 mice per group. ANOVA indicated a significant effect of AAV-rP0-mGASD-N treatment compared to control virus at a significance level of p=0.0016. There was no significant interaction between treatment and time post virus injection (p=0.68).

Example 7

Figure 18:
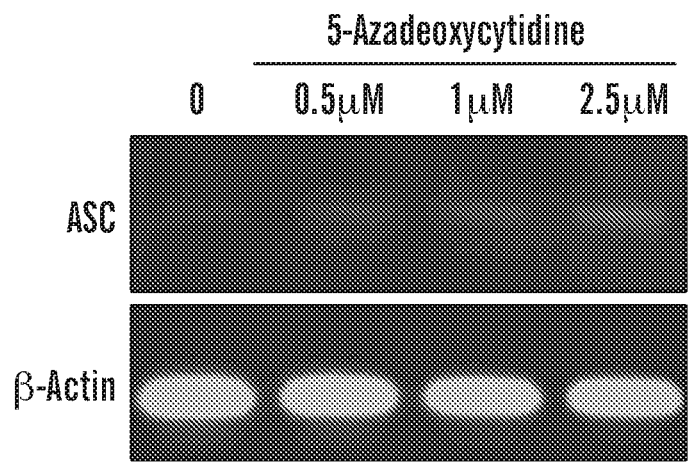
FIG. 18 demonstrates that demethylation of the ASC CpG island restores expression in ASC-negative HEI-193 cell line. The cultured cells were treated with (5azadeoxycytindine 0.5, 1 or 2.5 uM) or not treated (0) for 3 days. The samples were analyzed for ASC expression by RT-PCR and normalized to β-actin.

ASC expression is decreased in schwannomas, e.g., as compared to healthy peripheral nerve cells (FIGS. 15A-15G). The downregulation of ASC was observed in cell lines and primary schwannoma cells (including 6 different human schwannomas). The decrease in expression correlates to promoter methylation and the methylation is reversible, e.g., when treated with 5azadeoxycytidine (FIG. 18).

Figure 17A:
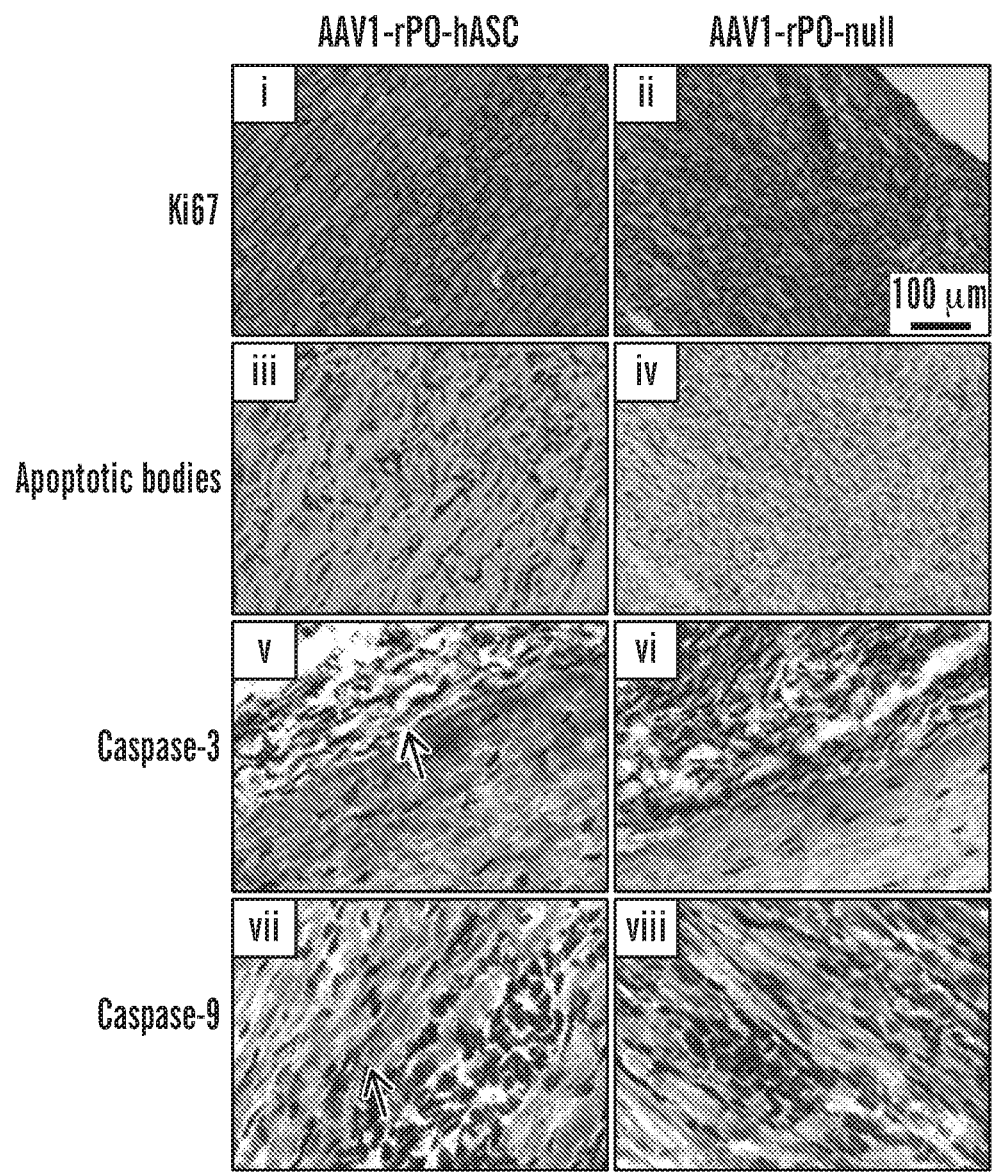
FIGS. 17A-17C demonstrate that AAV1-rP0-hASC in vivo therapy of schwannoma increases markers of apoptosis and reduces markers of cell proliferation.
Figure 17B:
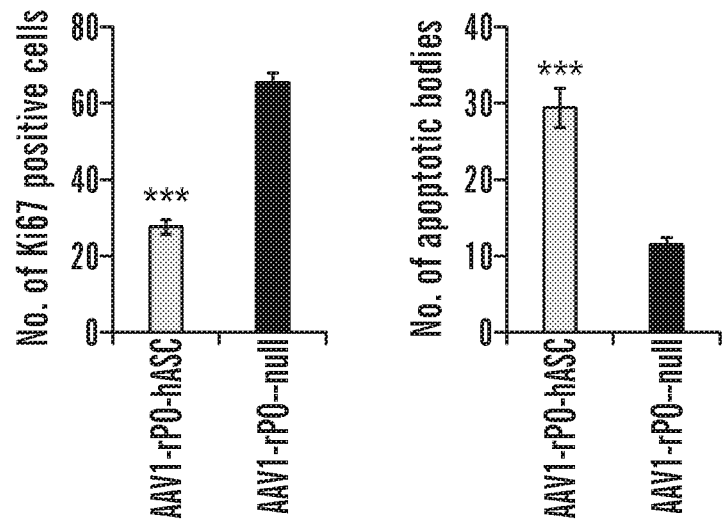
Figure 17C:
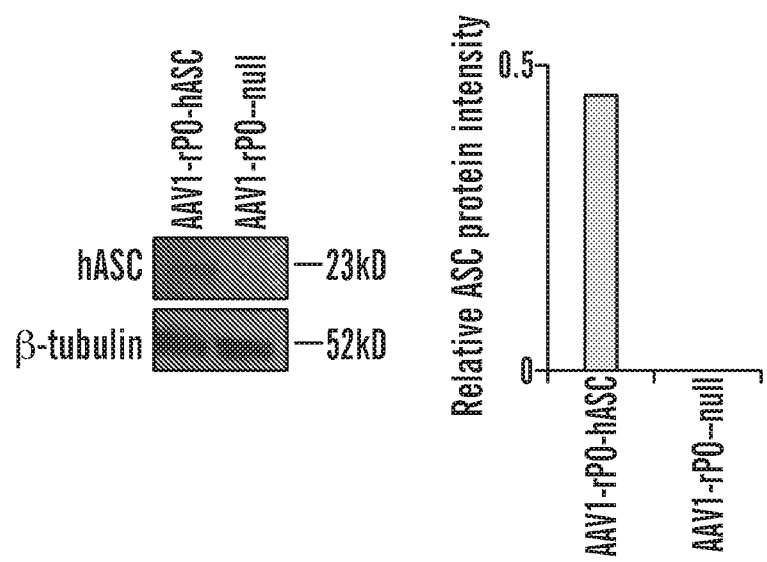

Overexpression of ASC via transfection with pAAV-CBA-hASC in schwannoma cells leads to increased levels of cell death (in multiple cell lines (FIGS. 16A-16E). In vivo therapy with AAV1-rP0-hASC increases markers of apoptosis (caspase-3 and caspase-9 expression) and reduces markers of cell proliferation (e.g., Ki67) (FIGS. 17A-17C).

Figure 19:
FIG. 19 depicts a graph demonstrating fully humanized vector (AAV1-hP0-hASC) inhibits schwannoma growth and that there is no difference in efficacy compared with rat P0 containing vector (AAV1-rP0-hASC).
Figure 19:
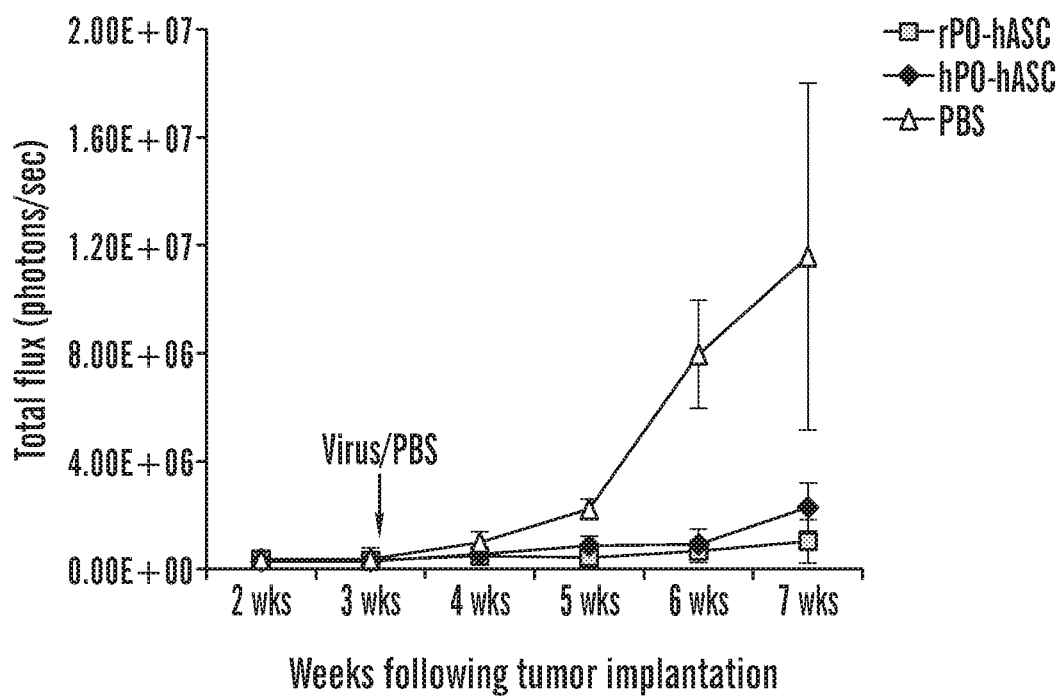
Figure 20A:
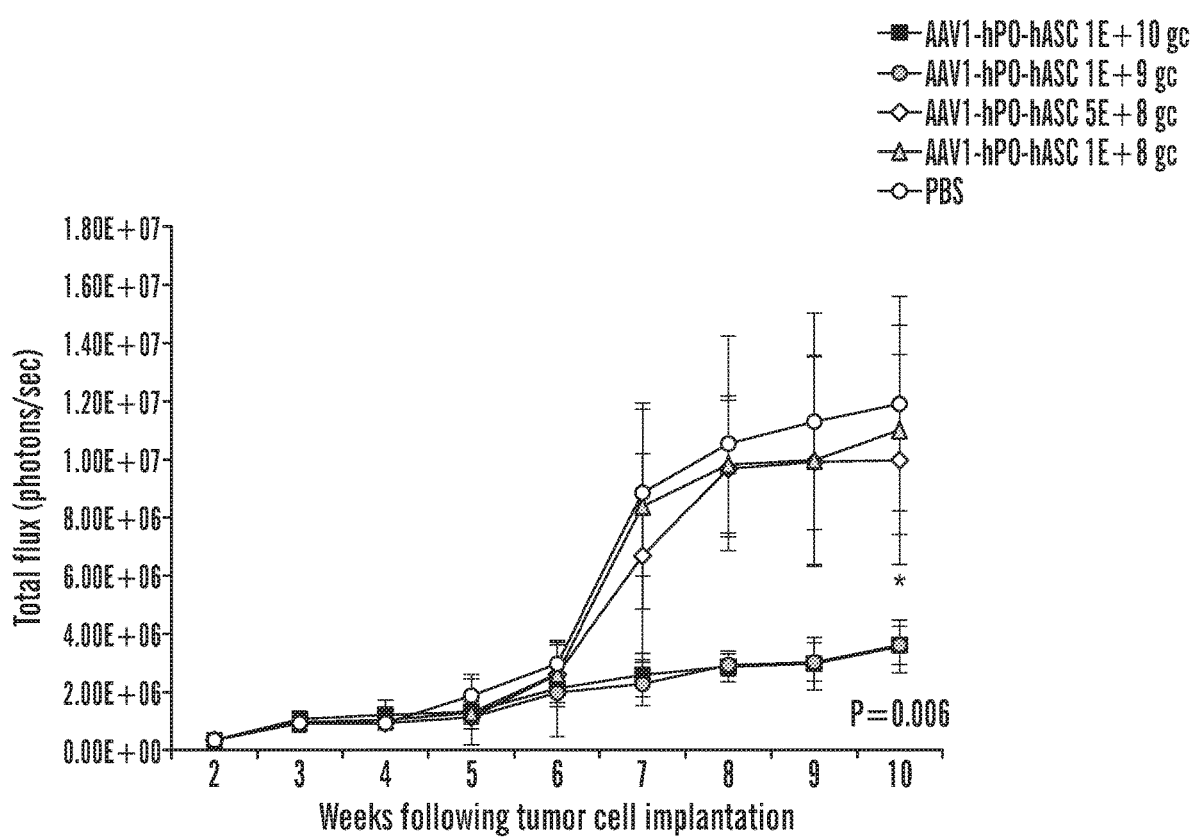
FIG. 20A depicts a graph of the Minimum Effective Dose of fully humanized product: AAV1-hP0-hASC.
Figure 20B:
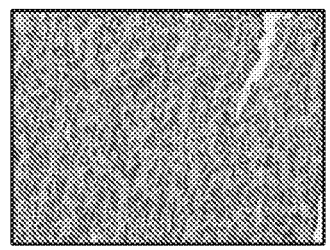
FIG. 20B depicts the supporting histological data.
Figure 20B:
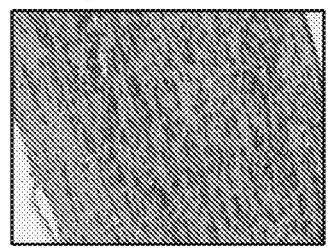
Figure 20B:
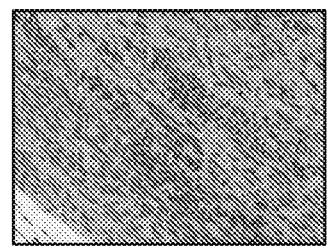
Figure 20B:
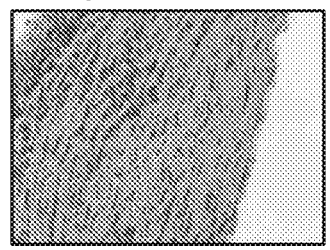
Figure 20B:
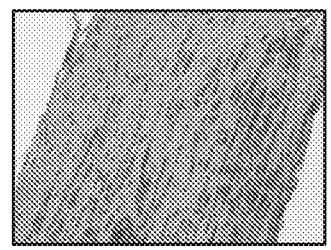
Figure 21A:
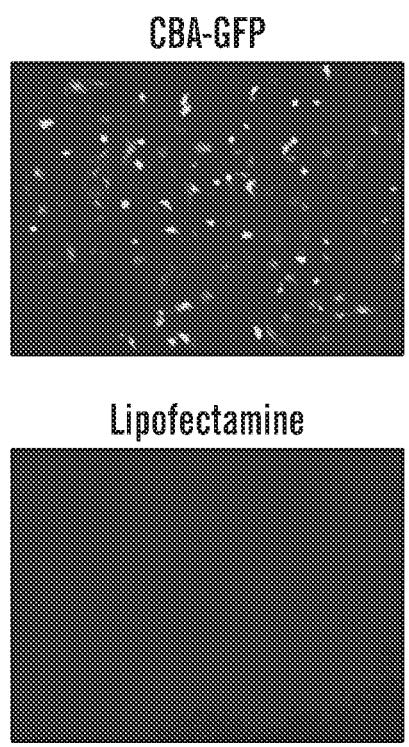
FIGS. 21A-21B demonstrate that in vitro transduction of mouse plexiform neurofibroma (NF-1 tumor) cells with ASC and gasdermin-d (GASD), but not caspase-1 (ICE), leads to cell death.
Figure 21B:
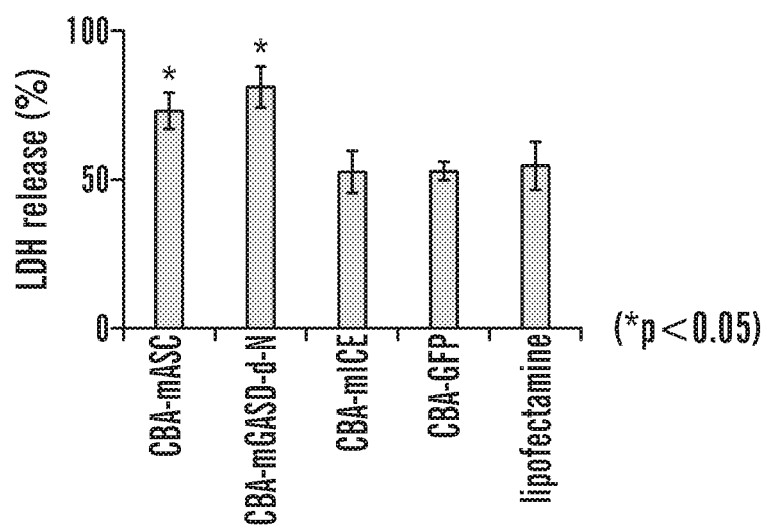
Figure 22A:
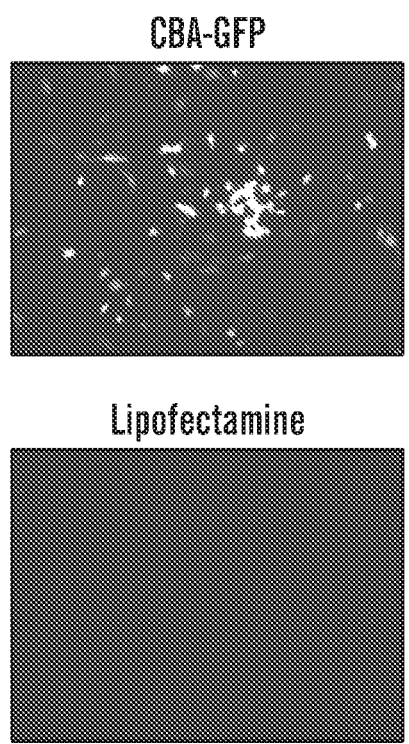
FIGS. 22A-22B demonstrate that in vitro transduction of S462. Ty cells (human malignant peripheral nerve sheath tumor (MPNST) derived and NF1 deficient) cells with ASC and gasdermin-d (GASD), but not caspase-1 (ICE), leads to cell death.
Figure 22B:
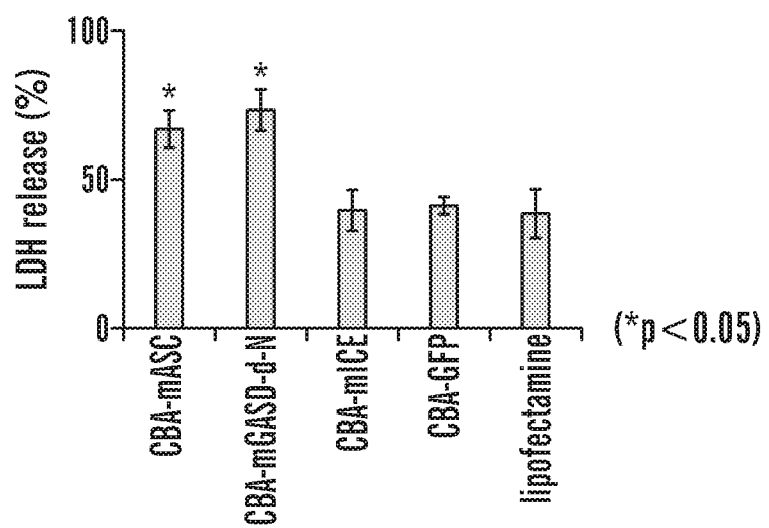
Figure 23A:
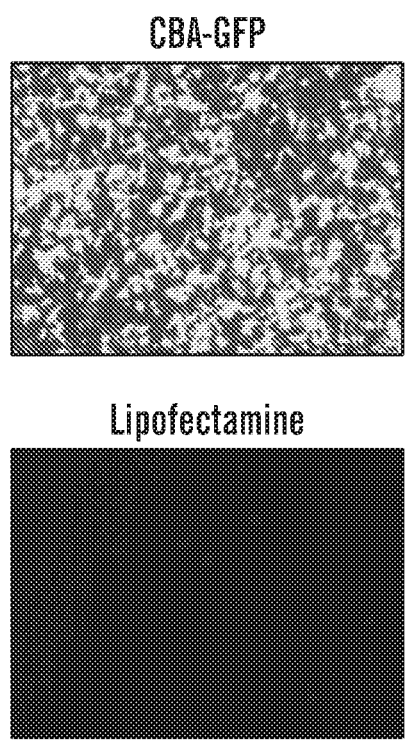
FIGS. 23A-23B demonstrate that in vitro transduction of STS-26T (human sporadic MPNST derived and NF1 proficient) cells with ASC and gasdermin-d (GASD), but not caspase-1 (ICE), leads to cell death.
Figure 23B:
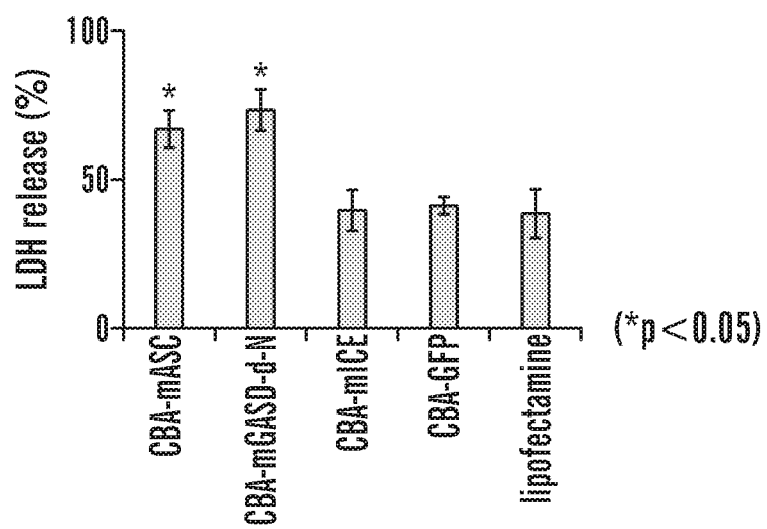

The therapeutic compositions described herein were demonstrated to provide efficacy with both the rat and human P0 promoters (FIG. 19). A minimal effective dose response curve is provided in FIG. 20A.

The methods and compositions described herein were demonstrated to effectively treat NF1-associated tumors, malignant peripheral nerve sheath tumor cells (both NF1 deficient and proficient) by overexpressing ASC or GASD-d. Interestingly, vectors comprising caspase-1 (ICE) did not prove effiacacious in this model (FIGS. 21A-21B, 22A-22B, and 23A-23B).

Figure 24A:
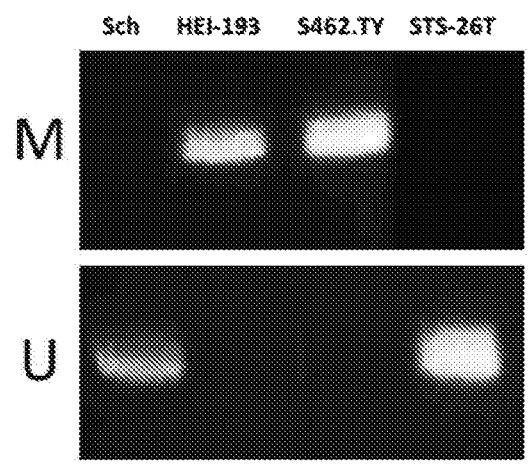
FIGS. 24A and 24B depict data of ASC promoter methylation (FIG. 24A; methylation specific-PCR) and ASC mRNA expression (FIG. 24B; real time Q-PCR) in Human Malignant Peripheral Nerve Sheath Tumor (MPNST) cell lines and controls.
Figure 24B:
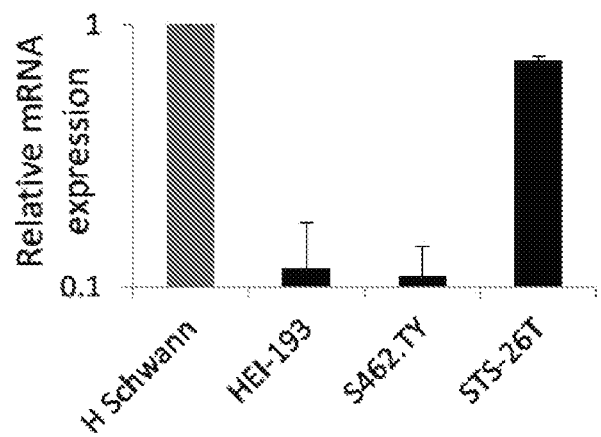

In a NF1-deficient human tumor cell line, the ASC promoter is highly methylated (FIGS. 24A-24B). ASC promoter is demonstrated to be completely methylated in S462. TY cells (human MPNST, NF1-deficient) and completely unmethylated in STS-26T cells (human sporadic MPNST, NF1-proficient). Such methylation typically suppresses expression of ASC. This finding supports the therapeutic applicability of the methods and compositions described herein, e.g., AAV-P0-ASC therapies.

In in vitro experiments, human NF1-deficient tumor cells* with methylated ASC promoter display heavy suppression of ASC mRNA levels (FIGS. 24A-24B). This is significant as it indicates that ASC can be suppressed in NF1-deficient tumor cells in vivo, which in turn, supports the concept of delivering ASC as gene therapy transgene as demonstrated herein with the NF2 schwannoma model. (*the cell line is derived from a human malignant peripheral nerve sheath tumor (MPNST). Of interest and as shown, in a human MPNST cell line in which ASC promoter is NOT methylated, ASC mRNA is highly expressed).

What is claimed herein is:

1. A method of treating a schwannoma in a subject in need thereof, the method comprising:
   administering a viral vector comprising a nucleic acid encoding Apoptosis-associated Speck-like protein containing a CARD (ASC) operably linked to a Schwann cell-specific promoter; and
   wherein the subject is not administered a viral vector comprising a caspase gene.

2. The method of claim 1, wherein the ASC is a human, mouse, or rat ASC.

3. The method of claim 1, wherein the Schwann cell-specific promoter is a myelin basic protein (P0), a peripheral myelin protein 22 (PMP22), or a myelin basic protein (MBP) promoter.

4. The method of claim 1, wherein the promoter is a human or murine promoter.

5. The method of claim 1, wherein the subject in need of treatment for a schwannoma is a subject having or diagnosed as having a condition selected from the group consisting of: neurofibromatosis 1 (NF1); neurofibromatosis 2 (NF2); schwannomatosis; meningioma; nerve sheath tumor; schwannoma; vestibular schwannoma; sporadic schwannoma; neurofibrosarcoma; neurofibroma; neurofibromatosis (NF); malignant peripheral nerve sheath tumor; and a combination thereof.

6. The method of claim 1, wherein the viral vector is a recombinant adeno-associated virus (rAAV).

7. The method of claim 6, wherein the rAAV is of serotype AAV1 or AAV9.

8. The method of claim 1, wherein the vector further comprises a polyadenylation signal.

9. The method of claim 8, wherein the polyadenylation signal comprises a bovine growth hormone polyadenylation signal (BGHpA), a SV40 polyadenylation signal or a rabbit beta-globin polyadenylation signal.

10. The method of claim 8, wherein the vector further comprises a first AAV inverted terminal repeat (ITR) located upstream of the Schwann cell specific promoter and a second AAV ITR located downstream of the polyadenylation signal.

11. The method of claim 10, wherein the first or second AAV inverted terminal repeat comprises a deletion of a terminal resolution site.

12. The method of claim 1, wherein the vector is a polynucleotide.

13. The method of claim 1, wherein the vector is a single-stranded or double-stranded AAV.

14. The method of claim 1, wherein the vector is a self-complementary AAV (scAAV).

15. The method of claim 1, wherein the vector is a virus particle.

16. The method of claim 1, wherein the vector is administered directly to a nerve affected by the schwannoma.

17. The method of claim 1, wherein administering is intranervously, intracranially, intratumorally, intramuscularly, intravenously, intradermally, or subcutaneously, or a combination thereof.

18. The method of claim 1, wherein the subject is also treated by surgical removal or reduction of the schwannoma.

19. The method of claim 1, wherein the subject in need of treatment for a schwannoma is a subject having or diagnosed as having a condition selected from the group consisting of: neurofibromatosis 1 (NF1); neurofibromatosis 2 (NF2); schwannomatosis; meningioma; nerve sheath tumor; schwannoma; vestibular schwannoma; sporadic schwannoma; neurofibrosarcoma; neurofibroma; neurofibromatosis (NF); and a combination thereof.

20. The method of claim 1, wherein the subject is also treated by surgical removal of the schwannoma.

21. The method of claim 1, wherein the schwannoma is benign.

* * * * *

SEQUENCE LISTING

```
<160> NUMBER OF SEQ ID NOS: 22

<210> SEQ ID NO 1
<211> LENGTH: 782
<212> TYPE: DNA
<213> ORGANISM: Homo sapiens

<400> SEQUENCE: 1
gtccaggttc cgccccggag ccgacttcct cctggtcggc ggctgcagcg gggtgagcgg      60
cggcagcggc cggggatcct ggagccatgg ggcgcgcgcg cgacgccatc ctggatgcgc     120
tggagaacct gaccgccgag gagctcaaga agttcaagct gaagctgctg tcggtgccgc     180
tgcgcgaggg ctacggcgc atcccgcggg gcgcgctgct gtccatggac gccttggacc     240
tcaccgacaa gctggtcagc ttctacctgg agacctacgg cgccgagctc accgctaacg     300
tgctgcgcga catgggcctg caggagatgg ccgggcagct gcaggcggcc acgcaccagg     360
gctctggagc cgcgccagct gggatccagg cccctcctca gtcggcagcc aagccaggcc     420
tgcactttat agaccagcac cgggctgcgc ttatcgcgag ggtcacaaac gttgagtggc     480
tgctggatgc tctgtacggg aaggtcctga cggatgagca gtaccaggca gtgcgggccg     540
agcccaccaa cccaagcaag atgcggaagc tcttcagttt cacaccagcc tggaactgga     600
cctgcaagga cttgctcctc caggccctaa gggagtccca gtcctacctg gtggaggacc     660
tggagcggag ctgaggctcc ttcccagcaa cactccggtc agcccctggc aatcccacca     720
```

-continued

```
aatcatcctg aatctgatct ttttatacac aatatacgaa aagccagctt gaaaaaaaaa    780
aa                                                                  782
```

<210> SEQ ID NO 2
<211> LENGTH: 725
<212> TYPE: DNA
<213> ORGANISM: Homo sapiens

<400> SEQUENCE: 2

```
gtccaggttc cgccccggag ccgacttcct cctggtcggc ggctgcagcg gggtgagcgg     60
cggcagcggc cggggatcct ggagccatgg ggcgcgcgcg cgacgccatc ctggatgcgc    120
tggagaacct gaccgccgag gagctcaaga agttcaagct gaagctgctg tcggtgccgc    180
tgcgcgaggg ctacgggcgc atcccgcggg gcgcgctgct gtccatggac gccttggacc    240
tcaccgacaa gctggtcagc ttctacctgg agacctacgg cgccgagctc accgctaacg    300
tgctgcgcga catgggcctg caggagatgg ccgggcagct gcaggcggcc acgcaccagg    360
gcctgcactt tatagaccag caccgggctg cgcttatcgc gagggtcaca aacgttgagt    420
ggctgctgga tgctctgtac gggaaggtcc tgacggatga gcagtaccag gcagtgcggg    480
ccgagcccac caacccaagc aagatgcgga agctcttcag tttcacacca gcctggaact    540
ggacctgcaa ggacttgctc ctccaggccc taagggagtc ccagtcctac ctggtggagg    600
acctggagcg gagctgaggc tccttcccag caacactccg gtcagcccct ggcaatccca    660
ccaaatcatc ctgaatctga tctttttata caatatac gaaaagccag cttgaaaaaa     720
aaaaa                                                                725
```

<210> SEQ ID NO 3
<211> LENGTH: 195
<212> TYPE: PRT
<213> ORGANISM: Homo sapiens

<400> SEQUENCE: 3

```
Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
            20                  25                  30

Arg Glu Gly Tyr Gly Arg Ile Pro Arg Gly Ala Leu Leu Ser Met Asp
        35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
        115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175
```

Leu Leu Gln Ala Leu Arg Glu Ser Gln Ser Tyr Leu Val Glu Asp Leu
            180                 185                 190

Glu Arg Ser
        195

<210> SEQ ID NO 4
<211> LENGTH: 176
<212> TYPE: PRT
<213> ORGANISM: Homo sapiens

<400> SEQUENCE: 4

Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Ser Val Pro Leu
            20                  25                  30

Arg Glu Gly Tyr Gly Arg Ile Pro Arg Gly Ala Leu Leu Ser Met Asp
        35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Leu His Phe Ile
                85                  90                  95

Asp Gln His Arg Ala Ala Leu Ile Ala Arg Val Thr Asn Val Glu Trp
            100                 105                 110

Leu Leu Asp Ala Leu Tyr Gly Lys Val Leu Thr Asp Glu Gln Tyr Gln
        115                 120                 125

Ala Val Arg Ala Glu Pro Thr Asn Pro Ser Lys Met Arg Lys Leu Phe
    130                 135                 140

Ser Phe Thr Pro Ala Trp Asn Trp Thr Cys Lys Asp Leu Leu Leu Gln
145                 150                 155                 160

Ala Leu Arg Glu Ser Gln Ser Tyr Leu Val Glu Asp Leu Glu Arg Ser
                165                 170                 175

<210> SEQ ID NO 5
<211> LENGTH: 2326
<212> TYPE: DNA
<213> ORGANISM: Homo sapiens

<400> SEQUENCE: 5
cttccttgga gccccgccgc ccgccgctca ctctgcacac gcagcagaag ggacgtggtg      60
ttccccaggc tctggccccc caggacctgc gcggatctgg cccagggcgc ctcgccgact     120
tccgtaaact gggcggaggg atgaaccccg acccagggga cggaggcgct cgccctctcg     180
ctgcagggtt ctgccctcaa cacttctggc cccgcctgtg aatggggggcc ggagcgatgg    240 ggcggggccg gcctccctcc ctcctcccag gctgacctct gccctccttc gagcacttcc     300
cgttcggggt gatgattgaa gaactgagtg tggacagagc acctgtcctc gccagcgccc     360
agctggaagc tgagttattt gtggctgcag cattccaacg cacacaccac cagaaatccc     420
cttcagcata ctggcctcag acctaccagg gcagagacct tgtcttgttt gctgctagaa     480
cccaggatcg ctggaaaatc acctagcagc agccaggtgc ggtgactcac gcctgtaatc     540
ccagcacttt ggaaggccaa ggcgggtgga tagcaaggtc aagagatcga accagcctg     600 gccaacatgc tctgggcacc tccagctcct gctcgccgga cggctcccag ggagagcaga    660
cgcgccagac gcgccaccct cggggcgccg acggtcacgg agcatggggt cggcctttga    720

-continued

```
gcgggtagtc cggagagtgg tccaggagct ggaccatggt ggggagttca tccctgtgac      780
cagcctgcag agctccactg gcttccagcc ctactgcctg gtggttagga agccctcaag      840
ctcatggttc tggaaacccc gttataagtg tgtcaacctg tctatcaagg acatcctgga      900
gccggatgcc gcggaaccag acgtgcagcg tggcaggagc ttccacttct acgatgccat      960
ggatgggcag atacagggca gcgtggagct ggcagcccca ggacaggcaa agatcgcagg     1020
cggggccgcg gtgtctgaca gctccagcac ctcaatgaat gtgtactcgc tgagtgtgga     1080
ccctaacacc tggcagactc tgctccatga gaggcacctg cggcagccag aacacaaagt     1140
cctgcagcag ctgcgcagcc gcgggga caa cgtgtacgtg gtgactgagg tgctgcagac     1200
acagaaggag gtggaagtca cgcgcaccca aagcgggag ggctcgggcc ggttttccct      1260
gcccggagcc acgtgcttgc agggtgaggg ccagggccat ctgagccaga agaagacggt     1320
caccatcccc tcaggcagca ccctcgcatt ccgggtggcc cagctggtta ttgactctga     1380
cttggacgtc cttctcttcc cggataagaa gcagaggacc ttccagccac cgcgacagg      1440 ccacaagcgt tccacgagcg aaggcgcctg gccacagctg ccctctggcc tctccatgat     1500
gaggtgcctc cacaacttcc tgacagatgg ggtccctgcg gagggggcgt tcactgaaga     1560
cttccagggc ctacgggcag aggtggagac catctccaag gaactggagc ttttggacag     1620
agagctgtgc cagctgctgc tggagggcct ggaggggtg ctgcgggacc agctggccct      1680
gcgagccttg gaggaggcgc tggagcaggg ccagagcctt gggccggtgg agccctgga     1740 cggtccagca ggtgctgtcc tggagtgcct ggtgttgtcc tccggaatgc tggtgccgga     1800
actcgctatc cctgttgtct acctgctggg ggcactgacc atgctgagtg aaacgcagca     1860
caagctgctg gcgcgaggcgc tggagtcgca gaccctgttg gggccgctcg agctggtggg     1920
cagcctcttg gagcagagtg cccgtgtggca ggagcgcagc accatgtccc tgccccccgg     1980
gctcctgggg aacagctggg gcgaaggagc accggcctgg gtcttgctgg acgagtgtgg     2040
cctagagctg ggggaggaca ctccccacgt gtgctgggag ccgcaggccc agggccgcat     2100
gtgtgcactc tacgcctccc tggcactgct atcaggactg agccaggagc cccactagcc     2160
tgtgcccggg catggcctgg cagctctcca gcagggcaga gtgtttgccc accagctgct     2220
agccctagga aggccaggag cccagtagcc atgtggccag tctaccatgg ggcccaggag     2280
ttggggaaac acaataaagg tggcatacga aggaaaaaaa aaaaaa                     2326
```

<210> SEQ ID NO 6
<211> LENGTH: 1772
<212> TYPE: DNA
<213> ORGANISM: Homo sapiens

<400> SEQUENCE: 6

```
gttccgggag ggcgtcctgg gcgggccctg cgtcaggttg cagtttcact tttagctctg       60
ggcacctcca gctcctgctc gccggacggc tcccagggag agcagacgcg ccagacgcgc      120
caccctcggg gcgccgacgg tcacggagca tggggtcggc ctttgagcgg gtagtccgga      180
gagtggtcca ggagctggac catggtgggg agttcatccc tgtgaccagc ctgcagagct      240
ccactggctt ccagccctac tgcctggtgg ttaggaagcc ctcaagctca tggttctgga      300
aaccccgtta taagtgtgtc aacctgtcta tcaaggacat cctggagccg gatgccgcgg      360
aaccagacgt gcagcgtggc aggagcttcc acttctacga tgccatggat gggcagatac      420
agggcagcgt ggagctggca gccccaggac aggcaaagat cgcaggcggg gccgcggtgt      480
```

```
ctgacagctc cagcacctca atgaatgtgt actcgctgag gtgtggaccct aacacctggc    540
agactctgct ccatgagagg cacctgcggc agccagaaca caaagtcctg cagcagctgc    600
gcagccgcgg ggacaacgtg tacgtggtga ctgaggtgct gcagacacag aaggaggtgg    660
aagtcacgcg cacccacaag cgggagggct cgggccggtt ttccctgccc ggagccacgt    720
gcttgcaggg tgagggccag ggccatctga gccagaagaa gacggtcacc atcccctcag    780
gcagcaccct cgcattccgg gtggcccagc tggttattga ctctgacttg gacgtccttc    840
tcttcccgga taagaagcag aggaccttcc agccacccgc gacaggccac aagcgttcca    900
cgagcgaagg cgcctggcca cagctgccct ctggcctctc catgatgagg tgcctccaca    960
acttcctgac agatggggtc cctgcggagg gggcgttcac tgaagacttc cagggcctac   1020
gggcagaggt ggagaccatc tccaaggaac tggagctttt ggacagagag ctgtgccagc   1080
tgctgctgga gggcctggag ggggtgctgc gggaccagct ggccctgcga gccttggagg   1140
aggcgctgga gcagggccag agccttgggc cggtggagcc cctggacggt ccagcaggtg   1200
ctgtcctgga gtgcctggtg ttgtcctccg gaatgctggt gccggaactc gctatccctg   1260
ttgtctacct gctgggggca ctgaccatgc tgagtgaaac gcagcacaag ctgctggcgg   1320
aggcgctgga gtcgcagacc ctgttgggc cgctcgagct ggtgggcagc ctcttggagc   1380
agagtgcccc gtggcaggag cgcagcacca tgtccctgcc cccgggctc ctggggaaca   1440
gctggggcga aggagcaccg gcctgggtct tgctggacga gtgtggccta gagctggggg   1500
aggacactcc ccacgtgtgc tgggagccgc aggcccaggg ccgcatgtgt gcactctacg   1560
cctccctggc actgctatca ggactgagcc aggagcccca ctagcctgtg cccgggcatg   1620
gcctggcagc tctccagcag ggcagagtgt tgcccacca gctgctagcc ctaggaaggc   1680
caggagccca gtagccatgt ggccagtcta ccatggggcc caggagttgg ggaaacacaa   1740
taaaggtggc atacgaagga aaaaaaaaaa aa                                  1772

<210> SEQ ID NO 7
<211> LENGTH: 484
<212> TYPE: PRT
<213> ORGANISM: Homo sapiens

<400> SEQUENCE: 7

Met Gly Ser Ala Phe Glu Arg Val Val Arg Val Val Gln Glu Leu
1               5                   10                  15

Asp His Gly Gly Glu Phe Ile Pro Val Thr Ser Leu Gln Ser Ser Thr
            20                  25                  30

Gly Phe Gln Pro Tyr Cys Leu Val Arg Lys Pro Ser Ser Ser Trp
        35                  40                  45

Phe Trp Lys Pro Arg Tyr Lys Cys Val Asn Leu Ser Ile Lys Asp Ile
    50                  55                  60

Leu Glu Pro Asp Ala Ala Glu Pro Asp Val Gln Arg Gly Arg Ser Phe
65                  70                  75                  80

His Phe Tyr Asp Ala Met Asp Gly Gln Ile Gln Gly Ser Val Glu Leu
                85                  90                  95

Ala Ala Pro Gly Gln Ala Lys Ile Ala Gly Gly Ala Ala Val Ser Asp
            100                 105                 110

Ser Ser Ser Thr Ser Met Asn Val Tyr Ser Leu Ser Val Asp Pro Asn
        115                 120                 125

Thr Trp Gln Thr Leu Leu His Glu Arg His Leu Arg Gln Pro Glu His
    130                 135                 140
```

```
Lys Val Gln Gln Leu Arg Ser Arg Gly Asp Asn Val Tyr Val Val
145                 150                 155                 160

Thr Glu Val Leu Gln Thr Gln Lys Glu Val Glu Val Thr Arg Thr His
                165                 170                 175

Lys Arg Glu Gly Ser Gly Arg Phe Ser Leu Pro Gly Ala Thr Cys Leu
            180                 185                 190

Gln Gly Glu Gly Gln Gly His Leu Ser Gln Lys Lys Thr Val Thr Ile
        195                 200                 205

Pro Ser Gly Ser Thr Leu Ala Phe Arg Val Ala Gln Leu Val Ile Asp
    210                 215                 220

Ser Asp Leu Asp Val Leu Leu Phe Pro Asp Lys Lys Gln Arg Thr Phe
225                 230                 235                 240

Gln Pro Pro Ala Thr Gly His Lys Arg Ser Thr Ser Glu Gly Ala Trp
                245                 250                 255

Pro Gln Leu Pro Ser Gly Leu Ser Met Met Arg Cys Leu His Asn Phe
            260                 265                 270

Leu Thr Asp Gly Val Pro Ala Glu Gly Ala Phe Thr Glu Asp Phe Gln
        275                 280                 285

Gly Leu Arg Ala Glu Val Glu Thr Ile Ser Lys Glu Leu Glu Leu Leu
    290                 295                 300

Asp Arg Glu Leu Cys Gln Leu Leu Glu Gly Leu Glu Gly Val Leu
305                 310                 315                 320

Arg Asp Gln Leu Ala Leu Arg Ala Leu Glu Glu Ala Leu Glu Gln Gly
                325                 330                 335

Gln Ser Leu Gly Pro Val Glu Pro Leu Asp Gly Pro Ala Gly Ala Val
            340                 345                 350

Leu Glu Cys Leu Val Leu Ser Ser Gly Met Leu Val Pro Glu Leu Ala
        355                 360                 365

Ile Pro Val Val Tyr Leu Leu Gly Ala Leu Thr Met Leu Ser Glu Thr
    370                 375                 380

Gln His Lys Leu Leu Ala Glu Ala Leu Glu Ser Gln Thr Leu Leu Gly
385                 390                 395                 400

Pro Leu Glu Leu Val Gly Ser Leu Leu Glu Gln Ser Ala Pro Trp Gln
                405                 410                 415

Glu Arg Ser Thr Met Ser Leu Pro Pro Gly Leu Leu Gly Asn Ser Trp
            420                 425                 430

Gly Glu Gly Ala Pro Ala Trp Val Leu Leu Asp Glu Cys Gly Leu Glu
        435                 440                 445

Leu Gly Glu Asp Thr Pro His Val Cys Trp Gly Pro Gln Ala Gln Gly
    450                 455                 460

Arg Met Cys Ala Leu Tyr Ala Ser Leu Ala Leu Leu Ser Gly Leu Ser
465                 470                 475                 480

Gln Glu Pro His

<210> SEQ ID NO 8
<211> LENGTH: 736
<212> TYPE: DNA
<213> ORGANISM: Rattus norvegicus

<400> SEQUENCE: 8
acgagcattc tcgaactctc caaatagcca ccaagcagga caataggcag tcttgatcat      60
ttaaactgct gcatggcaaa aggaatcgaa ggatttctta acagaagtgg ggggggggga     120
gatctgggct tcttcctgga agtttcctga tagagaaaat cttctgcctg ggtagaatct     180
```

```
cccaggatgc agggagatgg aaaaagttgt tccccagagg actttgtagt ctacagtgtt    240
gtcgtagcca tcggaacaac gagacaccct taatttggga gtgctctgaa agaaacttgc    300
ctctaggccc tagggctctc aggcaaggag gctaagaagg aatcctttgc tgtagccttt    360
tggatttagg tttctcagct tatctatccc tcagagaagt gtgtctatgt ccctttcctg    420
tccctctgcc tcaccccacc ccaacattcc aacctagggt aggggaggt cagtatacac    480 aaagccctct gtgtaagggg tggtatgtgt ccccccaccc ccctacccag agtatacaat    540 gccccttct gctccatgcc cctgccaccc tccccaccaa cctctcaatt gcacatgcca    600
ggctgcaatt ggtccactgg ctcaggacag ccccctcatg ctggggatcc aggggatttt    660
taagcaggtt ccagaaaaca ccactcagtt ccttgtcccc ccgctctctc caccccacag    720
acgctctgcc aagctt                                                    736

<210> SEQ ID NO 9
<211> LENGTH: 1350
<212> TYPE: DNA
<213> ORGANISM: Rattus norvegicus

<400> SEQUENCE: 9
aagcttaact ctggttatgt agacattcca aacatctccc tttgtttgtt gagatggtct     60
ctgatagccc aggctagctt tgaactcctg accttcctgc ttcctgcttc cacctcccaa    120
gcactagaaa gagaggcata aaccacagtt gactttctag ttcttcccca caattcttca    180
ggagatgctt acagcacacg agattaactt caccctcttc agtcatctaa gaccttcaca    240
cttcctgttc agacttcttt cctagtgaac ccttcaaga gccacaccaa atcaaacatg    300
gatggcacaa acatggatgc tctaaatcta cacagagctt cacaaatgtc acgtgcac    360 acactttcac ctcagctctt acctttgctg ttccatctag ccattgcccc tcccgttccc    420
tttttcaaaa tggctgctcc ttcaaggtct ctagacaaca ctgcttccta gacctgattc    480
ctctttcctc tgaacttcct gtattaagtg gcattcccac cgttctgtgc attggcagtt    540
gatgagtttc cctctgtttc tcccctctgc ctcctccaac tagatcttga gcttgtagaa    600
agaacggaat taccattcta atatgagcat tcgcattccc caatgtttca aatagccacc    660
aggcaggcca atacgcagtc ttgatcattt aaactgctgc attgcataag gtaccctaac    720
agacgggaga aatttgggct tcttcctgga gtttcctgg tagagaaaat cttctatctg    780
ggtagaatct cccagataca gggaggtgga aaaagttgtt ccaaagggct ttatagtcta    840
cagtgttgcc ttagcaatca gaacaacaga cacctaatt tgggagtgct ctgaaagaaa    900
cttgcctcta ggtcctaggg ctctcaggca aggagaccaa gaaggattcc tttgccatgg    960 cctttggat ttaggtttct cagcttgtct attcctcaga gaagtgtgtc tatgcccctt   1020
ttctgtccct ctgcctcacc ctaccccaac attccaacct agggtagggg gaggtcagta   1080
tacacaaagc cctctgtgta aggggtggta tgtgtccccc cacccctcca cccaccgtat   1140
acaatgcccc ttctgctcca tgcccctgc caccctcccc accacctctc cattgcacat   1200
gccaggctgc aattggtcac tggctcagga cagccccctc atgctgggga tccaggggat   1260
tttaagcagg ttcagaaaaa cacagctcag ttccttgtcc ccgctctct ccaccccaca   1320 gacactctgg gcctttgccc tacccagct                                   1350

<210> SEQ ID NO 10
<211> LENGTH: 982
<212> TYPE: DNA
<213> ORGANISM: Homo sapiens
```

<400> SEQUENCE: 10

```
gttcagttcc tggtccccca ctttctcaac cccacagatg ctccgggccc ctgccctgc       60
cccagctatg gctcctgggg ctccctcatc cagccccagc cctatcctgg ctgtgctgct      120
cttctcttct ttggtgctgt ccccggccca ggccatcgtg gtttacaccg acagggaggt      180
ccatggtgct gtgggctccc gggtgaccct gcactgctcc ttctggtcca gtgagtgggt      240
ctcagatgac atctccttca cctggcgcta ccagcccgaa gggggcagag atgccatttc      300
gatcttccac tatgccaagg acaaccccta cattgacgag gtggggacct tcaaagagcg      360
catccagtgg gtaggggacc ctcgctgaa ggatggctcc attgtcatac acaacctaga      420
ctacagtgac aatggcacgt tcacttgtga cgtcaaaaac cctccagaca tagtgggcaa      480
gacctctcag gtcacgctgt atgtctttga aaaagtgcca actaggtacg ggtcgttct      540
gggagctgtg atcggggtg tcctcggggt ggtgctgttg ctgctgctgc ttttctacgt       600
ggttcggtac tgctggctac gcaggcaggc ggccctgcag aggaggctca gtgctatgga      660
gaagggaaa ttgcacaagc caggaaagga cgcgtcgaag cgcgggcggc agacgccagt       720
gctgtatgca atgctggacc acagcagaag caccaaagct gtcagtgaga gaaggccaa      780
ggggctgggg gagtctcgca aggataagaa atagcggtta gcgggccggg cgggggatcg      840
ggggttaggg gtggagtccg ccaaaggccc aaaggtgatg gtcatcgaga tggagctacg      900
aaaggatgag cagagcccgg agctccggcc tgctgtcaag tcccccagca gaaccagcct      960
caaaaacgcc ctcaagaaca tg                                               982
```

<210> SEQ ID NO 11
<211> LENGTH: 1103
<212> TYPE: DNA
<213> ORGANISM: Homo sapiens

<400> SEQUENCE: 11

```
ctgtgggcag aacagggag agggccattg agaggccctt gtgactggag agtccaatca       60
aacgtaaagt gtgtgacagg gagggactcc tccaaattct gcaggtctct ccagactggg      120
gatccctaac acaagaggaa gtcttatgcc ccaagtgcca gaattccagg aaactcatgc      180
aatgaaacca gtcctcttgt gtcagagttt gcagctagaa gcggttcaag ggatggagga      240
ctctctggga gctggagtgg tacgctgcaa agaacctaaa tatgccataa cttcctttac      300
ttccctctcc aagaatttcc aattgctctt ccagcctatt ctgcctgaca ggttagaaag      360
ttttcaatag ttttcaatag aggttcgttt acttgcattg aattatctca tgaaggtcag      420
cttgattcgg gcacattaaa gacagagtcg gaagaacaca tttccctaag ttttattcta      480
atgtacaaca catgtgatca tttgcgatgg ggtctaggca gacaaggcag gtaacaggga      540
gtccttccaa ccaggggttg gaacaaagga ggcttgattt ggtgactctt gagacatttg      600
gctcactgct gtgatgctgt gagagattag ctgtgcaatg tttgggctcc ttaaaaggaa      660
gtttatttaa aataaaactt acctgcacgt atgtaacact gtagacacag atccttccca      720
cagtatattt aatctctgca gaattcactg ggaggggagg ggagccagtg ggacctcttg      780
gctattacac aggttggcac ttccagagag aacagtcttg gcatcacagg cttcaggcat      840
actcaaagct cttctcccctt ctgattccag tttctccatg ccctgcaggg cctcttggga      900
ttattgtatt ctgaaagca aacaaagttg gacactgtct ctttaaataa tagaggctga      960
gaacctctca ggccaccatg acatatccca gcattggacc agcccctgaa taaactggaa     1020
```

-continued agacgcctgg tctggcttca gttacaggga gcaccaccag ggaacatctc ggggagcctg    1080
gttggaagct gcaggcttag tct                                           1103

<210> SEQ ID NO 12
<211> LENGTH: 1280
<212> TYPE: DNA
<213> ORGANISM: Homo sapiens

<400> SEQUENCE: 12
gtggatggat ggatgcatga gtggatggat ggatgagtgg atagatggag gagtgggtgg      60
atgggtgaac ggatggatga gtggatgggg gatggatgga tgcatggatg gatggatggg     120
taggtgggtg tgtgtatgga tggatggata gatggatgga tgggtaaatg gactgttatg     180
tggatggatg gatgaatgga tagagagata gatggatgac tggtattaca ggaatatgtg     240
agtgaatcct gttttctgta gataagtaat agagtttgga gaggaaacta actaaatgat     300
atttatttaa acctaacact ctaacttgaa agcaaaatgg attcattgcc cttcgtgaca     360
gaaatgtggt attttttgga gaaagctatg agatgctggt atacaacatg aaatatctca     420
atcccacttc agatttctaa ttgtttctgc ttccagagga gaagccaagt caaaatgtcc     480
tgaataagca gttctctatt gtgagaggcc tcttgtggaa tctgggattg aaacaattct     540 aaatgccccca cttctttcat gcatgaattg caaaaagatg tggcaagttt tgtttctacc    600
aagaaaacta aaaacacctt ttgtcaaata aatgctcctt gcatatttaa cttatgcacc     660
agtggccttt taaacagtca atgtcccatc aaggtgcctg cacatctggg ctctccggga     720
gcagccatgg cagcacccgg gaagaaacgc tgatgtggct gctctgcatg ctcagatgac     780
ttcatcggga agcctgggtg cattttacgc tgggtgccaa atctcgagta actgaggaat     840
tcccagagcc ttctgaaaca cagagctgca ataaggctgc tccatccagg ttagctccat     900
cctaggccaa gggctttatg aggactgcac atattctgtg ggttttatag agacagcta      960 ggtcaagacc cctcagagaa agctgctttg tccggtgctc agctttgcac aggcccgtat    1020
tcatatctca ttgttgtttg caggagaggc agatgcgaac cagaacaatg ggacctcctc    1080
tcaggacaca gcggtgactg actccaagcg cacagcggac ccgaagaatg cctggcagga    1140
tgcccaccca gctgacccag ggagccgccc ccacttgatc cgcctcttt cccgagatgc     1200 cccggggagg gaggacaaca ccttcaaaga caggccctct gagtccgacg agctccagac    1260
catccaagaa gacagtgcag                                                1280

<210> SEQ ID NO 13
<211> LENGTH: 4
<212> TYPE: PRT
<213> ORGANISM: Unknown
<220> FEATURE:
<223> OTHER INFORMATION: Description of Unknown:
      Caspase 3 inhibitor peptide

<400> SEQUENCE: 13

Asp Glu Val Asp
1

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
ggggattttg gagttatggg g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaataatccc cttcccttcc c                                              21

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagaagttta agttgaagtt gttgt                                          25

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
accatctcct acaaacccat atc                                            23

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtgatatcgc caccatgggg cgcgcgcgcg                                     30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggatatcct agctccgctc caggtcctcc                                     30

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
```

```
gtcaagcttg ccaccatggg gcgcgcgc                                              28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caactagtct agctccgctc caggtcct                                              28

<210> SEQ ID NO 22
<211> LENGTH: 248
<212> TYPE: DNA
<213> ORGANISM: Homo sapiens

<400> SEQUENCE: 22
gatatgggtt tgtaggagat ggtcgggtag ttgtaggcgg ttacgtatta gggtgagtcg           60
ttttcgtttt tttttatttc gttttttttt tttatttata ttagcgttta tttcgcgggt          120
tttttcgttt tttgttttttt ttatttttaa ataaagttgt tttatcggaa aggaggtttt         180
ttacgtttgg tttatcgatt aacgggattt cggtttttacg gcgggaaggg aagggaaggg         240
gattattt                                                                  248
```